(12) United States Patent
Levinson et al.

(10) Patent No.: US 11,166,743 B2
(45) Date of Patent: Nov. 9, 2021

(54) DEVICES AND METHODS FOR COSMETIC SKIN RESURFACING

(71) Applicant: Cytrellis Biosystems, Inc., Woburn, MA (US)

(72) Inventors: Douglas Levinson, Sherborn, MA (US); Alec Ginggen, Medford, MA (US); Kristian DiMatteo, Waltham, MA (US); Robert Brik, Boston, MA (US); Jose Lizardi, Boston, MA (US); Nicholas Anderson, Boston, MA (US); Oivind Brockmeier, Boston, MA (US)

(73) Assignee: Cytrellis Biosystems, Inc., Woburn, MA (US)

( * ) Notice: Subject to any disclaimer, the term of this patent is extended or adjusted under 35 U.S.C. 154(b) by 56 days.

(21) Appl. No.: 16/090,034

(22) PCT Filed: Mar. 29, 2017

(86) PCT No.: PCT/US2017/024752
§ 371 (c)(1),
(2) Date: Sep. 28, 2018

(87) PCT Pub. No.: WO2017/172920
PCT Pub. Date: Oct. 5, 2017

(65) Prior Publication Data
US 2019/0099199 A1    Apr. 4, 2019

Related U.S. Application Data

(60) Provisional application No. 62/314,748, filed on Mar. 29, 2016.

(51) Int. Cl.
*A61B 17/3205*    (2006.01)
*A61B 17/32*    (2006.01)
(Continued)

(52) U.S. Cl.
CPC ........ *A61B 17/3417* (2013.01); *A61B 17/205* (2013.01); *A61B 17/32053* (2013.01);
(Continued)

(58) Field of Classification Search
CPC .... A61B 17/32053; A61B 2017/00752; A61B 2017/00761; A61B 2017/320064; A61B 10/0283
See application file for complete search history.

(56) References Cited

U.S. PATENT DOCUMENTS 2,426,535 A    8/1947    Turkel
2,496,111 A    1/1950    Turkel
(Continued)

FOREIGN PATENT DOCUMENTS

AU    2012 211 122 B2    7/2016
CA    1275215 C    10/1990
(Continued)

OTHER PUBLICATIONS

Alsberg, E. et al., Engineering growing tissues, PNAS, 99(19):12025-12030 (2002).
(Continued)

*Primary Examiner* — Wade Miles
(74) *Attorney, Agent, or Firm* — Onello & Mello, LLP

(57) ABSTRACT

Disclosed herein are apparatuses, kits, and methods for treating skin, such as skin tightening, e.g., reducing skin laxity, for treating conditions that would benefit from tissue area or volume reduction, skin restoration, skin tightening, skin lifting, and/or skin repositioning, and/or for generally improving skin function or appearance. Such apparatuses, kits, and methods include one or more hollow needles each having at least one prong and a mechanism for removing skin tissue portion(s) from the hollow needle(s).

20 Claims, 29 Drawing Sheets

(51) Int. Cl.
*A61B 17/34* (2006.01)
*A61B 17/20* (2006.01)
*A61B 17/00* (2006.01)

(52) U.S. Cl.
CPC .......... *A61B 2017/00761* (2013.01); *A61B 2017/00792* (2013.01); *A61B 2017/320064* (2013.01); *A61B 2017/3454* (2013.01); *A61B 2217/005* (2013.01)

(56) References Cited

U.S. PATENT DOCUMENTS

| | | | |
|---|---|---|---|
| 2,881,763 A | 4/1959 | Robbins | |
| 3,001,522 A | 9/1961 | Silverman | |
| 3,086,530 A | 4/1963 | Groom | |
| 3,214,869 A | 11/1965 | Stryker | |
| 3,598,108 A | 8/1971 | Jamshidi et al. | |
| 3,640,279 A | 2/1972 | Brown et al. | |
| 3,683,892 A | 8/1972 | Harris | |
| 3,788,320 A | 1/1974 | Dye | |
| 3,867,942 A | 2/1975 | Bellantoni et al. | |
| 3,929,123 A | 12/1975 | Jamshidi | |
| 4,108,096 A | 8/1978 | Ciecior | |
| 4,159,659 A | 7/1979 | Nightingale | |
| 4,167,179 A | 9/1979 | Kirsch | |
| 4,403,617 A | 9/1983 | Tretinyak | |
| 4,458,678 A | 7/1984 | Yannas et al. | |
| 4,476,864 A | 10/1984 | Tezel | |
| 4,604,346 A | 8/1986 | Bell et al. | |
| 4,640,296 A | 2/1987 | Schnepp-Pesch et al. | |
| 4,649,918 A | 3/1987 | Pegg et al. | |
| D297,375 S | 8/1988 | Liu | |
| 4,815,462 A | 3/1989 | Clark | |
| 4,865,026 A | 9/1989 | Barrett | |
| 4,903,709 A | 2/1990 | Skinner | |
| D323,034 S | 1/1992 | Reinstein | |
| 5,152,763 A | 10/1992 | Johnson | |
| D338,070 S | 8/1993 | Lam | |
| 5,242,453 A | 9/1993 | Gubich | |
| D342,138 S | 12/1993 | Wollman et al. | |
| 5,269,316 A | 12/1993 | Spitalny | |
| 5,306,490 A | 4/1994 | Barley, Jr. | |
| 5,324,305 A | 6/1994 | Kanner | |
| 5,331,972 A | 7/1994 | Wadhwani et al. | |
| 5,415,182 A | 5/1995 | Chin et al. | |
| 5,417,683 A | 5/1995 | Shiao | |
| 5,419,761 A | 5/1995 | Narayanan et al. | |
| 5,439,475 A | 8/1995 | Bennett | |
| 5,458,112 A | 10/1995 | Weaver | |
| D377,404 S | 1/1997 | Izumi | |
| 5,593,381 A | 1/1997 | Tannenbaum et al. | |
| 5,611,810 A | 3/1997 | Arnold et al. | |
| 5,615,690 A | 4/1997 | Giurtino et al. | |
| 5,639,654 A | 6/1997 | Bernard et al. | |
| 5,643,308 A | 7/1997 | Markman | |
| D388,543 S | 12/1997 | Eguchi et al. | |
| 5,713,375 A | 2/1998 | McAllister | |
| 5,749,895 A | 5/1998 | Sawyer et al. | |
| 5,792,169 A | 8/1998 | Markman | |
| 5,810,857 A | 9/1998 | Mackool | |
| 5,827,297 A | 10/1998 | Boudjema | |
| 5,868,744 A | 2/1999 | Willmen | |
| 5,879,326 A | 3/1999 | Godshall et al. | |
| 5,885,211 A | 3/1999 | Eppstein et al. | |
| 5,885,226 A | 3/1999 | Rubinstein et al. | |
| 5,902,319 A | 5/1999 | Daley | |
| 5,922,000 A | 7/1999 | Chodorow | |
| 5,925,002 A | 7/1999 | Wollman | |
| 5,928,162 A | 7/1999 | Giurtino et al. | |
| 5,931,855 A | 8/1999 | Buncke | |
| 5,989,273 A | 11/1999 | Arnold | |
| 6,022,324 A | 2/2000 | Skinner | |
| D425,241 S | 5/2000 | Nishizawa et al. | |
| 6,059,807 A | 5/2000 | Boudjema | |
| 6,063,094 A | 5/2000 | Rosenberg | |
| 6,178,346 B1 | 1/2001 | Amundson et al. | |
| 6,197,039 B1 | 3/2001 | Ashraf | |
| 6,211,598 B1 | 4/2001 | Dhuler et al. | |
| 6,241,687 B1 | 6/2001 | Voegele et al. | |
| 6,241,739 B1 | 6/2001 | Waldron | |
| 6,251,097 B1 | 6/2001 | Kline et al. | |
| 6,264,618 B1 | 7/2001 | Landi et al. | |
| 6,342,213 B1 | 1/2002 | Barley et al. | |
| D457,265 S | 5/2002 | Gebhard | |
| D458,710 S | 6/2002 | Altamore et al. | |
| 6,419,641 B1 | 7/2002 | Mark et al. | |
| 6,432,098 B1 | 8/2002 | Kline et al. | |
| 6,440,086 B1 | 8/2002 | Hohenberg | |
| 6,461,369 B1 | 10/2002 | Kim | |
| 6,537,264 B1 | 3/2003 | Cormier et al. | |
| 6,562,037 B2 | 5/2003 | Paton et al. | |
| 6,669,618 B2 | 12/2003 | Reising et al. | |
| 6,669,694 B2 | 12/2003 | Shadduck | |
| 6,733,496 B2 | 5/2004 | Sharkey et al. | |
| 6,733,498 B2 | 5/2004 | Paton et al. | |
| D500,391 S | 12/2004 | Nielsen et al. | |
| 6,881,203 B2 | 4/2005 | Delmore et al. | |
| 6,887,250 B1 | 5/2005 | Dority et al. | |
| 6,893,388 B2 | 5/2005 | Reising et al. | |
| 6,936,039 B2 | 8/2005 | Kline et al. | |
| D509,301 S | 9/2005 | Talbot et al. | |
| 6,997,923 B2 | 2/2006 | Anderson et al. | |
| 7,073,510 B2 | 7/2006 | Redmond et al. | |
| 7,131,951 B2 | 11/2006 | Angel | |
| D538,430 S | 3/2007 | Ohta | |
| 7,618,429 B2 | 11/2009 | Mulholland | |
| 7,651,507 B2 | 1/2010 | Mishra et al. | |
| 7,658,728 B2 | 2/2010 | Yuzhakov | |
| 7,926,401 B2 | 4/2011 | Mishra et al. | |
| 8,128,639 B2 | 3/2012 | Tippett | |
| 8,209,006 B2 | 6/2012 | Smith et al. | |
| 8,226,664 B2 | 7/2012 | Drews et al. | |
| 8,246,611 B2 | 8/2012 | Paithankar et al. | |
| 8,435,791 B2 | 5/2013 | Galun et al. | |
| 8,480,592 B2 | 7/2013 | Chudzik et al. | |
| 8,696,686 B2 | 4/2014 | Drews et al. | |
| 8,900,181 B2 | 12/2014 | Knowlton | |
| 9,017,343 B2 | 4/2015 | Westerling, Jr. et al. | |
| 9,060,803 B2 | 6/2015 | Anderson et al. | |
| 9,084,465 B2 | 7/2015 | Oostman, Jr. et al. | |
| 9,119,945 B2 | 9/2015 | Simons et al. | |
| 9,439,673 B2 | 9/2016 | Austen | |
| 9,561,051 B2 | 2/2017 | Austen et al. | |
| D797,286 S | 9/2017 | Ginggen et al. | |
| 10,251,792 B2 | 4/2019 | Levinson et al. | |
| 10,543,127 B2 | 1/2020 | Levinson et al. | |
| 10,555,754 B2 | 2/2020 | Ginggen et al. | |
| 10,953,143 B2 | 3/2021 | Ginggen et al. | |
| 2001/0018572 A1 | 8/2001 | Kinsey et al. | |
| 2002/0022854 A1 | 2/2002 | Irion et al. | |
| 2002/0022861 A1 | 2/2002 | Jacobs et al. | |
| 2002/0045859 A1 | 4/2002 | Gartstein et al. | |
| 2002/0103500 A1 | 8/2002 | Gildenberg | |
| 2002/0120260 A1 | 8/2002 | Morris et al. | |
| 2002/0169431 A1 | 11/2002 | Kline et al. | |
| 2002/0183688 A1 | 12/2002 | Lastovich et al. | |
| 2002/0187556 A1 | 12/2002 | Shartle et al. | |
| 2002/0188280 A1 | 12/2002 | Nguyen et al. | |
| 2003/0023196 A1 | 1/2003 | Liguori | |
| 2003/0083607 A1 | 5/2003 | Bobo | |
| 2003/0088220 A1 | 5/2003 | Molander et al. | |
| 2003/0119641 A1 | 6/2003 | Reising | |
| 2003/0135161 A1 | 7/2003 | Fleming et al. | |
| 2003/0144656 A1 | 7/2003 | Ocel et al. | |
| 2003/0153960 A1 | 8/2003 | Chornenky et al. | |
| 2003/0158521 A1 | 8/2003 | Ameri | |
| 2003/0158566 A1 | 8/2003 | Brett | |
| 2003/0163160 A1 | 8/2003 | O'Malley et al. | |
| 2003/0181936 A1 | 9/2003 | Trautman et al. | |
| 2003/0195625 A1 | 10/2003 | Garcia Castro et al. | |
| 2003/0199811 A1 | 10/2003 | Sage et al. | |
| 2003/0212415 A1 | 11/2003 | Karasiuk | |
| 2003/0233082 A1 | 12/2003 | Kline et al. | |
| 2004/0002723 A1 | 1/2004 | Ball | |

(56) References Cited

U.S. PATENT DOCUMENTS

| | | |
|---|---|---|
| 2004/0010268 A1 | 1/2004 | Gabehart |
| 2004/0015139 A1 | 1/2004 | La Bianco et al. |
| 2004/0019297 A1 | 1/2004 | Angel |
| 2004/0023771 A1 | 2/2004 | Reising et al. |
| 2004/0054410 A1 | 3/2004 | Barrows |
| 2004/0073195 A1 | 4/2004 | Cucin |
| 2004/0087992 A1 | 5/2004 | Gartstein et al. |
| 2004/0122471 A1 | 6/2004 | Toby et al. |
| 2004/0138680 A1 | 7/2004 | Twitchell et al. |
| 2004/0162566 A1 | 8/2004 | Carson et al. |
| 2004/0175690 A1 | 9/2004 | Mishra et al. |
| 2004/0220589 A1 | 11/2004 | Feller |
| 2005/0049582 A1 | 3/2005 | DeBenedictis et al. |
| 2005/0090765 A1 | 4/2005 | Fisher |
| 2005/0130821 A1 | 6/2005 | Reising et al. |
| 2005/0165329 A1 | 7/2005 | Taylor et al. |
| 2005/0171480 A1 | 8/2005 | Mukerjee et al. |
| 2005/0203575 A1 | 9/2005 | Carson et al. |
| 2005/0209567 A1 | 9/2005 | Sibbitt |
| 2005/0215921 A1 | 9/2005 | Hibner et al. |
| 2005/0215970 A1 | 9/2005 | Kline et al. |
| 2005/0215971 A1 | 9/2005 | Roe et al. |
| 2005/0226856 A1 | 10/2005 | Ahlfors |
| 2005/0234419 A1 | 10/2005 | Kline et al. |
| 2005/0245952 A1 | 11/2005 | Feller |
| 2005/0283141 A1 | 12/2005 | Giovannoli |
| 2006/0047234 A1 | 3/2006 | Glucksman et al. |
| 2006/0064031 A1 | 3/2006 | Miller |
| 2006/0116605 A1 | 6/2006 | Nakao |
| 2006/0155266 A1 | 7/2006 | Manstein et al. |
| 2006/0161179 A1 | 7/2006 | Kachenmeister |
| 2006/0184153 A1 | 8/2006 | Mark et al. |
| 2006/0193819 A1 | 8/2006 | Lu et al. |
| 2006/0216781 A1 | 9/2006 | Gebing |
| 2006/0259006 A1 | 11/2006 | McKay et al. |
| 2006/0264926 A1 | 11/2006 | Kochamba |
| 2006/0271070 A1 | 11/2006 | Eriksson et al. |
| 2006/0276806 A1 | 12/2006 | Martinez Zunino |
| 2007/0010810 A1 | 1/2007 | Kochamba |
| 2007/0038181 A1 | 2/2007 | Melamud et al. |
| 2007/0038236 A1 | 2/2007 | Cohen |
| 2007/0060888 A1 | 3/2007 | Goff et al. |
| 2007/0073217 A1 | 3/2007 | James |
| 2007/0073327 A1 | 3/2007 | Giovannoli |
| 2007/0078359 A1 | 4/2007 | Luloh et al. |
| 2007/0078466 A1 | 4/2007 | Bodduluri et al. |
| 2007/0078473 A1 | 4/2007 | Bodduluri et al. |
| 2007/0106306 A1 | 5/2007 | Bodduluri et al. |
| 2007/0142722 A1 | 6/2007 | Chang |
| 2007/0142744 A1 | 6/2007 | Provencher |
| 2007/0142885 A1 | 6/2007 | Hantash et al. |
| 2007/0149991 A1 | 6/2007 | Mulholland |
| 2007/0156161 A1 | 7/2007 | Weadock et al. |
| 2007/0167958 A1 | 7/2007 | Sulamanidze et al. |
| 2007/0179455 A1 | 8/2007 | Geliebter et al. |
| 2007/0183938 A1 | 8/2007 | Booker |
| 2007/0198000 A1 | 8/2007 | Miyamoto et al. |
| 2007/0213634 A1 | 9/2007 | Teague |
| 2007/0239236 A1 | 10/2007 | Manstein |
| 2007/0239260 A1 | 10/2007 | Palanker et al. |
| 2007/0249960 A1 | 10/2007 | Williamson |
| 2007/0270710 A1 | 11/2007 | Frass et al. |
| 2008/0009802 A1 | 1/2008 | Lambino et al. |
| 2008/0009896 A1 | 1/2008 | Shiao |
| 2008/0009901 A1 | 1/2008 | Redmond et al. |
| 2008/0033334 A1 | 2/2008 | Gurtner et al. |
| 2008/0045858 A1 | 2/2008 | Tessitore et al. |
| 2008/0045861 A1 | 2/2008 | Miller et al. |
| 2008/0132979 A1 | 6/2008 | Gerber |
| 2008/0146982 A1 | 6/2008 | Rastegar et al. |
| 2008/0183167 A1 | 7/2008 | Britva et al. |
| 2008/0208146 A1 | 8/2008 | Brandwein et al. |
| 2008/0221548 A1 | 9/2008 | Danenberg et al. |
| 2008/0234602 A1 | 9/2008 | Oostman et al. |
| 2008/0234699 A1 | 9/2008 | Oostman, Jr. et al. |
| 2008/0269735 A1 | 10/2008 | Vila Echague et al. |
| 2008/0275378 A1 | 11/2008 | Herndon |
| 2008/0300507 A1 | 12/2008 | Figueredo et al. |
| 2008/0306471 A1 | 12/2008 | Altshuler et al. |
| 2008/0312648 A1 | 12/2008 | Peterson |
| 2009/0030340 A1 | 1/2009 | Mc Clellan |
| 2009/0048557 A1 | 2/2009 | Yeshurun et al. |
| 2009/0088720 A1 | 4/2009 | Oostman, Jr. |
| 2009/0093864 A1 | 4/2009 | Anderson |
| 2009/0146068 A1 | 6/2009 | Agarwal |
| 2009/0163877 A1 | 6/2009 | Christoffersen et al. |
| 2009/0198336 A1 | 8/2009 | Qiao et al. |
| 2009/0227895 A1 | 9/2009 | Goldenberg |
| 2009/0312749 A1 | 12/2009 | Pini et al. |
| 2010/0023003 A1 | 1/2010 | Mulholland |
| 2010/0041938 A1 | 2/2010 | Stoianovici et al. |
| 2010/0057100 A1 | 3/2010 | Zeevi |
| 2010/0082042 A1 | 4/2010 | Drews |
| 2010/0121307 A1 | 5/2010 | Lockard et al. |
| 2010/0145373 A1 | 6/2010 | Alon |
| 2010/0160822 A1 | 6/2010 | Parihar et al. |
| 2010/0185116 A1 | 7/2010 | Al-Mohizea |
| 2010/0330589 A1 | 12/2010 | Bahrami et al. |
| 2011/0009882 A1 | 1/2011 | Remsburg et al. |
| 2011/0028898 A1 | 2/2011 | Clark, III et al. |
| 2011/0040497 A1 | 2/2011 | Olesen |
| 2011/0046616 A1 | 2/2011 | Manstein |
| 2011/0092844 A1 | 4/2011 | Bargo et al. |
| 2011/0105949 A1 | 5/2011 | Wiksell |
| 2011/0152738 A1 | 6/2011 | Zepeda et al. |
| 2011/0166520 A1 | 7/2011 | Iwase et al. |
| 2011/0172745 A1 | 7/2011 | Na et al. |
| 2011/0245834 A1 | 10/2011 | Miklosovic |
| 2011/0251602 A1 | 10/2011 | Anderson et al. |
| 2011/0257588 A1 | 10/2011 | Knowlton |
| 2011/0270274 A1 | 11/2011 | Hull, Jr. |
| 2011/0282238 A1 | 11/2011 | Houser et al. |
| 2011/0313345 A1 | 12/2011 | Schafer |
| 2011/0313429 A1 | 12/2011 | Anderson et al. |
| 2012/0041430 A1 | 2/2012 | Anderson et al. |
| 2012/0065551 A1 | 3/2012 | Aviad et al. |
| 2012/0136387 A1 | 5/2012 | Redmond et al. |
| 2012/0158100 A1 | 6/2012 | Schomacker |
| 2012/0209283 A1 | 8/2012 | Zhu |
| 2012/0226214 A1 | 9/2012 | Gurtner et al. |
| 2012/0226268 A1 | 9/2012 | Liu et al. |
| 2012/0226306 A1 | 9/2012 | Jackson et al. |
| 2012/0245629 A1 | 9/2012 | Gross et al. |
| 2012/0253333 A1 | 10/2012 | Garden et al. |
| 2012/0259237 A1 | 10/2012 | Axelrod |
| 2012/0271320 A1 | 10/2012 | Hall et al. |
| 2013/0006168 A1 | 1/2013 | Del Vecchio |
| 2013/0041397 A1 | 2/2013 | Nishimura |
| 2013/0045171 A1 | 2/2013 | Utecht et al. |
| 2013/0110026 A1 | 5/2013 | Jackson et al. |
| 2013/0131635 A1 | 5/2013 | Rimsa et al. |
| 2013/0204238 A1 | 8/2013 | Lederman et al. |
| 2014/0036523 A1 | 2/2014 | Thullier et al. |
| 2014/0039523 A1 | 2/2014 | Austen |
| 2014/0163582 A1 | 6/2014 | Austen et al. |
| 2014/0200484 A1 | 7/2014 | Austen et al. |
| 2014/0249547 A1 | 9/2014 | Boone, III |
| 2014/0277055 A1 | 9/2014 | Austen, Jr. |
| 2014/0296741 A1 | 10/2014 | Austen |
| 2014/0296796 A1 | 10/2014 | Lim |
| 2014/0303648 A1 | 10/2014 | Knowlton |
| 2014/0343481 A1 | 11/2014 | Ignon |
| 2015/0143713 A1 | 5/2015 | Cheng |
| 2015/0173991 A1 | 6/2015 | Anderson et al. |
| 2015/0238214 A1 | 8/2015 | Anderson et al. |
| 2015/0258319 A1 | 9/2015 | Simmers |
| 2015/0320990 A1 | 11/2015 | Burton et al. |
| 2015/0366719 A1 | 12/2015 | Levinson et al. |
| 2016/0082241 A1 | 3/2016 | Burton et al. |
| 2016/0095592 A1 | 4/2016 | Levinson et al. |
| 2016/0121091 A1 | 5/2016 | Burton et al. |
| 2016/0129198 A1 | 5/2016 | Bitar et al. |
| 2016/0136406 A1 | 5/2016 | Berry et al. |
| 2016/0192961 A1 | 7/2016 | Ginggen et al. |

(56) References Cited

U.S. PATENT DOCUMENTS

| | | |
|---|---|---|
| 2016/0317721 A1 | 11/2016 | Ginggen et al. |
| 2016/0367280 A1 | 12/2016 | Austen |
| 2017/0367729 A1 | 12/2017 | Ginggen et al. |
| 2018/0008500 A1 | 1/2018 | Anderson et al. |
| 2018/0021087 A1 | 1/2018 | Anderson et al. |
| 2018/0078278 A1 | 3/2018 | Levinson et al. |
| 2018/0185196 A1 | 7/2018 | Levinson et al. |
| 2018/0193054 A1 | 7/2018 | Austen |
| 2018/0206875 A1 | 7/2018 | Austen et al. |
| 2019/0366067 A1 | 12/2019 | Ginggen et al. |
| 2020/0038051 A1 | 2/2020 | Austen |
| 2020/0121354 A1 | 4/2020 | Ginggen et al. |
| 2020/0188184 A1 | 6/2020 | Levinson et al. |
| 2020/0214766 A1 | 7/2020 | Anderson et al. |
| 2020/0246039 A1 | 8/2020 | Levinson et al. |
| 2021/0059703 A1 | 3/2021 | Austen et al. |
| 2021/0178028 A1 | 6/2021 | Ginggen et al. |

FOREIGN PATENT DOCUMENTS

| | | |
|---|---|---|
| CA | 2361777 A1 | 5/2002 |
| CN | 2126570 Y | 1/1993 |
| CN | 1115629 A | 1/1996 |
| CN | 201005966 Y | 1/2008 |
| CN | 101128156 A | 2/2008 |
| CN | 101208128 A | 6/2008 |
| CN | 101232858 A | 7/2008 |
| CN | 101277657 A | 10/2008 |
| CN | 101312692 A | 11/2008 |
| CN | 101347346 A | 1/2009 |
| CN | 101563113 A | 10/2009 |
| CN | 101670145 A | 3/2010 |
| CN | 102119006 A | 7/2011 |
| CN | 102143724 A | 8/2011 |
| CN | 102178616 A | 9/2011 |
| CN | 202113484 U | 1/2012 |
| CN | 103547226 A | 1/2014 |
| DE | 287651 A5 | 3/1991 |
| DE | 202004010659 U1 | 10/2004 |
| DE | 102007026973 A1 | 12/2008 |
| EA | 009092 | 10/2007 |
| EP | 0027974 A1 | 5/1981 |
| EP | 1224949 A1 | 7/2002 |
| EP | 1278061 A1 | 1/2003 |
| EP | 1396230 A1 | 3/2004 |
| EP | 1618925 A1 | 1/2006 |
| EP | 2181732 A1 | 5/2010 |
| EP | 1278061 B1 | 2/2011 |
| EP | 2409727 A1 | 1/2012 |
| FR | 2846221 B1 | 7/2005 |
| JP | S57-163208 A | 10/1982 |
| JP | 2000-139929 A | 5/2000 |
| JP | 2001-187058 A | 7/2001 |
| JP | 2002-505605 A | 2/2002 |
| JP | 2003-515424 A | 5/2003 |
| JP | 2003-518975 A | 6/2003 |
| JP | 2003-532480 A | 11/2003 |
| JP | 2004-503342 A | 2/2004 |
| JP | 2005-000642 A | 1/2005 |
| JP | 2005-87519 A | 4/2005 |
| JP | 2005-87520 A | 4/2005 |
| JP | 2005-103276 A | 4/2005 |
| JP | 2006-516201 A | 6/2006 |
| JP | 2006-517814 A | 8/2006 |
| JP | 2007-041267 A | 2/2007 |
| JP | 2007-100140 A | 4/2007 |
| JP | 2008-036393 A | 2/2008 |
| JP | 2008-528207 A | 7/2008 |
| JP | 2009-502413 A | 1/2009 |
| JP | 2009-507773 A | 2/2009 |
| JP | 2009-509671 A | 3/2009 |
| JP | 2009-172418 A | 8/2009 |
| JP | 2009-219858 A | 10/2009 |
| JP | 2009-545382 A | 12/2009 |
| JP | 2010-000210 A | 1/2010 |
| JP | 4431637 B2 | 3/2010 |
| JP | 2010-515469 A | 5/2010 |
| JP | 2010-524591 A | 7/2010 |
| JP | 2010-525887 A | 7/2010 |
| JP | 2010-532178 A | 10/2010 |
| JP | 2011-516169 A | 5/2011 |
| JP | 2013-526300 A | 6/2013 |
| JP | 2014-506498 | 3/2014 |
| JP | 5944925 B2 | 7/2016 |
| KR | 2008-0030553 A | 4/2008 |
| KR | 2008-0049793 A | 6/2008 |
| KR | 2010-0135863 A | 12/2010 |
| KR | 2010/0135864 A | 12/2010 |
| KR | 10-2012-0135429 A | 12/2012 |
| KR | 101571291 B1 | 11/2015 |
| RU | 1801391 C | 3/1993 |
| RU | 2119304 C1 | 9/1998 |
| RU | 2289332 C2 | 12/2006 |
| RU | 2308873 C2 | 10/2007 |
| RU | 2325859 C2 | 6/2008 |
| TW | 402497 B | 8/2000 |
| TW | 200841866 A | 11/2008 |
| WO | WO-93/22971 A1 | 11/1993 |
| WO | WO-1995/28896 A1 | 11/1995 |
| WO | WO-97/18758 A1 | 5/1997 |
| WO | WO-98/26719 A1 | 6/1998 |
| WO | WO-98/57587 A1 | 12/1998 |
| WO | WO-99/29243 A1 | 6/1999 |
| WO | WO-0141651 A2 | 6/2001 |
| WO | WO-01/49186 A2 | 7/2001 |
| WO | WO-01/85035 A2 | 11/2001 |
| WO | WO-02/05890 A2 | 1/2002 |
| WO | WO-02/096321 A1 | 12/2002 |
| WO | WO-2004/045671 A2 | 6/2004 |
| WO | WO-2004/107984 A1 | 12/2004 |
| WO | WO-2005/013830 A1 | 2/2005 |
| WO | WO-2005/072181 A2 | 8/2005 |
| WO | WO-2005/109799 A2 | 11/2005 |
| WO | WO-2006/081556 A2 | 8/2006 |
| WO | WO-2006/116281 A2 | 11/2006 |
| WO | WO-2006/118804 A1 | 11/2006 |
| WO | WO-2007/011788 A2 | 1/2007 |
| WO | WO-2007/015232 A1 | 2/2007 |
| WO | WO-2007/015247 A2 | 2/2007 |
| WO | WO-2007/024038 A1 | 3/2007 |
| WO | WO-2007/041267 A2 | 4/2007 |
| WO | WO-2007/066339 A1 | 6/2007 |
| WO | WO-2007/080596 A2 | 7/2007 |
| WO | WO-2007/106170 A2 | 9/2007 |
| WO | WO-2008/019051 A2 | 2/2008 |
| WO | WO-2008/033873 A2 | 3/2008 |
| WO | WO-2008/052189 A2 | 5/2008 |
| WO | WO-2008/131302 A2 | 10/2008 |
| WO | WO-2009/040493 A1 | 4/2009 |
| WO | WO-2009/072108 A2 | 6/2009 |
| WO | WO-2009/072711 A2 | 6/2009 |
| WO | WO-2009/099988 A2 | 8/2009 |
| WO | WO-2009/137288 A2 | 11/2009 |
| WO | WO-2009/146053 A1 | 12/2009 |
| WO | WO-2009/146068 A1 | 12/2009 |
| WO | WO-2009/146072 A1 | 12/2009 |
| WO | WO-2010/027188 A2 | 3/2010 |
| WO | WO-2010/080014 A2 | 7/2010 |
| WO | WO-2010/095456 A1 | 8/2010 |
| WO | WO-2010/097790 A1 | 9/2010 |
| WO | WO-2011/006009 A1 | 1/2011 |
| WO | WO-2011/019859 A2 | 2/2011 |
| WO | WO-2011/075676 A2 | 6/2011 |
| WO | WO-2011/104875 A1 | 9/2011 |
| WO | WO-2011/123218 A1 | 10/2011 |
| WO | WO-2011/075676 A3 | 11/2011 |
| WO | WO-2011140497 A2 | 11/2011 |
| WO | WO-2012/052986 A2 | 4/2012 |
| WO | WO-2012/103483 A2 | 8/2012 |
| WO | WO-2012/103488 A1 | 8/2012 |
| WO | WO-2012/103492 A1 | 8/2012 |
| WO | WO-2012/119131 A1 | 9/2012 |
| WO | WO-2012/135828 A1 | 10/2012 |
| WO | WO-2013/013196 A1 | 1/2013 |

(56) References Cited

FOREIGN PATENT DOCUMENTS

| | | |
|---|---|---|
| WO | WO-2013/013199 A2 | 1/2013 |
| WO | WO-2013/104414 A1 | 7/2013 |
| WO | WO-2014/008470 A1 | 1/2014 |
| WO | WO-2014/008481 A1 | 1/2014 |
| WO | WO-2014/089488 A2 | 6/2014 |
| WO | WO-2014/130359 A1 | 8/2014 |
| WO | WO-2014/151104 A1 | 9/2014 |
| WO | WO-2014/179729 A1 | 11/2014 |
| WO | WO-2015/021434 A2 | 2/2015 |
| WO | WO-2015/051164 A2 | 4/2015 |
| WO | WO-2015/095675 A1 | 6/2015 |
| WO | WO-2015/126926 A1 | 8/2015 |
| WO | WO-2016/033584 A1 | 3/2016 |
| WO | WO-2016/033586 A1 | 3/2016 |
| WO | WO-2016/077759 A1 | 5/2016 |
| WO | WO-2016/127091 A1 | 8/2016 |
| WO | WO-2017/139773 A2 | 8/2017 |
| WO | WO-2017/172920 A1 | 10/2017 |
| WO | WO-2017/192723 A1 | 11/2017 |
| WO | WO-2018/057630 A1 | 3/2018 |
| WO | WO-2018/057637 A1 | 3/2018 |
| WO | WO-2020/097244 A1 | 5/2020 |

OTHER PUBLICATIONS

Banzhaf, C. et al., Spatiotemporal Closure of Fractional Laser-Ablated Channels Imaged by Optical Coherence Tomography and Reflectance Confocal Microscopy, Lasers in Surgery and Medicine, 48:157-165 (2016).
Bedi, V. et al., The effects of pulse energy variations on the dimensions of microscopic thermal treatment zones in nonablative fractional resurfacinq, Lasers Surg Med, 39(2):145-55 (2007).
Cevc, Gregor, Drug delivery across the skin, Expert Opinion Investigational Drugs, 6(12):1887-937 (1997).
Chang, Te-Sheng, An updated review of tyrosinase inhibitors, Int J Mol Sci, 10(6):2440-2475 (2009).
International Search Report for International Patent Application No. PCT/US2012/022980 dated Aug. 9, 2012.
International Written Opinion for International Patent Application No. PCT/US2012/022980 dated Aug. 9, 2012.
Czech, Z. et al., Pressure-sensitive adhesives for medical applications, Wide Spectra of Quality Control, Akyar, 309-332 (2011).
De las Heras Alarcon et al., Stimuli responsive polymers for biomedical applications, Chem Soc Rev. 34(3):276-85 (2005).
Dini, G. et al., Grasping leather plies by Bernoulli grippers, CIRP Ann Manuf Technol. 58(1):21-4 (2009).
Dujardin, J. et al., In vivo assessment of skin electroporation using sguare wave pulses, J Control Release, 79(1-3):219-27 (2002).
Dunkin, C. et al., Scarring occurs at a critical depth of skin injury: precise measurement in a graduated dermal scratch in human volunteers, Plast Reconstr Surg, 119(6):1722-32 (2007).
European Patent Office, Supplementary European Search Report, Application No. EP13813955.5, dated Mar. 18, 2016.
European Search Report for European Application No. 12739664.6 dated May 20, 2014.
Extended European Search Report, Application No. 12814711.3, dated Feb. 11, 2015.
Fernandes, J. et al., Micro-mechanical fractional skin rejuvenation, Plast Reconstr Surg, 130(5S-1):28 (2012).
Fernandes, J. et al., Micro-mechanical fractional skin rejuvenation, Plast Reconstr Surg, 131(2):216-23 (2013).
Galaev., 'Smart' polymers in biotechnology and medicine, Russ Chem Rev. 64(5):471-489 (1995).
Glogau, Aesthetic and anatomic analysis of the aging skin, Semin Cutan Med Surg. 15(3):134-8 (1996).
Hale, G. and Querry, M., Optical constants of water in the 200-nm to 200-microm wavelength region, Appl Opt, 12(3):555-63 (1973).
Han, H. et al., Combined, Minimally Invasive, Thread-based Facelift, Archives of Aesthetic Plastic Surgery, 20(3):160-164 (2014).

Huang, W.M. et al., Shape memory materials, Material Today, 13(7-8):54-61 (2010).
International Preliminary Report on Patentability for International Patent Application No. PCT/US2009/039125, dated Oct. 5, 2010 (6 pages).
International Preliminary Report on Patentability for International Patent Application No. PCT/US2012/022987, dated Jul. 30, 2013 (5 pages).
International Preliminary Report on Patentability for International Patent Application No. PCT/US2012/022993, dated Jul. 30, 2013 (5 pages).
International Preliminary Report on Patentability for International Patent Application No. PCT/US2012/047716, dated Nov. 4, 2014 (4 pages).
International Preliminary Report on Patentability for International Patent Application No. PCT/US2013/049445, dated Jan. 6, 2015 (4 pages).
International Preliminary Report on Patentability for International Patent Application No. PCT/US2014/036638, dated Nov. 3, 2015 (7 pages).
International Preliminary Report on Patentability for International Patent Application No. PCT/US2014/050426, dated Feb. 9, 2016 (8 pages).
International Search Report and Written Opinion for International Patent Application No. PCT/US2009/039125, dated Nov. 16, 2009 (9 pages).
International Search Report and Written Opinion for International Patent Application No. PCT/US2012/022987, dated Apr. 12, 2012 (6 pages).
International Search Report and Written Opinion for International Patent Application No. PCT/US2012/022993, dated May 17, 2012 (6 pages).
International Search Report and Written Opinion for International Patent Application No. PCT/US2012/047716, dated Oct. 25, 2012 (5 pages).
International Search Report and Written Opinion for International Patent Application No. PCT/US2013/049445, dated Oct. 18, 2013 (5 pages).
International Search Report and Written Opinion for International Patent Application No. PCT/US2014/016483, dated May 6, 2014 (9 pages).
International Search Report and Written Opinion for International Patent Application No. PCT/US2014/036638, dated Oct. 2, 2014 (10 pages).
International Search Report and Written Opinion for International Patent Application No. PCT/US2014/050426, dated Feb. 4, 2015 (11 pages).
International Search Report and Written Opinion for PCT/US2009/039125 dated Nov. 16, 2009.
International Search Report and Written Opinion for PCT/US2011/035613, dated May 6, 2011.
International Search Report and Written Opinion issued by the Korean Intellectual Property Office as International Searching Authority for International Application No. PCT/US2009/039114 dated Nov. 16, 2009 (10 pages).
International Search Report and Written Opinion dated Oct. 18, 2013 in connection with PCT/US2013/049445.
International Search Report for International Patent Application No. PCT/US2012/022987 dated Apr. 12, 2012.
International Search Report for International Patent Application No. PCT/US2012/022993 dated May 17, 2012.
International Search Report for International Patent Application No. PCT/US2012/047708.
International Search Report for PCT/US14/36638, 4 pages (dated Oct. 2, 2014).
International Search Report for PCT/US14/71443, 3 pages (dated Mar. 19, 2015).
International Search Report for PCT/US2014/016483, 3 pages (dated May 6, 2014).
International Search Report for PCT/US2015/060685, 3 pages (dated Feb. 2, 2016).
International Search Report for PCT/US2017/024752, 8 pages (dated Aug. 29, 2017).

(56) References Cited

OTHER PUBLICATIONS

International Search Report for PCT/US2017/052528 (Devices and Methods for Cosmetic Skin Resurfacing, filed Sep. 20, 2017), issued by ISA/US, 5 pages (dated Jan. 4, 2018).
International Search Report for PCT/US2017/052539 (Rapid Skin Treatment Using Microcoring, filed Sep. 20, 2017), issued by ISA/US, 7 pages (dated Nov. 22, 2017).
International Searching Report and Written Opinion issued by the Korean Intellectual Property Office as International Search Authority for International Application No. PCT/US2011/035613 dated Jan. 12, 2012 (6 pages).
International Written Opinion for International Patent Application No. PCT/US2012/022993 dated May 17, 2012.
International Written Opinion or International Patent Application No. PCT/US2012/022987 dated Apr. 12, 2012.
Kakasheva-Mazenkovska, L. et al., Variations of the histomorphological characteristics of human skin of different body regions in subjects of different age, Contributions, 32(2):119-28 (2011).
Konermann, W. et al., Ultrasonographically guided needle biopsy of benign and malignant soft tissue and bone tumors, J Ultrasound Med, 19(7):465-71 (2000).
Lemperle, G. et al., A Classification of Facial Wrinkles, Plastic and Reconstructive Surgery, 108(6):1735-1750 (2001).
Lien, T.K. and Davis, P.G.G., A novel gripper for limp materials based on lateral Coanda ejectors, CIRP Ann Manuf Technol, 57(1):33-6 (2008).
Majid, Imran, Microneedling therapy in atrophic facial scars: an objective assessment, J Cutan Aesthet Surg. 2(1):26-30 (2009).
Moore, J. et al., Modeling of the Plane Needle Cutting Edge Rake and Inclination Angles for Biopsy, Journal of Manufacturing Science and Engineering, 132:051005-1-051005-8 (2010).
Narins, R. et al., Validated Assessment Scales for the Lower Face, Dermatology Surgery, 38:333-342 (2012).
PCT International Preliminary Report on Patentability, PCT/US2014/036638, dated Nov. 3, 2015, 7 pages.
PCT International Preliminary Report on Patentability, PCT/US2014/050426, dated Feb. 9, 2016, 8 pages.
PCT International Search Report and Written Opinion, PCT/US2014/036638, dated Oct. 2, 2014, 10 pages.
PCT International Search Report and Written Opinion, PCT/US2014/050426, dated Feb. 4, 2015, 18 pages.
Pliquett, U. et al., A propagating heat wave model of skin electroporation, J Theor Biol, 251(2):195-201 (2008).
Prausnitz, M. et al., Electroporation of mammalian skin: a mechanism to enhance transdermal drug delivery, Proc Natl Acad Sci USA, 90(22):10504-8 (1993).
Salam, G. and Amin, J., The basic Z-plasty, Am Fam Physician, 67(11):2329-32 (2003).
Supplementary European Search Report issued by the European Patent Office for Application No. 11778450.4 dated Jan. 27, 2015 (5 pages).
Written Opinion for International Patent Application No. PCT/US2012/047708.
Written Opinion for PCT/US14/36638, 6 pages (dated Oct. 2, 2014).
Written Opinion for PCT/US14/71443, 4 pages (dated Mar. 19, 2015).
Written Opinion for PCT/US2014/016483, 6 pages (dated May 6, 2014).
Written Opinion for PCT/US2015/060685, 4 pages (dated Feb. 2, 2016).
Written Opinion for PCT/US2017/024752, 11 pages (dated Aug. 29, 2017).
Written Opinion for PCT/US2017/052528 (Devices and Methods for Cosmetic Skin Resurfacing, filed Sep. 20, 2017), issued by ISA/US, 17 pages (dated Jan. 4, 2018).
Written Opinon for PCT/US2017/052539 (Rapid Skin Treatment Using Microcoring, filed Sep. 20, 2017), issued by ISA/US, 8 pages (dated Nov. 22, 2017).
Zhu, J. et al., The Efficacy and Safety of Fractional CO2 Laser Combined with Topical Type A Botulinum Toxin for Facial Rejuvenation: A Randomized Controlled Split-Face Study, BioMed Research International, 7 pages (2016).
International Search Report for PCT/US2019/060131 (Systems and Methods for Skin Treatment, filed Nov. 6, 2019) received from ISA/EP, 5 pages (dated Mar. 27, 2020).
Written Opinion for PCT/US2019/060131 (Systems and Methods for Skin Treatment, filed Nov. 6, 2019) received from ISA/EP, 7 pages (dated Mar. 27, 2020).

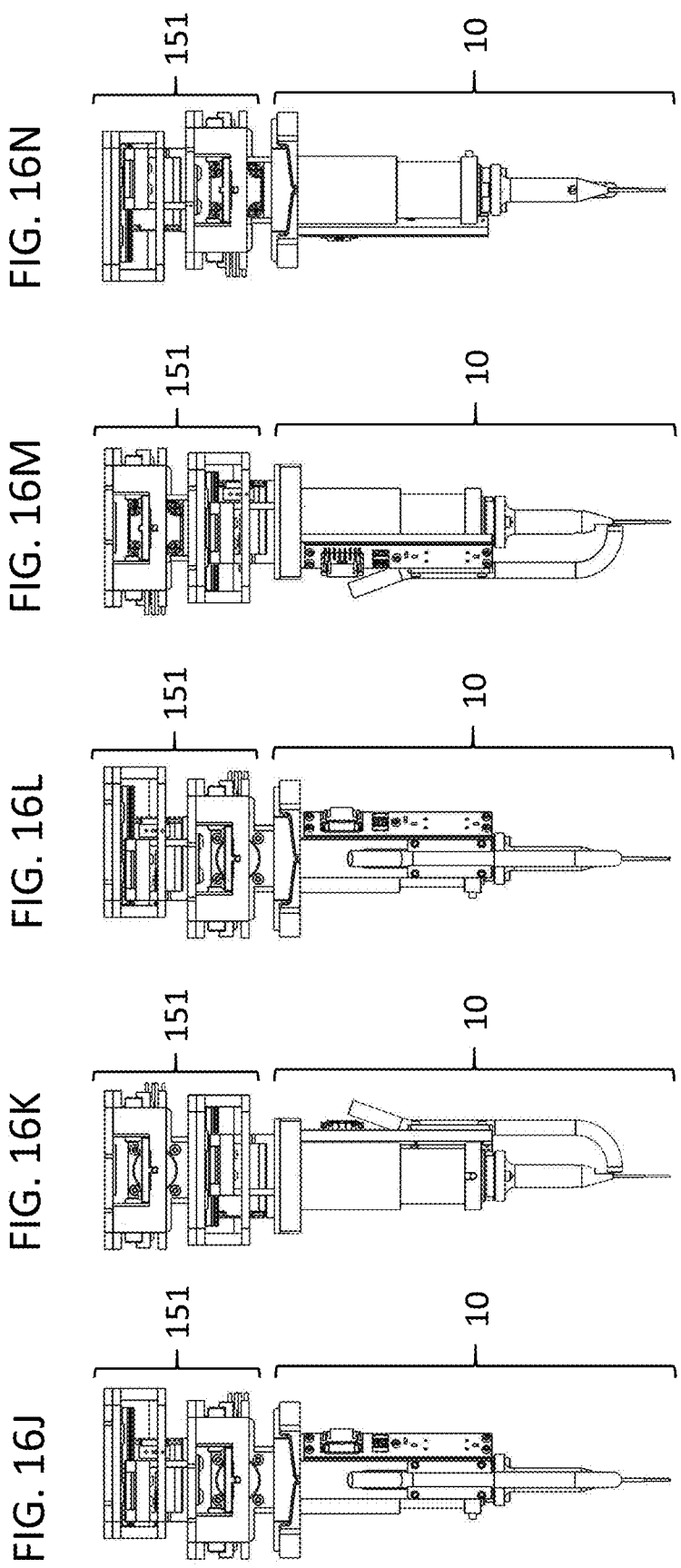

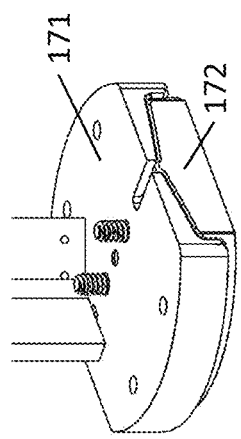
FIG. 17A
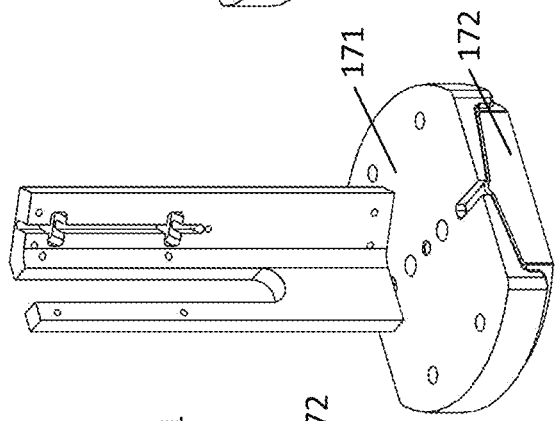
FIG. 17B
FIG. 17C
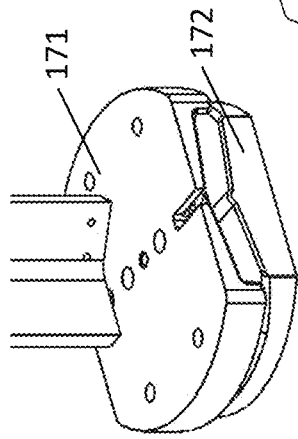
FIG. 17D
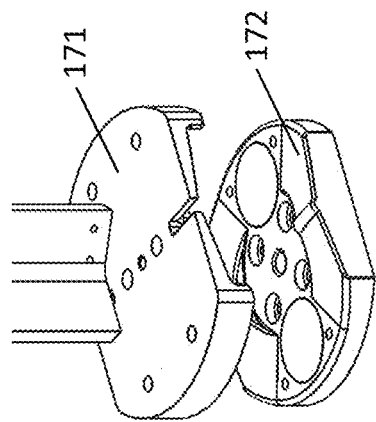

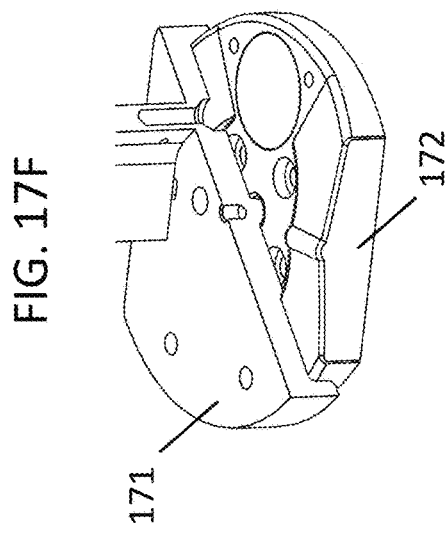
FIG. 17E
FIG. 17F
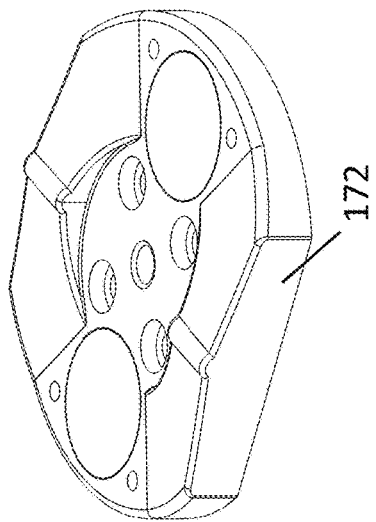
FIG. 17H
FIG. 17I
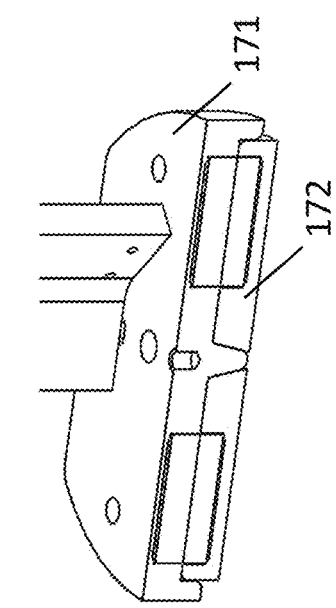
FIG. 17G

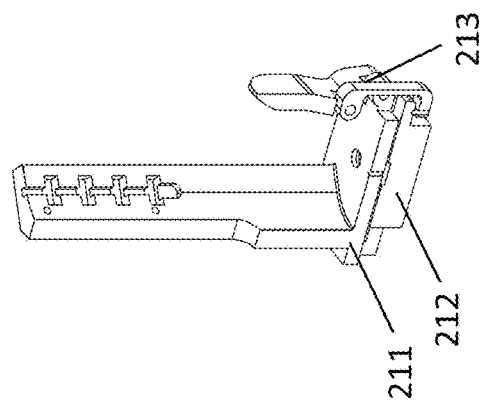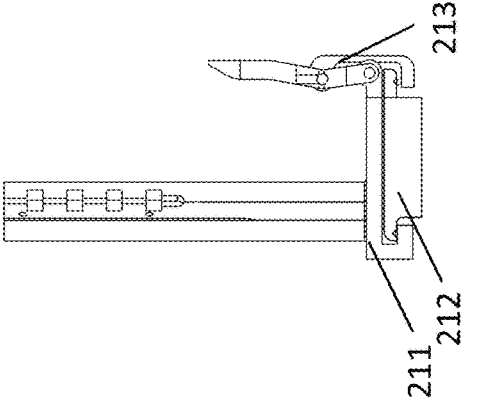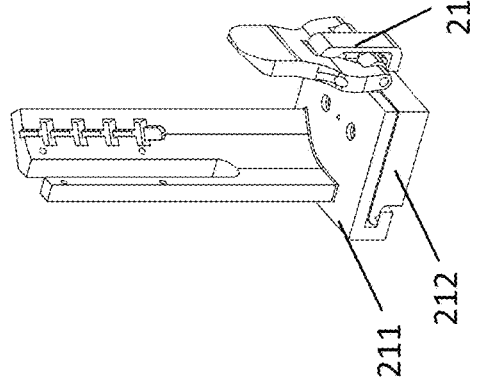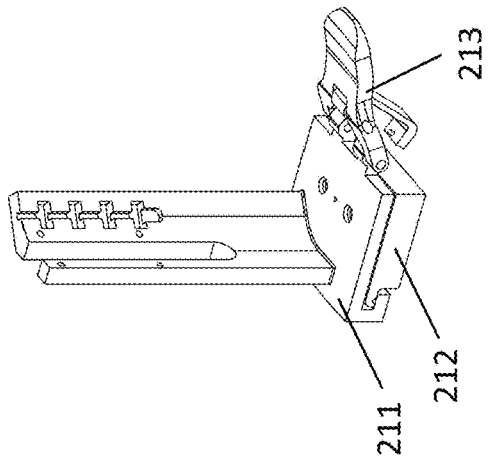

DEVICES AND METHODS FOR COSMETIC SKIN RESURFACING

CROSS REFERENCE TO RELATED APPLICATIONS

This application is a U.S. National Phase Application under 35 U.S.C. § 371 of International Patent Application No. PCT/US2017/024752, filed on Mar. 29, 2017, which claims priority to and the benefit of U.S. provisional application No. 62/314,748, filed Mar. 29, 2016, the entire contents of each of which are hereby incorporated by reference in their entireties.

BACKGROUND OF THE INVENTION

In aesthetic medicine, elimination of excess tissue and/or skin laxity is an important concern that affects more than 25% of the U.S. population. Conventional surgical therapies (e.g., a face lift, brow lift, or breast lift) can be effective but are invasive, inconvenient, and expensive, while scarring limits the applicability of surgery to certain treatment sites.

Although minimally invasive methods are available, such methods are generally less effective than surgical methods. For example, methods using energy sources (e.g., laser, non-coherent light, radiofrequency, and ultrasound) can be effective at improving the architecture and texture of the skin but are less effective at tightening the skin or reducing skin laxity. In addition, tissue ablative methods that create micro-ablations with photo-thermal energy can generate a coagulation zone in tissue that interferes with closure of the ablation zones, thereby inhibiting tissue tightening. These methods also require longer patient healing times due to the biological reparative response to coagulated and dead tissue during the remodeling process. Also, laser ablation depth is typically limited by the depth of the laser beam focus. Ablation of deeper tissue layers than is possible with available laser systems is desirable for the treatment of scars, for example.

Other methods, such as the use of neurotoxins, for example, botulinum toxin, reduce the formation of dynamic wrinkles by paralysis of the injected muscles, but such toxins have minimal or no direct effect on skin tightness or laxity. Finally, dermal fillers, such as hyaluronic acid, can be injected in the dermal layer to smooth out wrinkles and improve contours, but such fillers do not directly tighten or reduce laxity of the skin. Thus, surgical therapies remain the gold standard for lifting and/or tightening skin, as compared to energy-based techniques (e.g., laser, radiofrequency, and ultrasound) and injection-based techniques (e.g., botulinum toxin and fillers such as hyaluronic acid- and collagen-based fillers).

Accordingly, there is a need for improved methods and devices that provide increased effectiveness over currently available minimally-invasive techniques while maintaining convenience, affordability, and accessibility to patients desiring tissue restoration.

SUMMARY OF THE INVENTION

This invention relates to hollow needles, needle assemblies, actuation units, apparatuses, kits, and methods for cosmetic resurfacing of skin tissue by removing portions of the skin tissue. The invention features an apparatus for generating a cosmetic effect in the skin tissue that includes one or more hollow needles each having at least one prong. The apparatus may also include a mechanism for removing tissue portion(s) from the hollow needle(s).

In a first aspect, the invention features an apparatus for producing a cosmetic effect in a skin tissue that includes at least one hollow needle including at least a first prong provided at a distal end of the hollow needle, wherein an angle between a lateral side of the first prong and a longitudinal axis of the hollow needle is at least about 20 degrees, and wherein the hollow needle is configured to remove a portion of the skin tissue when the hollow needle is inserted into and withdrawn from the skin tissue.

In some embodiments of the first aspect of the invention, the angle between the lateral side of the first prong and the longitudinal axis of the hollow needle is between about 20 and about 40 degrees. In some embodiments, the angle between the lateral side of the first prong and the longitudinal axis of the hollow needle is about 30 degrees.

In some embodiments of the first aspect of the invention, the hollow needle further includes a second prong at the distal end of the hollow needle. In some embodiments, an angle between the lateral side of the second prong and the longitudinal axis of the hollow needle is at least about 20 degrees. In some embodiments, the angle between the lateral side of the second prong and the longitudinal axis of the hollow needle is between about 20 and about 40 degrees. In some embodiments, the lateral side of the second prong and the longitudinal axis of the hollow needle is about 30 degrees. In some embodiments, the angle between a lateral side of the second prong and a longitudinal axis of the hollow needle is less than about 20 degrees. In some embodiments, the angle between the lateral side of the second prong and the longitudinal axis of the hollow needle is between about 5 degrees and about 20 degrees.

In some embodiments, the first prong includes an edge. In some embodiments, each of the first and second prongs includes an edge.

In some embodiments, the first prong includes a flat tip. In some embodiments, each of the first and second prongs includes a flat tip. In some embodiments, the flat tip has a length and a width. In some embodiments, the length and/or the width is at an angle relative to the longitudinal axis of the hollow needle. In some embodiments, the length and/or the width is perpendicular to the longitudinal axis of the hollow needle.

In a second aspect, the invention features an apparatus for producing a cosmetic effect in a skin tissue that includes at least one hollow needle including at least a first prong provided at a distal end of the hollow needle, wherein the first prong includes a flat tip having at least two dimensions, and wherein the hollow needle is configured to remove a portion of the skin tissue when the hollow needle is inserted into and withdrawn from the skin tissue.

In some embodiments of the second aspect of the invention, the hollow needle further includes a second prong at the distal end of the hollow needle. In some embodiments, the second prong includes a flat tip.

In some embodiments, the flat tip has a length and a width. In some embodiments, the length and/or the width is at an angle relative to the longitudinal axis of the hollow needle. In some embodiments, the length and/or the width is perpendicular to the longitudinal axis of the hollow needle.

In some embodiments of the second aspect of the invention, an angle between a lateral side of the first prong and a longitudinal axis of the hollow needle is at least about 20 degrees. In some embodiments, the angle between the lateral side of the first prong and the longitudinal axis of the hollow needle is between about 20 and about 40 degrees. In some embodiments, the angle between the lateral side of the first prong and the longitudinal axis of the hollow needle is about 30 degrees. In some embodiments of the second aspect of the invention, an angle between a lateral side of the first prong and a longitudinal axis of the hollow needle is less than about 20 degrees. In some embodiments, the angle between the lateral side of the first prong and the longitudinal axis of the hollow needle is between about 5 degrees and about 20 degrees.

In some embodiments of the second aspect of the invention, an angle between the lateral side of the second prong and the longitudinal axis of the hollow needle is at least about 20 degrees. In some embodiments, the angle between the lateral side of the second prong and the longitudinal axis of the hollow needle is between about 20 and about 40 degrees. In some embodiments, the angle between the lateral side of the second prong and the longitudinal axis of the hollow needle is about 30 degrees. In some embodiments of the second aspect of the invention, an angle between a lateral side of the second prong and a longitudinal axis of the hollow needle is less than about 20 degrees. In some embodiments, the angle between the lateral side of the second prong and the longitudinal axis of the hollow needle is between about 5 degrees and about 20 degrees.

In some embodiments of the first and second aspects of the invention, the first prong of the hollow needle includes a tip micro-feature. In some embodiments, each of the first and second prongs of the hollow needle includes a tip micro-feature. In some embodiments, the tip micro-feature is a hole or a slit. In some embodiments, the slit is a rectangular-shaped slit, a square-shaped slit, a U-shaped slit, or a T-shaped slit. In some embodiments, the tip micro-feature intersects the inner wall of the hollow needle at a non-perpendicular angle.

In some embodiments of the first and second aspects of the invention, the apparatus includes a plurality of hollow needles. In some embodiments, the distance between adjacent hollow needles is about 15 mm or less.

In some embodiments of the first and second aspects of the invention, the hollow needle is treated with a coating. In some embodiments, the coating is selected from the group consisting of TiN, TiCN, TiAlN, ZrN, and a diamond-like carbon.

In some embodiments of the first and second aspects of the invention, the inner diameter of the hollow needle is between about 0.14 mm and 0.84 mm. In some embodiments, the inner diameter of the hollow needle is between about 0.24 mm and 0.40 mm.

In some embodiments of the first and second aspects of the invention, the gauge size of the hollow needle is between 18 and 30 gauge. In some embodiments, the gauge size of the hollow needle is between 22 and 25 gauge.

In some embodiments of the first and second aspects of the invention, the length of the hollow needle is between about 2 mm and about 5 mm.

In some embodiments of the first and second aspects of the invention, the hollow needle is configured to extend (i) into the dermal layer, (ii) through the entire dermal layer to the junction of the dermal layer and the subcutaneous fat layer, or (iii) into the subcutaneous fat layer.

In some embodiments of the first and second aspects of the invention, the apparatus is configured to remove an areal fraction of the skin tissue that is between about 0.01 to about 0.65. In some embodiments, the apparatus is configured to remove an areal fraction of the skin tissue that is between about 0.01 to about 0.05. In some embodiments, the apparatus is configured to remove an areal fraction of the skin tissue that is between about 0.02 to about 0.03 (e.g., about 0.025).

In some embodiments of the first and second aspects of the invention, the inner wall of the hollow needle has a surface roughness between about 150 and about 300 Rz.

In some embodiments of the first and second aspects of the invention, the hollow needle includes a lumen, wherein the apparatus further includes a tissue removal tool within the lumen of the hollow needle and wherein the tissue removal tool is configured to facilitate removal of portions of the skin tissue from the hollow needle. In some embodiments, the tissue removal tool is controllably translatable along the longitudinal axis of the hollow needle. In some embodiments, the tissue removal tool is a piston. In some embodiments, the piston includes a round tip at a distal end of the piston. In some embodiments, the portions of the skin tissue removed by the tissue removal tool from the lumen of the hollow needle are substantially intact tissue portions.

In some embodiments of the first and second aspects of the invention, the apparatus further includes an aspiration tube, wherein the aspiration tube is coupled to a low pressure source and a trap. In some embodiments, the aspiration tube is placed in close proximity to the distal end of the hollow needle and wherein the trap is configured to capture the portions of the skin tissue to be discarded. In some embodiments, the low pressure source is a vacuum pump.

In some embodiments of the first and second aspects of the invention, the apparatus further includes a low-pressure conduit coupled to the hollow needle, wherein the low-pressure conduit is connected to a low pressure source to generate suction in the hollow needle. In some embodiments, the low pressure source is a vacuum pump.

In some embodiments of the first and second aspects of the invention, the apparatus further includes at least one actuator. In some embodiments, the actuator: 1) is configured to displace the hollow needle back and forth along a direction substantially parallel to the axis of the hollow needle; and/or 2) is configured to translate the hollow needle over the skin tissue in one direction or two orthogonal directions. In some embodiments, the actuator is configured to displace the hollow needle back and forth along a direction substantially parallel to the axis of the hollow needle and to translate the hollow needle over the skin tissue in one direction or two orthogonal directions. In some embodiments, the actuator is coupled to the apparatus by a locking or connecting mechanism. In some embodiments, the locking or connecting mechanism is selected from the group consisting of a magnetic latch, a compression clamp, a sliding clamp, a rotating lock, a clasp latch, and a sliding-rotating lock.

In some embodiments of the first and second aspects of the invention, the apparatus further includes a cover. In some embodiments, the cover is coupled to the actuator by a locking or connecting mechanism. In some embodiments, the locking or connecting mechanism is selected from the group consisting of a magnetic latch, a compression clamp, a sliding clamp, a rotating lock, a clasp latch, and a sliding-rotating lock.

In some embodiments of the first and second aspects of the invention, the apparatus further includes a spacer. In some embodiments, the spacer is attached to the cover, positioned between the cover and the skin tissue, and/or configured to control the depth of insertion of the hollow needle.

In some embodiments of the first and second aspects of the invention, the apparatus is configured to produce an array pattern upon removal of the portions of the skin tissue. In some embodiments, the array pattern includes one or more rows or a semi-random spatial distribution.

In some embodiments of the first and second aspects of the invention, the hollow needle is repeatedly inserted into and withdrawn from the skin tissue.

In some embodiments of the first and second aspects of the invention, the first and/or second prong as described herein is resistant to curling.

In a third aspect, the invention features a method for producing a cosmetic effect in a skin tissue. The method includes producing a plurality of holes in the skin tissue using an apparatus described herein, wherein each hole is produced by removing a portion of the skin tissue.

In some embodiments of the third aspect of the invention, the diameter of each hole is between about 0.14 mm and 0.84 mm. In some embodiments, the diameter of each hole is between about 0.24 mm and 0.40 mm.

In some embodiments of the third aspect of the invention, a surface area fraction of the removed portions of the skin tissue is between about 0.01 to about 0.65. In some embodiments, the surface area fraction of the removed portions of the skin tissue is less than about 0.1, such as between about 0.01 to about 0.05. In some embodiments, the surface area fraction of the removed portions of the skin tissue is between about 0.02 to about 0.03 (e.g., 0.025).

In some embodiments of the third aspect of the invention, at least one of the holes extends (i) into the dermal layer, (ii) through the entire dermal layer to the junction of the dermal layer and the subcutaneous fat layer, or (iii) into the subcutaneous fat layer. In some embodiments, at least one of the holes extends to a depth of between about 2 mm and about 5 mm.

In some embodiments of the third aspect of the invention, an array pattern including one or more rows or a semi-random spatial distribution is generated by the plurality of holes.

In a fourth aspect, the invention provides a hollow needle including at least a first prong provided at a distal end of the hollow needle, wherein an angle ($\alpha$) between a lateral side of the first prong and a longitudinal axis of the hollow needle is at least about 20 degrees, and wherein the hollow needle is configured to remove a portion of skin tissue when the hollow needle is inserted into and withdrawn from skin tissue.

In some embodiments of the fourth aspect of the invention, the angle ($\alpha$) between the lateral side of the first prong and the longitudinal axis of the hollow needle is between about 20 and about 40 degrees. In some embodiments, the angle ($\alpha$) between the lateral side of the first prong and the longitudinal axis of the hollow needle is about 30 degrees.

In some embodiments of the fourth aspect of the invention, the hollow needle further includes a second prong. In some embodiments, an angle ($\alpha$) between a lateral side of the second prong and a longitudinal axis of the hollow needle is at least about 20 degrees. In some embodiments, the angle ($\alpha$) between the lateral side of the second prong and the longitudinal axis of the hollow needle is between about 20 and about 40 degrees. In some embodiments, the angle ($\alpha$) between the lateral side of the second prong and the longitudinal axis of the hollow needle is about 30 degrees. In some embodiments of the fourth aspect of the invention, an angle ($\alpha$) between a lateral side of the second prong and a longitudinal axis of the hollow needle is less than about 20 degrees. In some embodiments, the angle ($\alpha$) between the lateral side of the second prong and the longitudinal axis of the hollow needle is between about 5 degrees and about 20 degrees.

In some embodiments of the fourth aspect of the invention, the first prong includes an edge. In some embodiments, each of the first and second prongs includes an edge.

In some embodiments of the fourth aspect of the invention, the first prong includes a flat tip. In some embodiments, each of the first and second prongs includes a flat tip. In some embodiments, the flat tip has a length and a width. In some embodiments, the length and/or the width is at an angle relative to the longitudinal axis of the hollow needle. In some embodiments, the length and/or the width is perpendicular to the longitudinal axis of the hollow needle.

In a fifth aspect, the invention provides a hollow needle including at least a first prong provided at a distal end of the hollow needle, wherein the first prong includes a flat tip having at least two dimensions, and wherein the hollow needle is configured to remove a portion of skin tissue when the hollow needle is inserted into and withdrawn from skin tissue.

In some embodiments of the fifth aspect of the invention, the hollow needle further includes a second prong. In some embodiments, the second prong includes a flat tip. In some embodiments, the flat tip has a length and a width. In some embodiments, the length and/or the width is at an angle relative to the longitudinal axis of the hollow needle. In some embodiments, the length and/or the width is perpendicular to the longitudinal axis of the hollow needle.

In some embodiments of the fifth aspect of the invention, an angle ($\alpha$) between a lateral side of the first prong and a longitudinal axis of the hollow needle is at least about 20 degrees. In some embodiments, the angle ($\alpha$) between the lateral side of the first prong and the longitudinal axis of the hollow needle is between about 20 and about 40 degrees. In some embodiments, the angle ($\alpha$) between the lateral side of the first prong and the longitudinal axis of the hollow needle is about 30 degrees. In some embodiments of the fifth aspect of the invention, an angle ($\alpha$) between a lateral side of the first prong and a longitudinal axis of the hollow needle is less than about 20 degrees. In some embodiments, the angle ($\alpha$) between the lateral side of the first prong and the longitudinal axis of the hollow needle is between about 5 degrees and about 20 degrees.

In some embodiments of the fifth aspect of the invention, an angle ($\alpha$) between a lateral side of the second prong and a longitudinal axis of the hollow needle is at least about 20 degrees. In some embodiments, the angle ($\alpha$) between the lateral side of the second prong and the longitudinal axis of the hollow needle is between about 20 and about 40 degrees. In some embodiments, the angle ($\alpha$) between the lateral side of the second prong and the longitudinal axis of the hollow needle is about 30 degrees. In some embodiments of the fifth aspect of the invention, an angle ($\alpha$) between a lateral side of the second prong and a longitudinal axis of the hollow needle is less than about 20 degrees. In some embodiments, the angle ($\alpha$) between the lateral side of the second prong and the longitudinal axis of the hollow needle is between about 5 degrees and about 20 degrees.

In some embodiments of the fifth aspect of the invention, the first prong of the hollow needle includes a tip micro-feature. In some embodiments, each of the first and second prongs of the hollow needle includes a tip micro-feature. In some embodiments, the tip micro-feature is a hole or a slit. In some embodiments, the slit is a rectangular-shaped slit, a square-shaped slit, a U-shaped slit, or a T-shaped slit. In some embodiments, the tip micro-feature intersects the inner wall of the hollow needle at a non-perpendicular angle.

In some embodiments of the fourth and fifth aspects of the invention, the hollow needle is treated with a coating. In some embodiments, the coating is selected from the group consisting of TiN, TiCN, TiAlN, ZrN, and a diamond-like carbon.

In some embodiments of the fourth and fifth aspects of the invention, the hollow needle is repeatedly inserted into and withdrawn from the skin tissue.

In a sixth aspect, the invention features a needle assembly including a hollow needle, a z-actuator, and a tissue removal tool, wherein the hollow needle includes at least a first prong provided at a distal end of the hollow needle and wherein an angle ($\alpha$) between a lateral side of the first prong and a longitudinal axis of the hollow needle is at least about 20 degrees.

In some embodiments of the sixth aspect of the invention, the hollow needle further includes a second prong. In some embodiments, an angle ($\alpha$) between a lateral side of the second prong and a longitudinal axis of the hollow needle is at least about 20 degrees. In some embodiments, an angle ($\alpha$) between a lateral side of the second prong and a longitudinal axis of the hollow needle is less than about 20 degrees.

In some embodiments of the sixth aspect, the first prong includes an edge. In some embodiments, each of the first and second prongs includes an edge. In some embodiments, the first prong includes a flat tip. In some embodiments, each of the first and second prongs includes a flat tip. In some embodiments, the flat tip has a length and a width. In some embodiments, the length and/or the width is at an angle relative to the longitudinal axis of the hollow needle. In some embodiments, the length and/or the width is perpendicular to the longitudinal axis of the hollow needle.

In some embodiments, the needle assembly of the sixth aspect of the invention further includes a support base, a scaffold, an aspiration tube, a trap, and/or a pressure generating source. In some embodiments, the needle assembly is configured to be detachably attached to an x- and/or y-actuator.

In a seventh aspect, the invention features a needle assembly including a hollow needle, a z-actuator, and a tissue removal tool, wherein the hollow needle includes at least a first prong provided at a distal end of the hollow needle and wherein the first prong includes a flat tip having at least two dimensions.

In some embodiments of the seventh aspect, the hollow needle further includes a second prong. In some embodiments, the second prong includes a flat tip. In some embodiments, the flat tip has a length and a width. In some embodiments, the length and/or the width is at an angle relative to the longitudinal axis of the hollow needle. In some embodiments, the length and/or the width is perpendicular to the longitudinal axis of the hollow needle.

In some embodiments of the seventh aspect, an angle ($\alpha$) between a lateral side of the first prong and a longitudinal axis of the hollow needle is at least about 20 degrees. In some embodiments, an angle (a) between a lateral side of the first prong and a longitudinal axis of the hollow needle is less than about 20 degrees. In some embodiments of the seventh aspect, an angle ($\alpha$) between a lateral side of the second prong and a longitudinal axis of the hollow needle is at least about 20 degrees. In some embodiments, an angle ($\alpha$) between a lateral side of the second prong and a longitudinal axis of the hollow needle is less than about 20 degrees.

In some embodiments, the needle assembly of the seventh aspect of the invention further includes a support base, a scaffold, an aspiration tube, a trap, and/or a pressure generating source. In some embodiments, the needle assembly is configured to be detachably attached to an x- and/or y-actuator.

Definitions

By "tissue portion" is meant that portion of skin and/or proximal tissue layers (e.g., epidermal layer, dermal layer, and subcutaneous fat layer) that is removed (e.g., as a plug) by a hollow needle of the apparatus. A tissue portion may have particular dimensions, geometry, and other characteristics that correspond to the particular dimensions, geometry, and other characteristics of a hollow needle of the apparatus of the invention.

By removal of a tissue portion that is "substantially intact" is meant that the tissue portion that is removed from the lumen of a hollow needle remains as an unbroken or whole tissue portion, i.e., the removed tissue portion has not been broken or separated into individual, smaller pieces or macerated.

By "about" is meant +/−10% of the recited value.

By "subject" is meant a mammal (e.g., a human or non-human mammal).

By "proximal" or "proximal end" is meant the end of the hollow needle that is away from or opposite the needle tip, e.g., the end of hollow needle 14 that is closer to z-actuator 12 and support base 11, as shown in FIGS. 1A-1F.

By "distal" or "distal end" is meant the end of the hollow needle that is at or close to the needle tip (e.g., needle tip 18 of FIGS. 1A-1F).

By "coring rate" is meant the percentage of hollow needle actuations that result in cored tissue removal from the treatment area out of the total number of hollow needle actuations. The hollow needles of the invention are designed to maximize coring rate and minimize hollow needle actuations that do not result in cored tissue removal. A tissue portion detaches from the skin when the coring force exceeds the tissue resistance force. The tissue resistance force is determined by the connection of the tissue portion to its surrounding tissue. For example, when the hollow needle is fully inserted through the dermal layer of the skin, the tissue resistance force is determined by the connection between the tissue portion in the lumen of the needle and the subcutaneous fat layer. The coring rate is determined by, e.g., the coring force of the hollow needle, the friction between the lumen wall of the hollow needle and the tissue portion, and the tissue resistance force. The coring rate may also be affected by applying a pressure differential across the hollow needle. For example, a vacuum applied at the proximal end of the hollow needle may aspirate the cored tissue portion from the hollow needle, thereby, increasing the coring rate.

By "coring force" is meant the force applied by the hollow needle of the apparatus to the cored tissue portion as the needle is being withdrawn from the skin. The coring force is determined by, e.g., the friction between the lumen wall of the hollow needle and the cored tissue portion as the needle is being withdrawn from the skin and the position, geometry, and orientation of micro-features in the hollow needle.

By "insertion force" is meant the force generated by the hollow needle on the skin as it is inserted into the skin. The insertion force is initially determined by the amount of force required to penetrate the tissue. Once the tissue is penetrated, the insertion force is determine by the friction between the needle walls (inner and outer) and the surrounding tissue, as well as the force required to separate the tissue at the tip of the needle.

Other features and advantages of the invention will be apparent from the following Detailed Description and the claims.

DESCRIPTION OF THE DRAWINGS

FIG. 6A is a photograph showing the micro-feature as an oval-shaped hole at the needle tip and FIG. 6B is a photograph showing the micro-feature as a rectangular-shaped slit at the needle tip.

FIG. 8A is a photograph of a DLC-coated needle before undergoing any actuation cycles; FIG. 8B is a photograph of the DLC-coated needle after undergoing 5,000 actuation cycles; FIG. 8C is a photograph of the DLC-coated needle after undergoing 10,000 actuation cycles; and FIG. 8D is a photograph of a non-coated needle after undergoing 10,000 actuation cycles.

FIG. 14A shows a "zero" spacer that allows a 10 mm extension of a hollow needle and FIG. 14B shows a "2 mm" spacer that allows an 8 mm extension of a hollow needle. The extension lengths shown are exemplary only and are not meant to be limiting.

FIGS. 16J, 16K, 16L, 16M, 16N, 16O, 16P, and 16Q are schematic illustrations showing eight views of the inside of an apparatus of the invention including a needle assembly and an actuation unit.

FIGS. 17A, 17B, 17C, and 17D are schematic illustrations showing four views of a magnetic latch having parts 171 and 172.

FIGS. 17E and 17F are schematic illustrations showing two cross-sectional views of a magnetic latch having parts 171 and 172.

FIG. 17G is a schematic illustration showing part 171 of a magnetic latch.

FIGS. 17H and 17I are schematic illustrations showing part 172 of a magnetic latch.

FIGS. 21A, 21B, 21C, and 21D are schematic illustrations showing four views of a clasp latch having parts 211 and 212.

DETAILED DESCRIPTION OF THE INVENTION

Figure 1A:
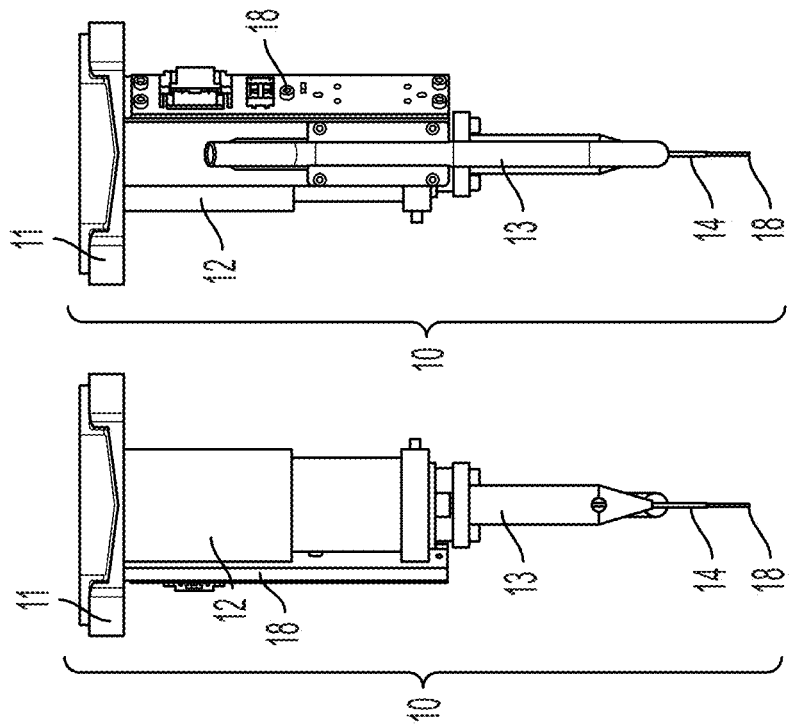
FIGS. 1A, 1B, and 1C are schematic illustrations showing three perspective views of a needle assembly of the invention.
Figure 1B:
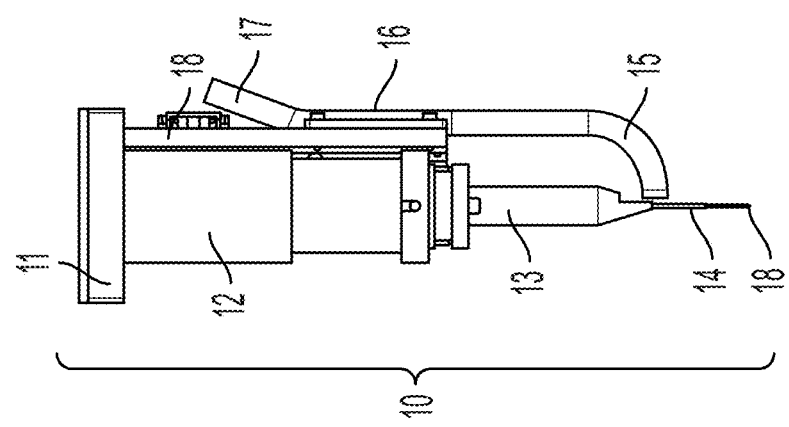
Figures 1C, 1D:
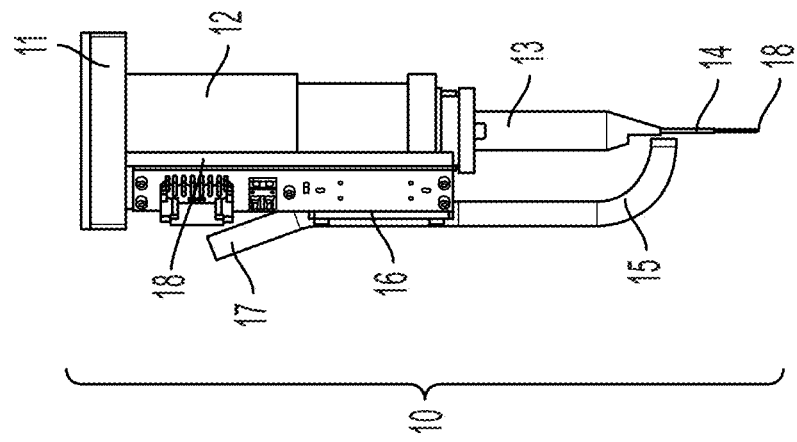
FIG. 1D is a schematic illustration showing a cross-sectional view of a needle assembly of the invention.
Figure 1F:
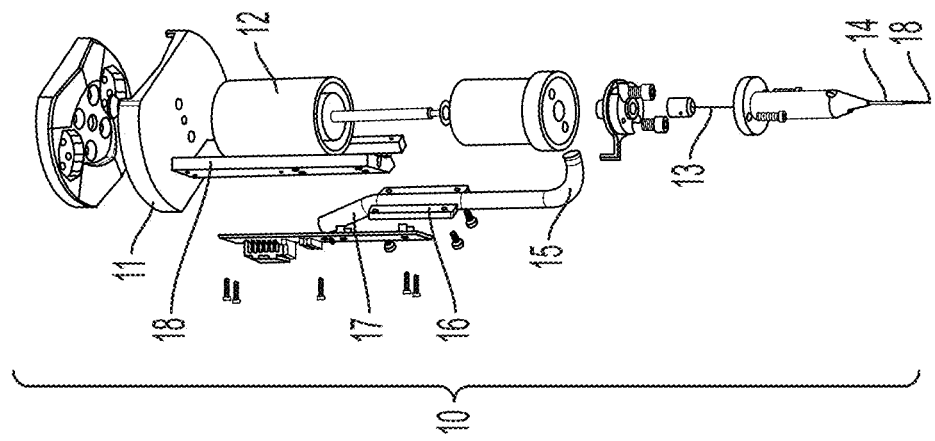
FIGS. 1E and 1F are exploded views showing individual components of a needle assembly of the invention.
Figure 1E:
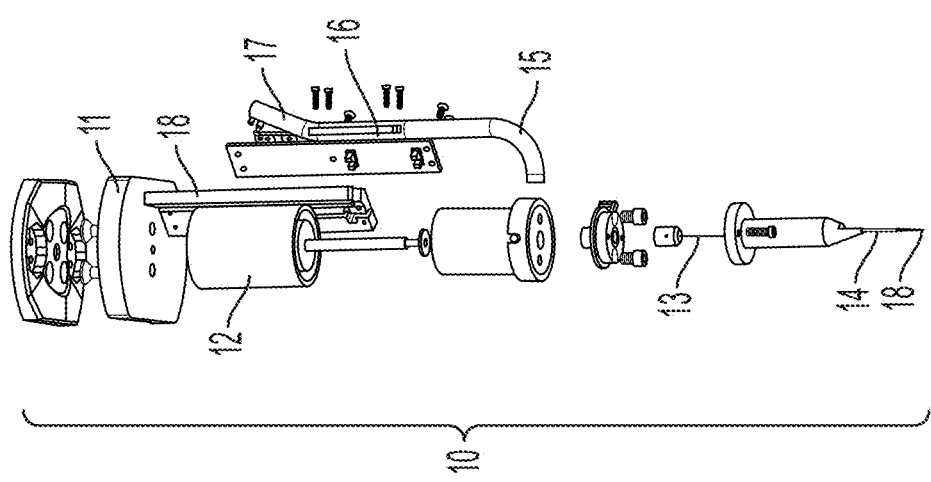

This invention relates to hollow needles, needle assemblies, actuation units, apparatuses, kits, and methods for generating a cosmetic effect in the skin (e.g., eliminating tissue volume, tightening skin, and/or reducing skin laxity) by removing tissue portions from the skin. Without being bound by theory, this approach facilitates skin remodeling by debulking the skin tissue and by triggering biological responses that contribute to tissue resurfacing and remodeling. In particular, the invention relates to hollow needles, as well as related needle assemblies, apparatuses, kits, and methods, capable of coring tissue portions by capturing and retaining the tissue portions inside the lumen of the hollow needle after insertion into and withdrawal from the skin. The cored tissue portions can be removed from the lumen of the hollow needle and discarded. The process can be repeated to generate multiple cored skin tissue portions, in particular over a desired area of skin and located at chosen sites of the body of a subject. The hollow needles, needle assemblies, actuation units, apparatuses, kits, and methods described herein provide increased effectiveness over currently available apparatuses and techniques while maintaining convenience, affordability, and accessibility to patients desiring tissue restoration.

Needles

The apparatus of the invention includes at least one hollow needle having at least a first prong. In some embodiments, an angle between a lateral side of the prong and a longitudinal axis of the hollow needle (e.g., a bevel angle α) is at least about 20 degrees (e.g., the bevel angle α may be greater than about 20 degrees, such as greater than 20 degrees, 22 degrees, 24 degrees, 26 degrees, 28 degrees, 30 degrees, 32 degrees, 34 degrees, 36 degrees, 38 degrees, and 40 degrees, or at an angle of about 20 to about 40 degrees, between 20 to 40 degrees, 20 to 38 degrees, 20 to 36 degrees, 20 to 34 degrees, 20 to 32 degrees, 20 to 30 degrees, 20 to 28 degrees, 20 to 26 degrees, 20 to 24 degrees, 20 to 22 degrees, 22 to 40 degrees, 24 to 40 degrees, 26 to 40 degrees, 28 to 40 degrees, 30 to 40 degrees, 32 to 40 degrees, 34 to 40 degrees, 36 to 40 degrees, and 38 to 40 degrees). In particular, an angle between a lateral side of the prong and a longitudinal axis of the hollow needle (e.g., a bevel angle α) is about 30 degrees.

In some embodiments, the tip of the prong of the hollow needle is an edge. In some embodiments, the tip of the prong of the hollow needle is a flat tip having at least two dimensions. In some embodiments, the prong of the hollow needle includes a tip micro-feature. The hollow needles of the invention are constructed to prevent frequent needle damage during use, such as needle tip curling and wear (e.g., becoming dull), needle heel degradation, and needle bending. The hollow needles of the invention are designed to maintain mechanical integrity and durability over a large number of actuation cycles (e.g., actuation cycles greater than 1,000, 2,000, 3,000, 4,000, 5,000, 6,000, 7,000, 8,000, 9,000, 1,0000, 11,000, 12,000, 13,000, 14,000, 15,000, or 20,000). Preferably, these needles also effectively remove tissue portions from the skin with high coring rate. To produce a cosmetic effect in the skin tissue, a hollow needle of the apparatus is inserted into the skin tissue, preferably to a pre-determined depth using a pre-determined force, such that the hollow needle removes a portion of the skin tissue by capturing the portion of the skin tissue in the lumen of the hollow needle.

Prongs

Figure 2:
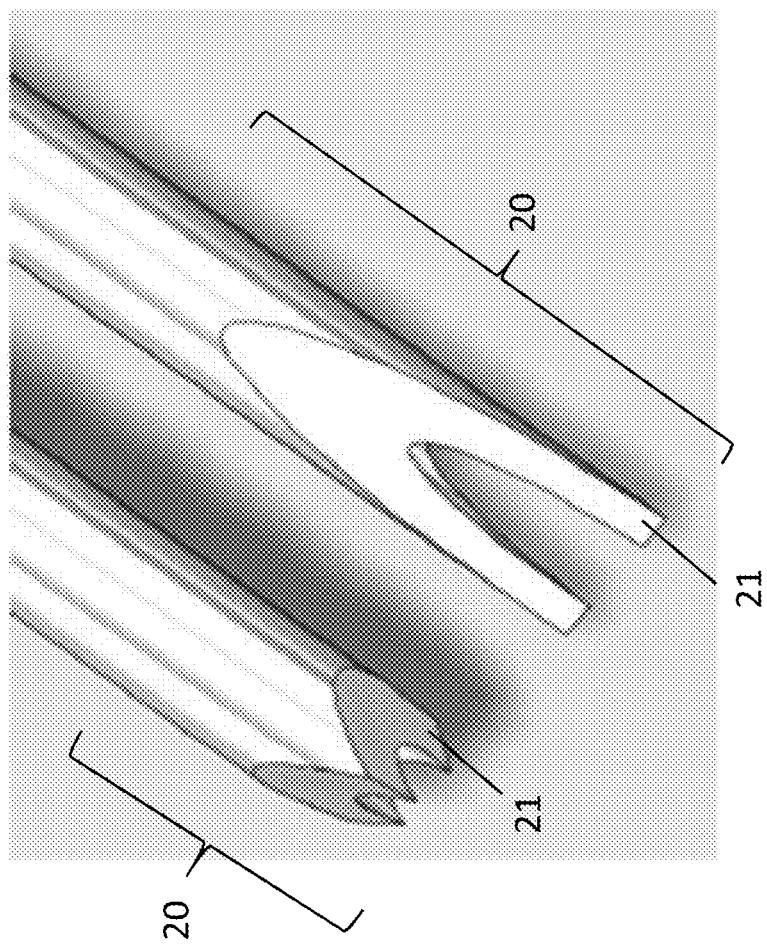
FIG. 2 is a schematic illustration showing possible needle prong configurations for a hollow needle.

As shown in FIG. 2, distal end 20 of the hollow needle of the apparatus (e.g., the end of the needle that penetrates the skin tissue) can be shaped to form one or more prongs 21. The hollow needle of the apparatus may have one prong at the distal end, two prongs, or more than two prongs (e.g., three, four, five, or six prongs). A hollow needle having one prong may be formed by grinding one side of the distal end of the hollow needle at an angle relative to the longitudinal axis of the hollow needle. A hollow needle having two prongs may be formed by grinding opposite sides of the distal end of the hollow needle at an angle relative to the longitudinal axis of the hollow needle.

Figure 3:
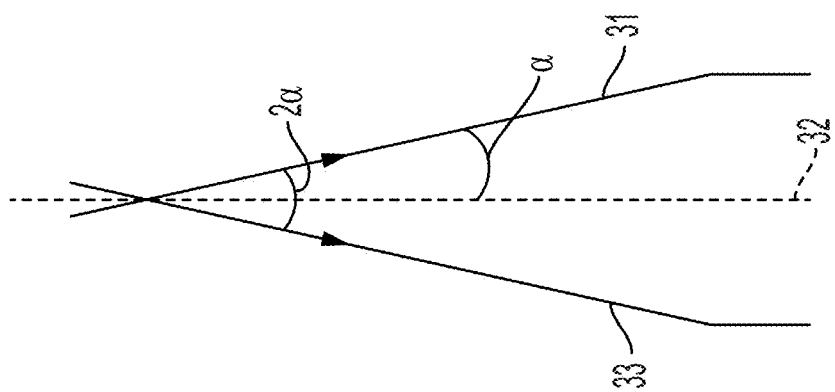
FIG. 3 is a schematic illustration showing a side view of a prong of a hollow needle. A bevel angle α of a prong refers to the angle between lateral side 31 of the prong and longitudinal axis 32 of the hollow needle.

The geometry of a prong at the distal end of a hollow needle can be characterized by a bevel angle. A bevel angle, e.g., angle α as shown in FIG. 3, refers to the angle between lateral side 31 of the prong and longitudinal axis 32 of the hollow needle. An angle of "2α" refers to the angle between two lateral sides of the prong of the hollow needle, e.g., the angle between lateral side 31 and lateral side 33 of the hollow needle. A bevel angle α between a lateral side of a prong and a longitudinal axis of the hollow needle may be at least about 20 degrees (e.g., between about 20 and about 40 degrees (e.g., 20, 22, 24, 26, 28, 30, 32, 34, 36, 38, or 40 degrees)). In particular, an angle between a lateral side of a prong and a longitudinal axis of the hollow needle may be about 30 degrees. For hollow needles having two or more prongs (e.g., FIG. 2), each prong may have the same bevel angle or different bevel angles. In one embodiment, for a hollow needle having two prongs, e.g., a first prong and a second prong, an angle between a lateral side of the first prong and a longitudinal axis of the hollow needle may be between about 20 and about 30 degrees (e.g., 20, 22, 24, 26, 28, or 30 degrees) and an angle between a lateral side of the second prong and a longitudinal axis of the hollow needle may be between about 30 and about 40 degrees (e.g., 30, 32, 34, 36, 38, or 30 degrees). For example, the first prong may have a bevel angle α of 20 degrees and the second prong may have a bevel angle α of 30 degrees.

A bevel angle α of at least about 20 degrees or more improves the mechanical integrity of the needle over several actuation cycles of insertion and withdrawal into skin tissue. Table 1 below shows that a two-prong hollow needle having a 2α bevel angle of 40 degrees (the bevel angle α of each prong is 20 degrees) reduces the occurrence of needle tip curling relative to a two-prong hollow needle having a 2α bevel angle of 20 degrees (the bevel angle α of each prong is 10 degrees). A total of 5 two-prong hollow needles each having a bevel angle α of 10° and 5 two-prong hollow needles each having a bevel angle α of 20° were tested.

TABLE 1

| | Number of Needles showing Tip Curling | |
|---|---|---|
| Number of Actuation Cycles | 10° Bevel Angle α | 20° Bevel Angle α |
| 5,000 | 1 | 0 |
| 10,000 | 2 | 0 |
| 15,000 | 2 | 0 |
| 20,000 | 3 | 1 |

Figure 4:
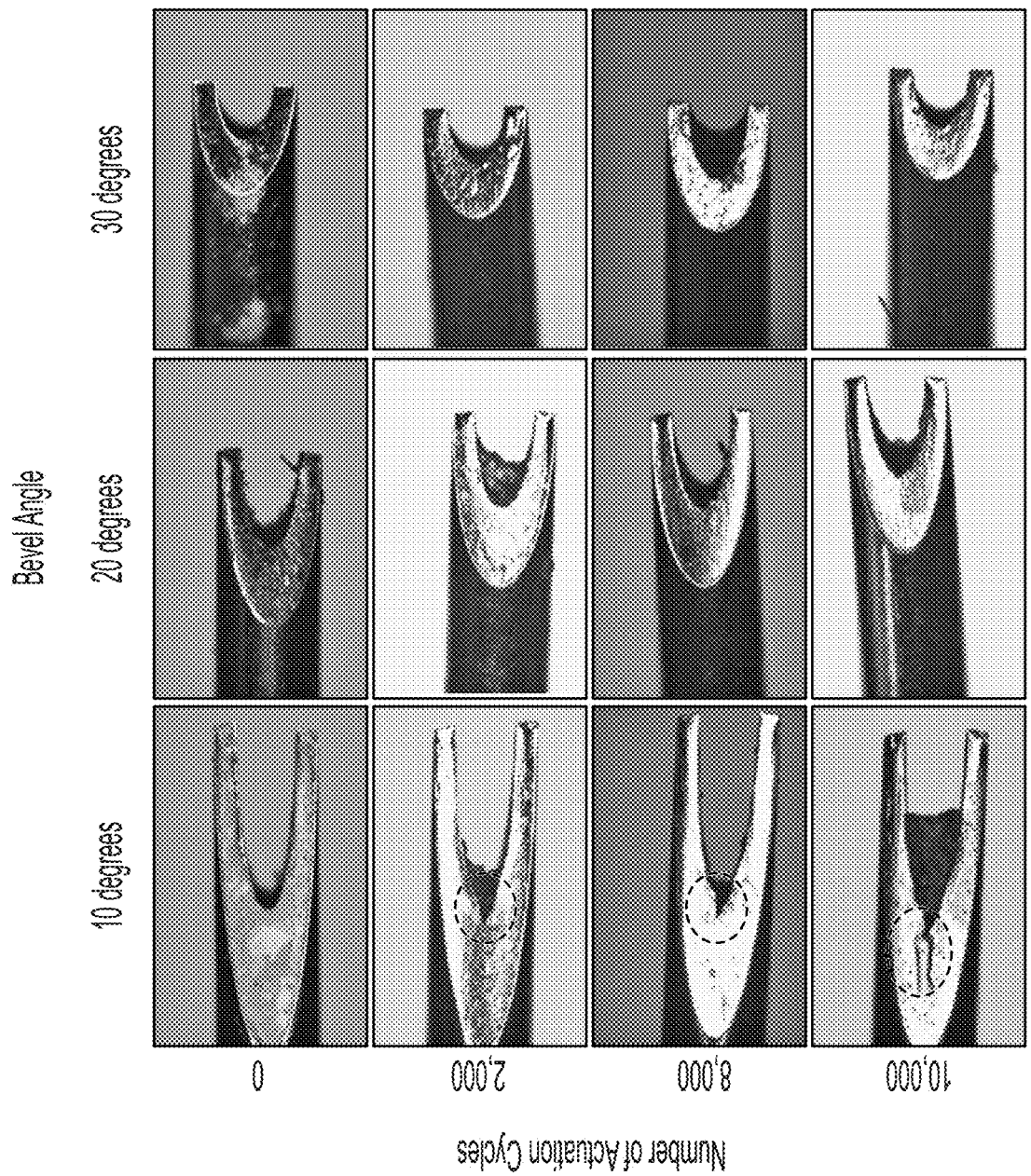
FIG. 4 shows photographs that compare needle heel degradations after 2,000, 8,000, and 10,000 actuation cycles of hollow needles having a bevel angle of 10 degrees, 20 degrees, or 30 degrees.

Additionally, FIG. 4 shows that increasing the needle bevel angle α of a prong also reduces the occurrence of needle heel degradation over a large number of actuation cycles. As show in FIG. 4, a hollow needle having a bevel angle α of 10 degrees displayed signs of needle heel degradation (indicated by dashed circles) before 2,000 actuation cycles, while a hollow needle having a bevel angle α of 20 degrees and a hollow needle having a bevel angle α of 30 degrees showed no apparent sign of needle heel degradation over 10,000 actuation cycles.

Figure 5A:
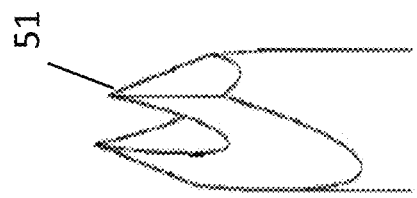
FIGS. 5A, 5B, and 5C are schematic illustrations showing a hollow needle with two prongs each having a sharp point at the tip of the prong, a hollow needle with two prongs each having an edge at the tip of the prong, and a hollow needle with two prongs each having a flat tip, respectively.
Figure 5B:
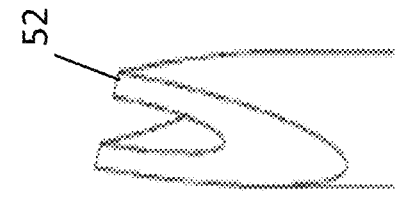
Figure 5C:
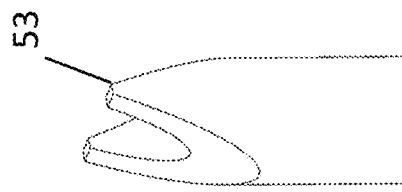

The tip of a prong of a hollow needle may be of varying geometries. For example, the tip of a prong may have a sharp point (e.g., sharp point 51 as shown in FIG. 5A) or an edge (e.g., a one-dimensional edge) (e.g., edge 52 as shown in FIG. 5B). For a prong having an edge at the tip, each of the bevel angles of the prong may be at least about 20 degrees (e.g., from about 20 to about 40 degrees (e.g., about 30 degrees)). For a hollow needle having two or more prongs, e.g., two prongs, the prongs may have different bevel angles (e.g., a bevel angle α of about 20 degrees at the first prong and a bevel angle α of about 30 degrees at the second prong). The tip of a prong may be a flat tip (e.g., a flat tip having two dimensions) (e.g., flat tip 53 as shown in FIG. 5C). For example, a flat tip has a length and a width. The surface (length/width) of the flat tip of the prong may be at an angle relative to the longitudinal axis of the hollow needle. For example, the surface of the flat tip may be perpendicular to the longitudinal axis of the hollow needle (e.g., at a 90 degree angle relative to the longitudinal axis of the hollow needle) or the surface of the flat tip may be at a non-90 degree angle relative to the longitudinal axis of the hollow needle (e.g., between about 3 to about 89 degrees, such as 3 to 89 degrees, e.g., 3, 6, 9, 12, 15, 18, 21, 24, 27, 30, 33, 36, 39, 42, 45, 48, 51, 54, 57, 60, 63, 66, 69, 72, 75, 78, 81, 84, 87, and 89 degrees). The surface of the flat tip may be level or may have different geometry, e.g., arc, groove, or non-level. For a prong having a two-dimensional flat tip, each of the bevel angles of the prong may be between about 2 degrees to about 40 degrees (e.g., 2, 4, 6, 8, 10, 12, 14, 16, 18, 20, 22, 24, 26, 28, 30, 32, 34, 36, 38, or 40 degrees). The needle may have one or two prongs each with a two-dimensional flat tip in which one or both of the prongs have a bevel angle α of at least about 20 degrees (e.g., from about 20 to about 40 degrees (e.g., about 30 degrees)). Needles having a one-dimensional edge or a two-dimensional flat tip exhibit a reduced likelihood of needle tip curling.

Gauges, Inner Diameters, and Lengths

A hollow needle of the apparatus of the invention may be of any gauge, including gauges of from 18 to 30 (e.g., 18, 19, 20, 21, 22, 23, 24, 25, 26, 27, 28, 29, and 30 gauge). The gauges of a hollow needle may be from 22 to 25 (e.g., 22, 23, 24, and 25 gauge). A hollow needle of the apparatus may have an inner diameter of from about 0.14 mm to about 0.84 mm (e.g., 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, and 0.84 mm). The inner diameter of a hollow needle refers to the diameter of the inner lumen of the hollow needle. The inner diameter of a hollow needle may be from about 0.24 mm to about 0.40 mm (e.g., 0.24, 0.25, 0.26, 0.27, 0.28, 0.29, 0.3, 0.31, 0.32, 0.33, 0.34, 0.35, 0.36, 0.37, 0.38, 0.39, and 0.4 mm). Accordingly, the diameter of a portion of skin tissue removed by a hollow needle of the apparatus (e.g., a cored tissue portion) generally corresponds to the inner diameter of the hollow needle.

Figure 5D:
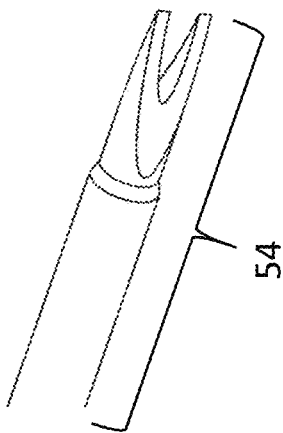
FIG. 5D is a schematic illustration showing a swaged hollow needle with two prongs each having an edge at the tip of the prong.
Figure 5E:
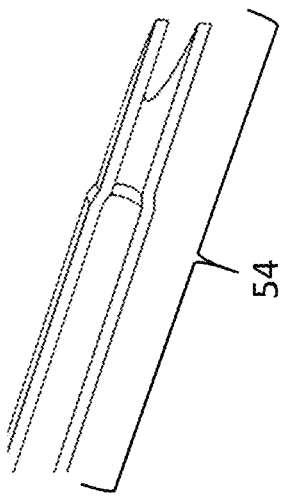
FIG. 5E is a schematic illustration showing a cross-sectional view of the swaged hollow needle shown in FIG. 5D.

In some embodiments, the outer and/or inner diameter of a hollow needle may vary across its lengths, such that the diameter of one region of the hollow needle may be different from the outer and/or inner diameter of another region of the same needle. The change in a diameter across the hollow needle may or may not be continuous. The hollow needle may or may not be entirely cylindrical. For example, one or more hollow needles may be rectangular, serrated, scalloped, and/or irregular in one or more dimensions and along some or all of their lengths. In some embodiments, the inner lumen diameter may vary along the length of a hollow needle. The invention also features a swaged hollow needle having a bevel angle α of at least 20 degrees (e.g., between about 20 and about 40 degrees (e.g., 20, 22, 24, 26, 28, 30, 32, 34, 36, 38, or 40 degrees)) and a variable inner lumen diameter over its length. FIGS. 5D and 5E show swaged hollow needle 54 having a smaller diameter near the distal end of the hollow needle (e.g., near the end of the needle that penetrates the skin tissue). FIG. 5D shows the outside of swaged hollow needle 54 and FIG. 5E shows a longitudinal cross-section of swaged hollow needle 54. In other embodiments, the inner diameter may be wider at the proximal end of a hollow needle (e.g., away from the tip that penetrates the skin). This may facilitate the removal of the cored tissue portion from the hollow needle, may limit the need for clearing of the hollow needle, and may reduce the occurrence of needle clogging.

A hollow needle of the apparatus may be of varying lengths and may have varying active lengths (e.g., the length of a hollow needle configured to penetrate the skin tissue). Active lengths may vary from about 0.5 mm to about 10 mm (e.g., 0.5, 0.6, 0.8, 1, 1.2, 1.4, 1.6, 1.8, 2, 2.2, 2.4, 2.6, 2.8, 3, 3.2, 3.4, 3.6, 3.8, 4, 4.2, 4.4, 4.6, 4.8, 5, 5.2, 5.4, 5.6, 5.8, 6, 6.2, 6.4, 6.6, 6.8, 7, 7.2, 7.4, 7.6, 7.8, 8, 8.2, 8.4, 8.6, 8.8, 9, 9.2, 9.4, 9.6, 9.8, and 10 mm) and may be selectable with manual or automatic controls (e.g., a scroll wheel or an actuation mechanism such as an electromagnetic actuator). Active lengths of a hollow needle may be adjusted and selected depending on the skin area needing treatment. For example, hollow needle with active lengths from about 0.5 mm to about 2 mm (e.g., 0.5, 0.6, 0.8, 1, 1.2, 1.4, 1.6, 1.8, and 2 mm) may be used to treat thin skin, e.g., skin of an eyelid. The thickness of the epidermal and dermal layers of the skin of an eyelid may be from about 0.5 mm to about 1 mm (e.g., 0.5, 0.6, 0.8, and 1). Hollow needles with active lengths from about 5 mm to about 10 mm (e.g., 5, 6, 7, 8, 9, and 10 mm) may be used to treat thick skin, e.g., skin of the back or scar tissue, which can be thicker than healthy skin tissue. The thickness of an epidermal layer of skin may be from about 0.05 to about 2 mm (e.g., 0.05 to 2, 0.05 to 1.95, 0.05 to 1.9, 0.05 to 1.85, 0.05 to 1.8, 0.05 to 1.75, 0.05 to 1.7, 0.05 to 1.65, 0.05 to 1.6, 0.05 to 1.55, 0.05 to 1.5, 0.05 to 1.45, 0.05 to 1.4, 0.05 to 1.35, 0.05 to 1.3, 0.05 to 1.25, 0.05 to 1.2, 0.05 to 1.15, 0.05 to 1.1, 0.05 to 1.05, 0.05 to 1, 0.05 to 0.95, 0.05 to 0.9, 0.05 to 0.85, 0.05 to 0.8, 0.05 to 0.75, 0.05 to 0.7, 0.05 to 0.65, 0.05 to 0.6, 0.05 to 0.55, 0.05 to 0.5, 0.05 to 0.45, 0.05 to 0.4, 0.05 to 0.35, 0.05 to 0.3, 0.05 to 0.25, 0.05 to 0.2, 0.05 to 0.15, 0.05 to 0.1, 0.1 to 2, 0.15 to 2, 0.2 to 2, 0.25 to 2, 0.3 to 2, 0.35 to 2, 0.4 to 2, 0.45 to 2, 0.5 to 2, 0.55 to 2, 0.6 to 2, 0.65 to 2, 0.7 to 2, 0.75 to 2, 0.8 to 2, 0.85 to 2, 0.9 to 2, 0.95 to 2, 1 to 2, 1.05 to 2, 1.15 to 2, 1.2 to 2, 1.25 to 2, 1.3 to 2, 1.35 to 2, 1.4 to 2, 1.45 to 2, 1.5 to 2, 1.55 to 2, 1.6 to 2, 1.65 to 2, 1.7 to 2, 1.75 to 2, 1.8 to 2, 1.85 to 2, 1.9 to 2, and 1.95 to 2 mm). The thickness of a dermal layer of skin may be from 2 to 8 mm (e.g., 2 to 8, 2 to 7.5, 2 to 7, 2 to 6.5, 2 to 6, 2 to 5.5, 2 to 5, 2 to 4.5, 2 to 4, 2 to 3.5, 2 to 3, 2 to 2.5, 2.5 to 8, 3 to 8, 3.5 to 8, 4 to 8, 4.5 to 8, 5 to 8, 5.5 to 8, 6 to 8, 6.5 to 8, 7 to 8, and 7.5 to 8 mm). Active lengths of a hollow needle may be adjusted and selected to penetrate the epidermal and/or the dermal layer of skin.

Active lengths of a hollow needle may also be adjusted using one or more spacers (see FIG. 14), which are described in detail further herein. Hollow needle parameters may be selected based on the area of skin and the condition to be treated. For example, treatment of thin, lax skin on the cheeks may benefit from a hollow needle having an active length of about 2 mm and medium gauge (e.g., 25 gauge), while treatment of thick skin on the back or treatment of scar tissue may benefit from a hollow needle having an active length closer to 5 mm and a thicker gauge (e.g., 22 gauge). A hollow needle of the apparatus may be configured to extend to varying depths of the skin tissue. The depth of penetration of a hollow needle may be determined by the active length (e.g., from about 2 mm to about 5 mm) of the hollow needle. A hollow needle may be configured to extend (i) into the dermal layer, (ii) through the entire dermal layer to the junction of the dermal layer and the subcutaneous fat layer, and/or (iii) into the subcutaneous fat layer.

Micro-Features

Figure 6B:
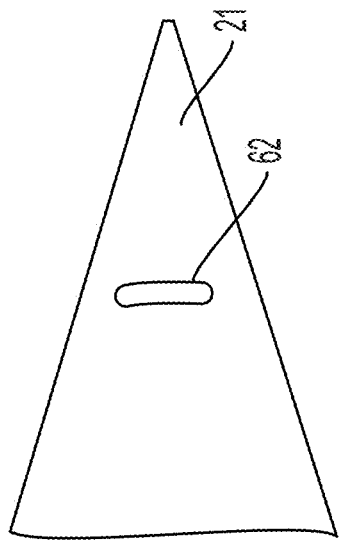
FIGS. 6A and 6B are photographs showing micro-features at the tips of the hollow needles.
Figure 6A:
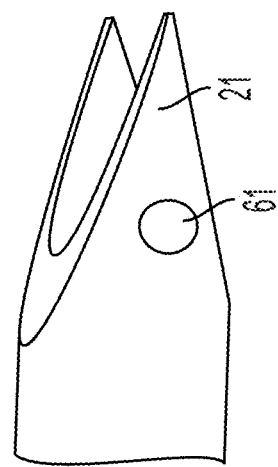

A hollow needle of the apparatus may include one or more micro-features. A micro-feature is an element of the hollow needle that functions to help the hollow needle to capture or "grab" the tissue portion to be removed. A micro-feature may increase the coring rate of the hollow needle. A micro-feature may be located anywhere along the active length of the hollow needle. As shown in FIGS. 6A and 6B, micro-feature 61 or 62 is located near the tip of the hollow needle (e.g., a tip micro-feature). For example, a tip micro-feature may be located near the tip of prong 21 of the hollow needle. In some embodiments, the distance between the tip of a prong of the hollow needle and the start of a micro-feature is from about 100 μm to about 5 mm (e.g., from 100 μm to 5 mm, 200 μm to 5 mm, 300 μm to 5 mm, 400 μm to 5 mm, 500 μm to 5 mm, 600 μm to 5 mm, 700 μm to 5 mm, 800 μm to 5 mm, 900 μm to 5 mm, 1 mm to 5 mm, 1.1 mm to 5 mm, 1.2 mm to 5 mm, 1.3 mm to 5 mm, 1.4 mm to 5 mm, 1.5 mm to 5 mm, 1.6 mm to 5 mm, 1.7 mm to 5 mm, 1.8 mm to 5 mm, 1.9 mm to 5 mm, 2 mm to 5 mm, 2.1 mm to 5 mm, 2.2 mm to 5 mm, 2.3 mm to 5 mm, 2.4 mm to 5 mm, 2.5 mm to 5 mm, 2.6 mm to 5 mm, 2.7 mm to 5 mm, 2.8 mm to 5 mm, 2.9 mm to 5 mm, 3 mm to 5 mm, 3.1 mm to 5 mm, 3.2 mm to 5 mm, 3.3 mm to 5 mm, 3.4 mm to 5 mm, 3.5 mm to 5 mm, 3.6 mm to 5 mm, 3.7 mm to 5 mm, 3.8 mm to 5 mm, 3.9 mm to 5 mm, 4 mm to 5 mm, 4.1 mm to 5 mm, 4.2 mm to 5 mm, 4.3 mm to 5 mm, 4.4 mm to 5 mm, 4.5 mm to 5 mm, 4.6 mm to 5 mm, 4.7 mm to 5 mm, 4.8 mm to 5 mm, 4.9 mm to 5 mm, 100 μm to 4.9 mm, 100 μm to 4.8 mm, 100 μm to 4.7 mm, 100 μm to 4.6 mm, 100 μm to 4.5 mm, 100 μm to 4.4 mm, 100 μm to 4.3 mm, 100 μm to 4.2 mm, 100 μm to 4.1 mm, 100 μm to 4 mm, 100 μm to 3.9 mm, 100 μm to 3.8 mm, 100 μm to 3.7 mm, 100 μm to 3.6 mm, 100 μm to 3.5 mm, 100 μm to 3.4 mm, 100 μm to 3.3 mm, 100 μm to 3.2 mm, 100 μm to 3.1 mm, 100 μm to 3 mm, 100 μm to 2.9 mm, 100 μm to 2.8 mm, 100 μm to 2.7 mm, 100 μm to 2.6 mm, 100 μm to 2.5 mm, 100 μm to 2.4 mm, 100 μm to 2.3 mm, 100 μm to 2.2 mm, 100 μm to 2.1 mm, 100 μm to 2 mm, 100 μm to 1.9 mm, 100 μm to 5 mm, 100 μm to 1.8 mm, 100 μm to 1.7 mm, 100 μm to 1.6 mm, 100 μm to 1.5 mm, 100 μm to 1.4 mm, 100 μm to 1.3 mm, 100 μm to 1.2 mm, 100 μm to 1.1 mm, 100 μm to 1 mm, 100 μm to 900 μm, 100 μm to 800 μm, 100 μm to 700 μm, 100 μm to 600 μm, 100 μm to 500 μm, 100 μm to 400 μm, 100 μm to 300 μm, and 100 μm to 200 μm).

Micro-features may be of varying geometries. A micro-feature may be a hole (see hole 61 of FIG. 6A) (e.g., a circular hole or an oval-shaped hole) or a slit (see slit 62 of FIG. 6B). A slit may be a rectangular-shaped slit, a square-shaped slit, a U-shaped slit, or a T-shaped slit. The shape and dimensions of the micro-feature can be optimized to maximize the ability of the hollow needle to capture a portion of the skin tissue, while minimizing the impact on the mechanical robustness and integrity of the hollow needle. In some embodiments, a micro-feature may be a circular hole having a diameter of from about 10 μm to about 1 mm (e.g., from 10 μm to 1 mm, 10 μm to 900 μm, 10 μm to 880 μm, 10 μm to 860 μm, 10 μm to 840 μm, 10 μm to 820 μm, 10 μm to 800 μm, 10 μm to 780 μm, 10 μm to 760 μm, 10 μm to 740 μm, 10 μm to 720 μm, 10 μm to 700 μm, 10 μm to 680 μm, 10 μm to 660 μm, 10 μm to 640 μm, 10 μm to 620 μm, 10 μm to 600 μm, 10 μm to 580 μm, 10 μm to 560 μm, 10 μm to 540 μm, 10 μm to 520 μm, 10 μm to 500 μm, 10 μm to 480 μm, 10 μm to 460 μm, 10 μm to 440 μm, 10 μm to 420 μm, 10 μm to 400 μm, 10 μm to 380 μm, 10 μm to 360 μm, 10 μm to 340 μm, 10 μm to 320 μm, 10 μm to 300 μm, 10 μm to 280 μm, 10 μm to 260 μm, 10 μm to 240 μm, 10 μm to 220 μm, 10 μm to 200 μm, 10 μm to 180 μm, 10 μm to 160 μm, 10 μm to 140 μm, 10 μm to 120 μm, 10 μm to 100 μm, 10 μm to 80 μm, 10 μm to 60 μm, 10 μm to 40 μm, 10 μm to 20 μm, 20 μm to 1 mm, 40 μm to 1 mm, 60 μm to 1 mm, 80 μm to 1 mm, 100 μm to 1 mm, 120 μm to 1 mm, 140 μm to 1 mm, 160 μm to 1 mm, 180 μm to 1 mm, 200 μm to 1 mm, 220 μm to 1 mm, 240 μm to 1 mm, 260 μm to 1 mm, 280 μm to 1 mm, 300 μm to 1 mm, 320 μm to 1 mm, 340 μm to 1 mm, 360 μm to 1 mm, 380 μm to 1 mm, 400 μm to 1 mm, 420 μm to 1 mm, 440 μm to 1 mm, 460 μm to 1 mm, 480 μm to 1 mm, 500 μm to 1 mm, 520 μm to 1 mm, 540 μm to 1 mm, 560 μm to 1 mm, 580 μm to 1 mm, 600 μm to 1 mm, 620 μm to 1 mm, 640 μm to 1 mm, 660 μm to 1 mm, 680 μm to 1 mm, 700 μm to 1 mm, 720 μm to 1 mm, 740 μm to 1 mm, 760 μm to 1 mm, 780 μm to 1 mm, 800 μm to 1 mm, 820 μm to 1 mm, 840 μm to 1 mm, 860 μm to 1 mm, 880 μm to 1 mm, 900 μm to 1 mm, 920 μm to 1 mm, 940 μm to 1 mm, 960 μm to 1 mm, and 980 μm to 1 mm).

In some embodiments, a micro-feature may be a slit having a length and a width (e.g., a rectangular-shaped slit, a square-shaped slit, a U-shaped slit, or a T-shaped slit), in which the length or width may be from about 10 μm to about 1 mm (e.g., from 10 μm to 1 mm, 10 μm to 900 μm, 10 μm to 880 μm, 10 μm to 860 μm, 10 μm to 840 μm, 10 μm to 820 μm, 10 μm to 800 μm, 10 μm to 780 μm, 10 μm to 760 μm, 10 μm to 740 μm, 10 μm to 720 μm, 10 μm to 700 μm, 10 μm to 680 μm, 10 μm to 660 μm, 10 μm to 640 μm, 10 μm to 620 μm, 10 μm to 600 μm, 10 μm to 580 μm, 10 μm to 560 μm, 10 μm to 540 μm, 10 μm to 520 μm, 10 μm to 500 μm, 10 μm to 480 μm, 10 μm to 460 μm, 10 μm to 440 μm, 10 μm to 420 μm, 10 μm to 400 μm, 10 μm to 380 μm, 10 μm to 360 μm, 10 μm to 340 μm, 10 μm to 320 μm, 10 μm to 300 μm, 10 μm to 280 μm, 10 μm to 260 μm, 10 μm to 240 μm, 10 μm to 220 μm, 10 μm to 200 μm, 10 μm to 180 μm, 10 μm to 160 μm, 10 μm to 140 μm, 10 μm to 120 μm, 10 μm to 100 μm, 10 μm to 80 μm, 10 μm to 60 μm, 10 μm to 40 μm, 10 μm to 20 μm, 20 μm to 1 mm, 40 μm to 1 mm, 60 μm to 1 mm, 80 μm to 1 mm, 100 μm to 1 mm, 120 μm to 1 mm, 140 μm to 1 mm, 160 μm to 1 mm, 180 μm to 1 mm, 200 μm to 1 mm, 220 μm to 1 mm, 240 μm to 1 mm, 260 μm to 1 mm, 280 μm to 1 mm, 300 μm to 1 mm, 320 μm to 1 mm, 340 μm to 1 mm, 360 μm to 1 mm, 380 μm to 1 mm, 400 µm to 1 mm, 420 µm to 1 mm, 440 µm to 1 mm, 460 µm to 1 mm, 480 µm to 1 mm, 500 µm to 1 mm, 520 µm to 1 mm, 540 µm to 1 mm, 560 µm to 1 mm, 580 µm to 1 mm, 600 µm to 1 mm, 620 µm to 1 mm, 640 µm to 1 mm, 660 µm to 1 mm, 680 µm to 1 mm, 700 µm to 1 mm, 720 µm to 1 mm, 740 µm to 1 mm, 760 µm to 1 mm, 780 µm to 1 mm, 800 µm to 1 mm, 820 µm to 1 mm, 840 µm to 1 mm, 860 µm to 1 mm, 880 µm to 1 mm, 900 µm to 1 mm, 920 µm to 1 mm, 940 µm to 1 mm, 960 µm to 1 mm, and 980 µm to 1 mm).

Figure 6C:
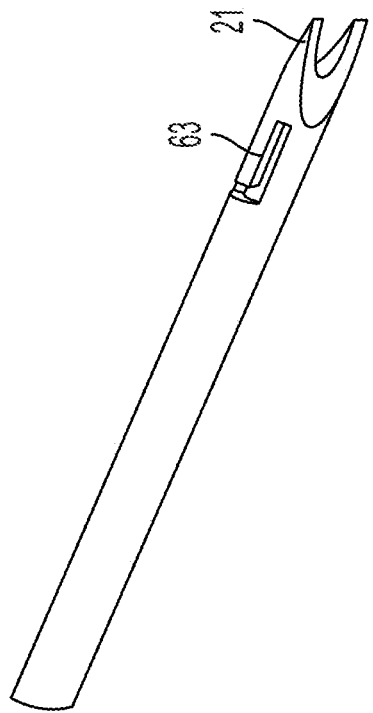
FIG. 6C is a schematic illustration showing a hollow needle having two prongs and a U-shaped micro-feature at the needle tip.
Figure 7:
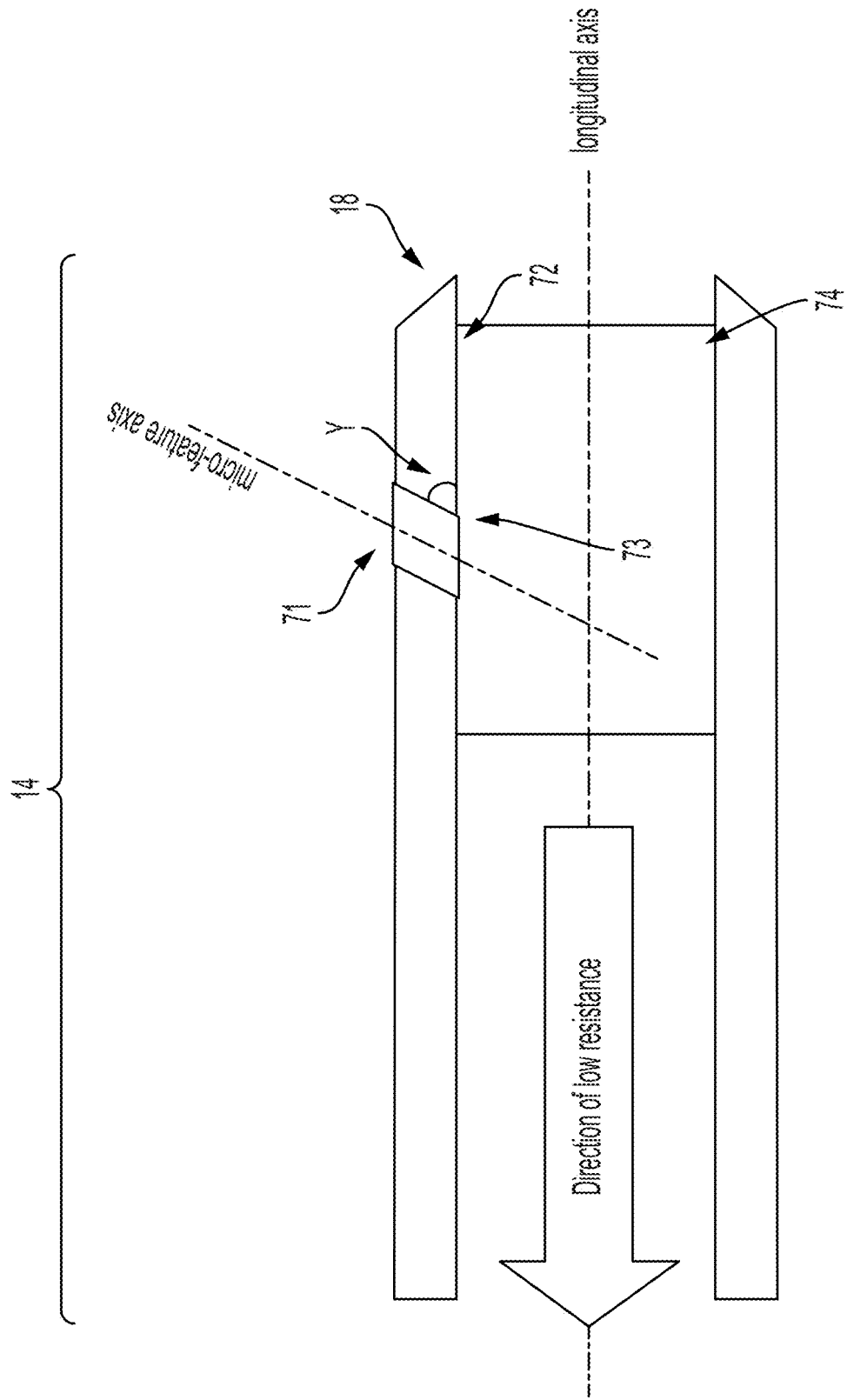
FIG. 7 is a schematic illustration showing a micro-feature intersecting the inner wall of a hollow needle at a non-perpendicular angle and affecting the resistance force applied by the cored tissue portion inside the hollow needle.

The micro-features may be designed and constructed to have a directional effect on the tissue portion captured inside the lumen of the hollow needle. For example, the shape and orientation of the micro-feature may affect the coring force of the hollow needle. As shown in FIG. 6C, U-shaped slit 63 creates a hook near tip 21 of the hollow needle, which may help to retain the tissue portion inside the lumen of the hollow needle upon withdrawal of the needle from the skin. A micro-feature can intersect the inner wall of the hollow needle at a sharp edge, which can directionally affect the coring force of the hollow needle, as well as the resistance force applied by the cored tissue portion inside the lumen of the hollow needle. A micro-feature (e.g., a hole or a slit) drilled or micro-machined into a hollow needle may intersect the inner wall of the hollow needle at a perpendicular angle or at a non-perpendicular angle (e.g., an angle of from about 5 degrees to less than about 90 degrees, such as 5 to 85 degrees, 5 to 80 degrees, 5 to 75 degrees, 5 to 70 degrees, 5 to 65 degrees, 5 to 60 degrees, 5 to 55 degrees, 5 to 50 degrees, 5 to 45 degrees, 5 to 40 degrees, 5 to 35 degrees, 5 to 30 degrees, 5 to 25 degrees, 5 to 20 degrees, 5 to 15 degrees, 5 to 10 degrees, 10 to 85 degrees, 15 to 85 degrees, 20 to 85 degrees, 25 to 85 degrees, 30 to 85 degrees, 35 to 85 degrees, 40 to 85 degrees, 45 to 85 degrees, 50 to 85 degrees, 55 to 85 degrees, 60 to 85 degrees, 65 to 85 degrees, 70 to 85 degrees, 75 to 85 degrees, and 80 to 85 degrees). For example, FIG. 7 shows hollow needle 14 containing tip micro-feature 71 that intersects inner wall 72 of hollow needle at a non-perpendicular angle γ and creates sharp edge 73. As tissue portion 74 enters the hollow needle from needle tip 18, tissue portion 74 is traveling in the direction of lower resistance. As hollow needle 14 is being withdrawn from the skin tissue, as well as once the hollow needle 14 is released from the skin tissue, micro-feature 71 helps to retain tissue portion 74 inside the lumen of hollow needle 14 and prevents tissue portion 74 from being released from hollow needle 14. One or more micro-features may be micro-machined into the hollow needle through available processes and techniques, such as laser drilling and wire electrostatic discharge machining (EDM).

Needle Coating

Figure 8:
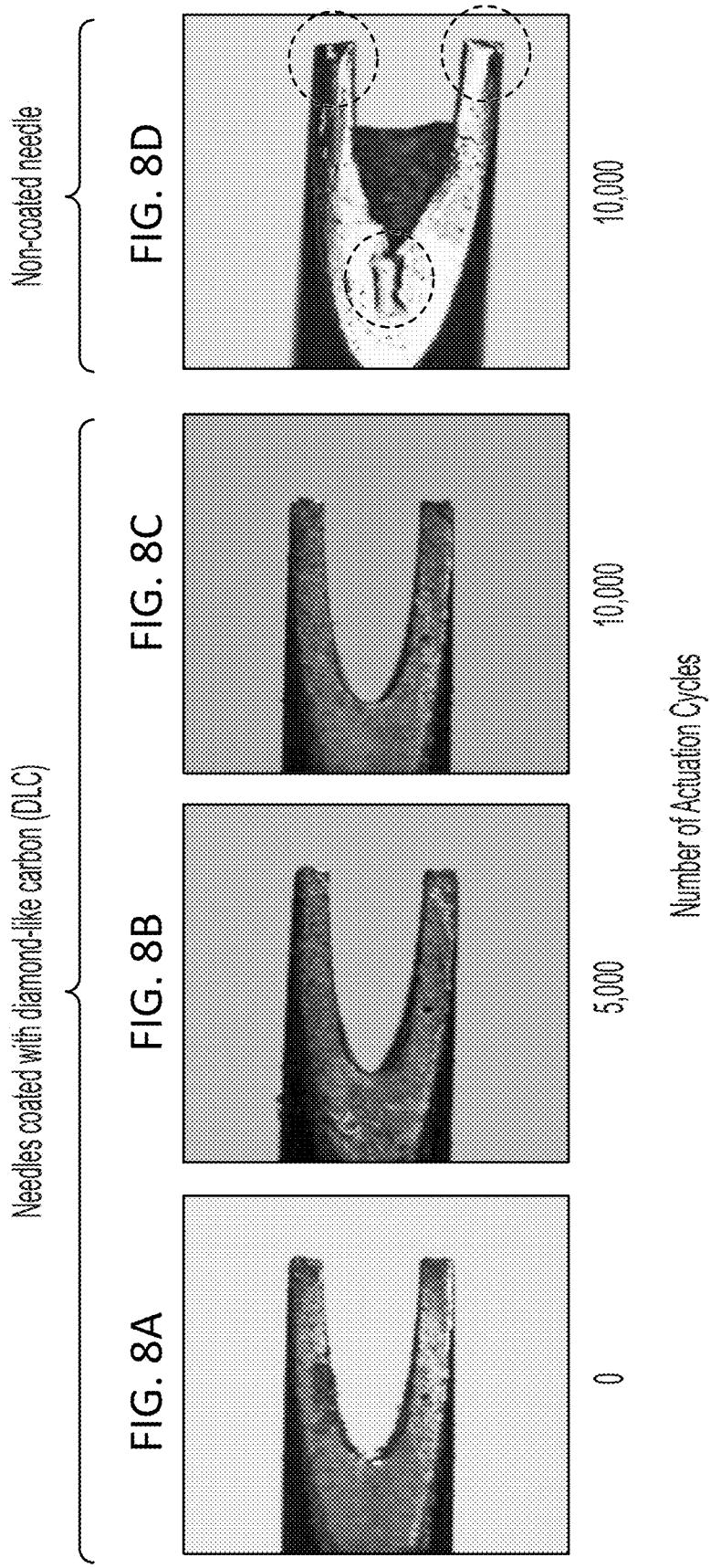
FIGS. 8A, 8B, 8C, and 8D are photographs showing that hollow needles coated with diamond-like carbon (DLC) did not display any sign of needle heel degradation after 10,000 actuation cycles, while non-coated hollow needle showed needle heel degradation after 10,000 actuation cycles.

A hollow needle of the apparatus may be coated with a material (e.g., a hard material) that improves or maintains the mechanical integrity, durability, and reliability of the hollow needle. The coating material may help to prevent damage, abrasion, and wear and tear of the needle tip and heel during repeated insertions into and withdrawals from skin tissue. Examples of materials (e.g., a hard material) that may be used to coat a hollow needle of the apparatus include, but are not limited to, TiN, TiCN, TiAlN, ZrN, and diamond-like carbon (DLC). The hard material may be applied as a coating to the outside surface of a hollow needle, the inner surface (e.g., the surface of the inner lumen) of a hollow needle, or both surfaces. FIGS. 8A-8C show that a hollow needle coated with DLC exhibited a reduction in needle heel and tip degradation over 10,000 actuation cycles of insertions and withdrawals into pig skin, while a non-coated hollow needle showed needle heel and tip degradation (indicated by dashed circles) over 10,000 actuation cycles of insertions and withdrawals into pig skin (FIG. 8D).

Surface of Needle Lumen

Figure 9:
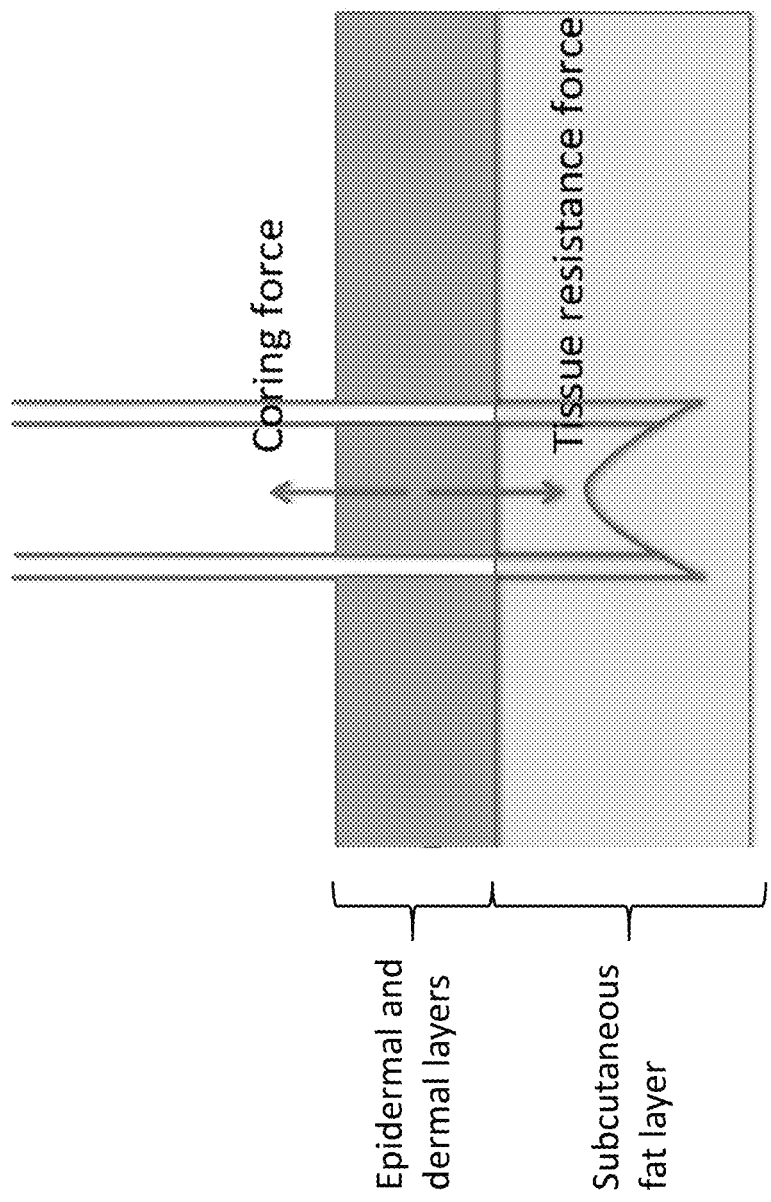
FIG. 9 is a schematic illustration showing needle coring force and tissue resistance force on a cored tissue portion inside the lumen of a hollow needle.

The lumen surface of a hollow needle may affect the coring force, coring rate, and insertion force of the hollow needle. In particular, the friction between the lumen surface and a cored tissue portion may determine the coring force, coring rate, and insertion force. The hollow needles described herein are designed to maximize coring rate and minimize hollow needle insertions that do not result in cored tissue removal. A tissue portion detaches from the skin when the coring force (e.g., the force applied by the hollow needle of the apparatus to the cored tissue portion as the needle is being withdrawn from the skin) exceeds the tissue resistance force, which is determined by the connection of the tissue portion to its surrounding tissue. For example, when the hollow needle is fully inserted through the dermal layer of the skin, the tissue resistance force is determined by the connection between the tissue portion in the lumen of the needle and the subcutaneous fat layer. Accordingly, when the coring force exceeds the tissue resistance force, the cored tissue portion is captured in the lumen of the hollow needle and removed from the skin (FIG. 9). A rough lumen surface increases the friction between the cored tissue portion and the lumen surface, which may result in increased insertion force, increased coring force, and increased coring rate. Lubrication of the lumen surface reduces the friction between the cored tissue portion and the lumen surface, which may result in decreased insertion force, decreased coring force, and decreased coring rate. An overly rough and uneven lumen surface may lead to high occurrence of needle degradation (e.g., needle heel and tip degradations), may cause difficulty in removing cored tissue portions from the lumen, and/or may cause needle clogging. The degree of roughness of the lumen surface may be optimized to increase the coring force and coring rate without compromising the durability of the needle, the insertion force, the ability to remove tissue from the needle lumen, and the resistance of the needle to degradation (e.g., needle heel and tip degradation).

In some embodiments, hollow needles and methods of the invention may have a coring rate of at least about 5% (e.g., from about 5% to about 100%, such as 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 5% to 35%, 5% to 30%, 5% to 25%, 5% to 20%, 5% to 15%, 5% to 10%, 10% to 95%, 15% to 95%, 20% to 95%, 25% to 95%, 30% to 95%, 35% to 95%, 40% to 95%, 45% to 95%, 50% to 95%, 55% to 95%, 60% to 95%, 65% to 95%, 70% to 95%, 75% to 95%, 80% to 95%, 85% to 95%, and 90% to 95%).

In some embodiments, hollow needles and methods of the invention may have a coring force of about 3 N to about 10 N (e.g., 3, 3.5, 4, 4.5, 5, 5.5, 6, 6.5, 7, 7.5, 8, 8.5, 9, 9.5, and 10 N). In some embodiments, a two-prong hollow needle having a bevel angle α of 20 degrees may have a coring force of about 3 N to about 10 N (e.g., 3, 3.5, 4, 4.5, 5, 5.5, 6, 6.5, 7, 7.5, 8, 8.5, 9, 9.5, and 10 N).

A coating material and/or a lubricant may affect the degree of roughness of the lumen surface, and thus the friction between the lumen surface and a cored tissue portion. The lumen surface of a hollow needle may be polished by running a lubricant or a polishing media though the hollow needle to reduce the roughness of the lumen surface. Examples of lubricants include, but are not limited to, salt-based lubricants (e.g., buffered saline solutions (e.g., PBS)), sugar-based lubricants (e.g., sucrose and glucose solutions), and surfactant-based lubricants (e.g., solutions containing Tween20). The degree of roughness of the lumen surface of the hollow needle may also be affected by the manufacturing process used to make the hollow needle. Table 2 below shows lumen surface roughness measured in Ra (arithmetic average of roughness profile) and Rz (means roughness depth) of hollow needles made using single plug, double plug, and sunk manufacturing processes. The lumen surface of hollow needles made using double plug process is smoother (lower Ra and Rz values) than the lumen surface of hollow needles made using single plug process.

TABLE 2

| Manufacturing Process | Ra | Rz |
| --- | --- | --- |
| Single plug | 53 | 299 |
| Double plug | 37 | 206 |
| Sunk | 56 | 330 |

Needle Manufacture

A hollow needle of the apparatus may be made using available manufacturing techniques and processes. For example, manufacturing of a hollow needle starts with drawing the needle hypodermic tube, followed by forming the needle tip. The needle hypodermic tube may be drawn using manufacturing processes, e.g., single plug, double plug, and sunk. The needle tip may be formed by grinding. For example, a hollow needle having one prong may be formed by grinding one side of the distal end of the hollow needle at an angle relative to the longitudinal axis of the hollow needle. Similarly, a hollow needle having two prongs may be formed by grinding opposite sides of the distal end of the hollow needle at an angle relative to the longitudinal axis of the hollow needle. The grinding process may be performed at a low temperature to prevent or reduce annealing of the needle material and to prevent the needle material from undergoing phase transitions at high temperatures (e.g., at alloy transition temperature, which is defined by the alloy stoichiometry). Annealed material may become ductile and more prone to bending, which may reduce the durability and mechanical integrity of the hollow needle. Maintaining a low temperature (e.g., a temperature lower than the alloy transition temperature) during the grinding process may be achieved by, e.g., reducing the grinding speed and/or grinding rate and using a cooling fluid (e.g., periodically submerging the needle material and/or the grinding machinery in a cooling fluid). In some embodiments, the cooling fluid used may be at room temperature. Other non-grinding techniques and processes may also be used to manufacture the hollow needle(s) of the apparatus, e.g., electrical discharge machining.

Needle Assembly

FIGS. 1A-1F are schematic illustrations of an exemplary needle assembly 10 of the invention including support base 11, z-actuator (e.g., a voice coil) 12, tissue removal tool (e.g., a piston) 13, hollow needle 14, aspiration tube 15, trap 16, pressure generating source (e.g., a vacuum pump) 17, and scaffold 18. Such a needle assembly may permit treatment of multiple areas of a subject without forcing the subject to move, in contrast to other, larger medical treatment systems. A needle assembly of the apparatus (e.g., needle assembly 10 shown in FIGS. 1A-1F, 15B, and 16G-16U) may be detachably attached to other components of the apparatus (e.g., to an actuation unit of the apparatus) for easy and quick connection and disconnection. In some embodiments, the needle assembly (e.g., needle assembly 10) may be detachably attached to an actuation unit of the apparatus (e.g., actuation unit 151 shown in FIGS. 15A, 15B, 16B, and 16G-16U) using a locking or connecting mechanism (described further herein; see FIGS. 17A-17I, 18A-18C, 19A-19C, 20A-20E, 21A-21D, and 22A-22D). The entire needle assembly and/or components of the needle assembly may be detached from other components of the apparatus (e.g., detached from the actuation unit) to be replaced or sterilized after use.

Needle assembly 10 may include additional components, such as tubing and/or cables to couple various components and device control electronics, a power supply (e.g., an alternator and/or battery component), and/or a user interface. The components of the needle assembly may be detachably engaged for easy and quick connection and disconnection. The components of the needle assembly may be readily cleaned, sterilized (e.g., by steam sterilization or other known methods), and/or replaced. The components of the needle assembly may be provided to an operator (e.g., a doctor or surgeon) in sterile condition prior to use on a patient and many, if not all, of the components can be re-sterilized or replaced with sterile components prior to a subsequent use. For example, components of the needle assembly and/or the entire needle assembly may be readily removable from the apparatus for sterilization or replacement after use of the apparatus.

Z-actuator (e.g., a voice coil) 12 is configured to couple with hollow needle 14 in needle assembly 10. Z-actuator (e.g., a voice coil) 12 may have a locking mechanism to secure the hollow needle 14 in place during operation. In some embodiments, z-actuator 12 and hollow needle 14 may be locked by establishing a magnetic connection between the two. In other embodiments, z-actuator 12 and hollow needle 14 may be locked by establishing a mechanical connection between the two using, e.g., quick-connect clasps. The z-actuator-hollow needle locking mechanism may be detachably engaged for easy and quick connection and disconnection. The z-actuator-hollow needle locking mechanism may include one or more of adhesive, magnetic, electrical, and/or mechanical components (e.g., one or more gaskets, o-rings, septa, springs, clasps, and other engagement members). In some embodiments, the z-actuator may include a groove or depression for placement of an o-ring (e.g., a viton o-ring, a nitrile rubber o-ring, and a thermoplastic polyurethane o-ring) that will allow for a seal to form between z-actuator 12 and hollow needle 14. The portion of hollow needle 14 engineered to engage with z-actuator 12 may include a corresponding groove or depression. In other embodiments, a locking mechanism may involve mated pieces made of molded plastic. As an example, hollow needle 14 may form a seal by sliding partway into z-actuator 12. Z-actuator 12 and hollow needle 14 may also include interlocking ridges (e.g., made of plastic, rubber, or other material) to enhance or form a seal between the components. Z-actuator 12 may also feature a mechanism to activate detachment of hollow needle 14 from z-actuator 12. This mechanism may include one or more of a button, key, switch, toggle, spin-wheel, touch screen, and/or sliding lock. The detachment mechanism may be a quick-release mechanism. In some embodiments, one component (e.g., z-actuator 12) includes a depressible portion that engages a seal when the other component (e.g., hollow needle 14) is slid into the other. Depression of the portion may be disengaged by activation of a sliding lock, eliminating the seal between the components to allow their separation and, e.g., removal and replacement of hollow needle 14.

Needle assembly 10 may also include a power supply or be detachably attached to a power supply. For example, needle assembly 10 may have a holder for batteries that power operation of the apparatus or may be configured to receive an element including batteries. The holder may be configured to charge the batteries (e.g., when depleted) with a paired charging station, without requiring removal of the batteries, or the batteries may be removed from the apparatus for replacement or charging. In another embodiment, needle assembly 10 may include electronics and components (e.g., a power cord) that allow it to be powered from an external power supply, such as a direct or alternating current supply or a generator.

Mechanisms for Removal of Cored Tissue Portion from Hollow Needle

Cored tissue portion(s) may require removal from the lumen of a hollow needle of the apparatus after the needle containing the cored tissue portion inside its lumen is withdrawn from the skin, e.g., in order to continue the skin treatment procedure. The cored tissue portion may be removed from the needle lumen after each actuation cycle or after multiple actuation cycles. In some embodiments, a tissue removal tool (e.g., a piston) may be inserted from the proximal end (e.g., the end opposite the needle tip) of the hollow needle to push out the cored tissue portion. In some embodiments, the cored tissue portion may be removed through the distal end of the hollow needle (e.g., at the needle tip) using an aspiration tube coupled to a pressure generating source (e.g., a vacuum). The cored tissue portion may also be removed through the proximal end of the hollow needle by applying a differential pressure (e.g., a vacuum) or out of the distal end of the needle using compressed air or a pressurized fluid to push the cored tissue portion out of the distal end.

Tissue Removal Tool

A tissue removal tool may be used to push the cored tissue portion out of the lumen of a hollow needle. A tissue removal tool may be a piston or a pin that can fit inside the lumen of the hollow needle (e.g., without creating a vacuum inside the lumen (e.g., the gap between the tissue removal tool and the wall of the lumen of the hollow needle is large enough to allow the passage of air)). In a preferred embodiment, the tissue removal tool is a piston. A tissue removal tool (e.g., a piston) does not disrupt the structural integrity of the cored tissue portion. In some embodiments, a tissue removal tool (e.g., a piston) may push the cored tissue portion out of the lumen of a hollow needle as a substantially intact, cored tissue portion (see, e.g., cored tissue portion 74 at needle tip 18 in FIG. 12), instead of as pieces of the cored tissue portion, which may be difficult to remove completely. Maintaining the structural integrity of the cored tissue portion as a substantially intact tissue portion during the removal process facilitates efficient and complete tissue removal from the hollow needle.

Figure 10:
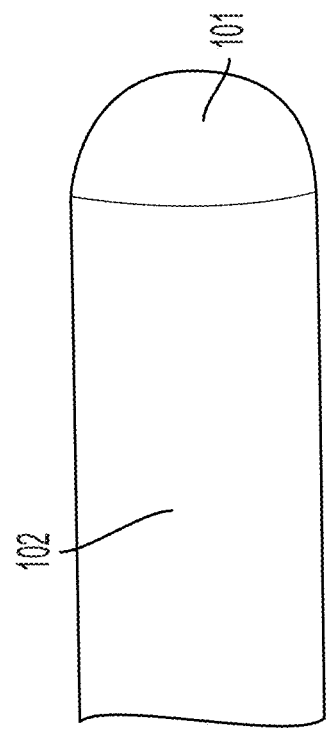
FIG. 10 is a photograph of a round, polished end of a piston used to remove cored tissue portion(s) from the lumen of a hollow needle.

A piston may be of varying geometry. The cross-section of the piston may be, e.g., round, oval, rectangular, or square. In a preferred embodiment, the cross-section of the piston is round. The geometry of the piston matches the shape of the lumen of the hollow needle such that the piston fits well inside the lumen and is able to freely slide along the longitudinal axis of the hollow needle, for example, without creating a vacuum. The piston may have a diameter that is less than the inner diameter of the hollow needle (e.g., a diameter that is 0.01% to 10% less (e.g., 0.01%, 0.05%, 0.1%, 0.15%, 0.2%, 0.25%, 0.3%, 0.35%, 0.4%, 0.45%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% less). The end of the piston, which touches the cored tissue portion as the piston pushes the cored tissue portion out of or towards the distal end of the needle, may be round or flat. For example, as shown in FIG. 10, end 101 of piston 102 is round. A rounded piston end may prevent the attachment of the cored tissue portion to the piston during tissue removal. The piston may be polished to minimize friction and abrasion between the piston and the inner wall of the hollow needle, thus reducing wear and tear of the inner wall.

The piston may stay at a constant position. In this example, the hollow needle is moved up and down to engage the stationary piston. The piston may be inserted and withdrawn from the lumen of a hollow needle. As shown in FIGS. 1A-1F, hollow needle 14 of needle assembly 10 moves down to penetrate into the skin and to capture and retain the cored tissue portion inside its lumen. As hollow needle 14 moves up to withdraw from the skin, it comes into contact with tissue removal tool (e.g., a piston) 13, which stays stationary. Tissue removal tool (e.g., a piston) 13 is constructed to fit inside the lumen of the needle. Hollow needle 14 continues to move upward, which allows tissue removal tool (e.g., a piston) 13 to extend further into the lumen and all the way to needle tip 18, thereby pushing the cored tissue portion towards or out of needle tip 18.

In another example, after hollow needle 14 containing a cored tissue portion inside its lumen is withdrawn from the skin, tissue removal tool (e.g., a piston) 13 moves down towards to the end of hollow needle 14 and enters the needle lumen through the proximal end of the needle. In this example, hollow needle 14 containing the cored tissue portion stays stationary while tissue removal tool (e.g., a piston) 13 moves downward to needle tip 18, thereby pushing the cored tissue portion towards or out from needle tip 18. The length of tissue removal tool (e.g., a piston) 13 may be adjusted to allow the cored tissue portion to be pushed towards or out of needle tip 18 while the needle is in its uppermost position and not penetrating into the skin. One or more actuators (e.g., the x-, y-, and/or z-actuator) (e.g., actuation unit 151 including x- and y-actuators shown in FIGS. 15A, 15B, and 16G-16U) may be coupled to a needle assembly (e.g., needle assembly 10 shown in FIGS. 1A-1F, 15B, and 16G-16U) to move the hollow needle (e.g., hollow needle 14) away from the skin surface before the cored tissue portion is pushed out by the tissue removal tool (e.g., a piston; e.g., see tissue removal tool 13 shown in FIGS. 1A-1F) such that the cored tissue portion does not drop onto the skin surface once it is pushed out.

Figure 11:
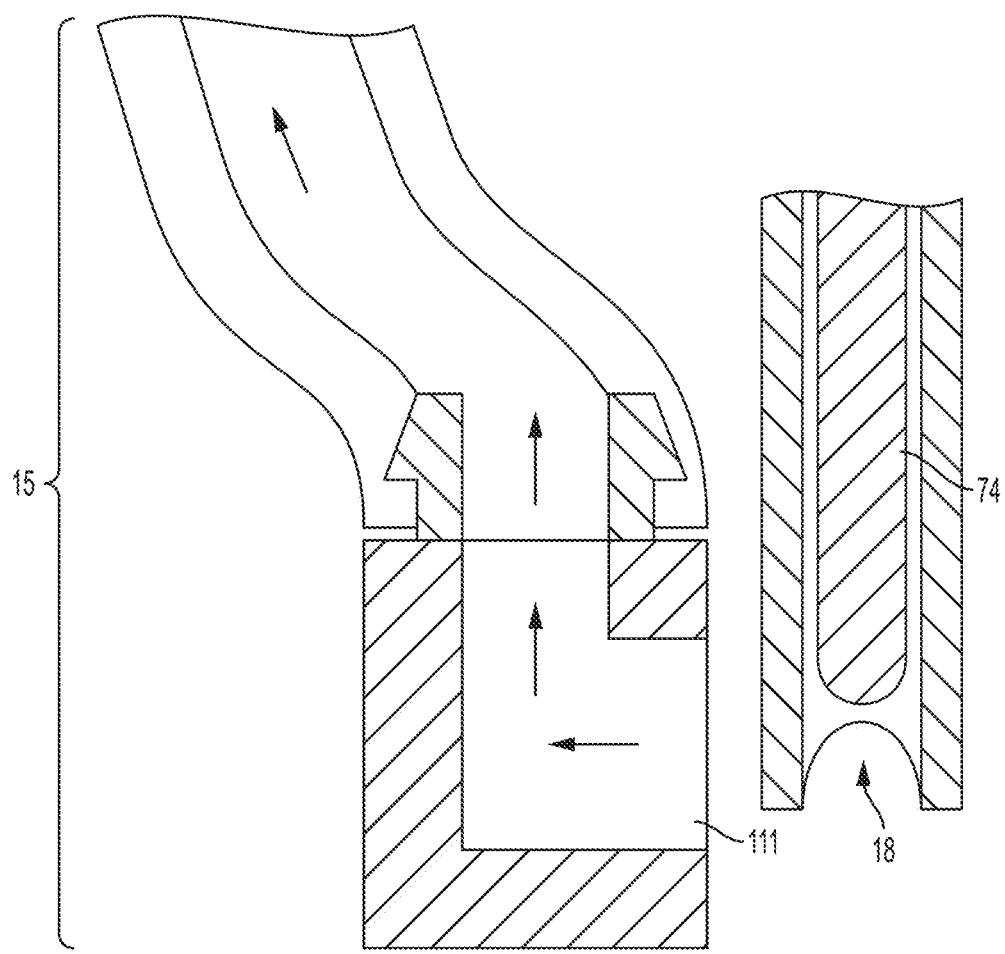
FIG. 11 is a schematic illustration showing an aspiration tube proximal to the tip of a hollow needle containing a cored tissue portion inside its lumen.

An aspiration tube (e.g., aspiration tube 15 shown in FIGS. 1A-1F) may be used in combination with a tissue removal tool (e.g., a piston) to remove the cored tissue portion from the needle tip. The aspiration tube may stay at a constant position. As shown in FIG. 11, after cored tissue portion 74 is pushed to needle tip 18 by tissue removal tool (e.g., a piston), aspiration tube 15 located in proximity to needle tip 18 may be used to remove cored tissue portion 74 through a suction force. The opening of aspiration tube 111 may be in proximity to needle tip 18 when the needle is in its uppermost position. Thus, once cored tissue portion 74 is at needle tip 18, it can be aspirated into aspiration tube 15 by applying suction using a pressure generating source (e.g., a vacuum pump).

Figure 12:
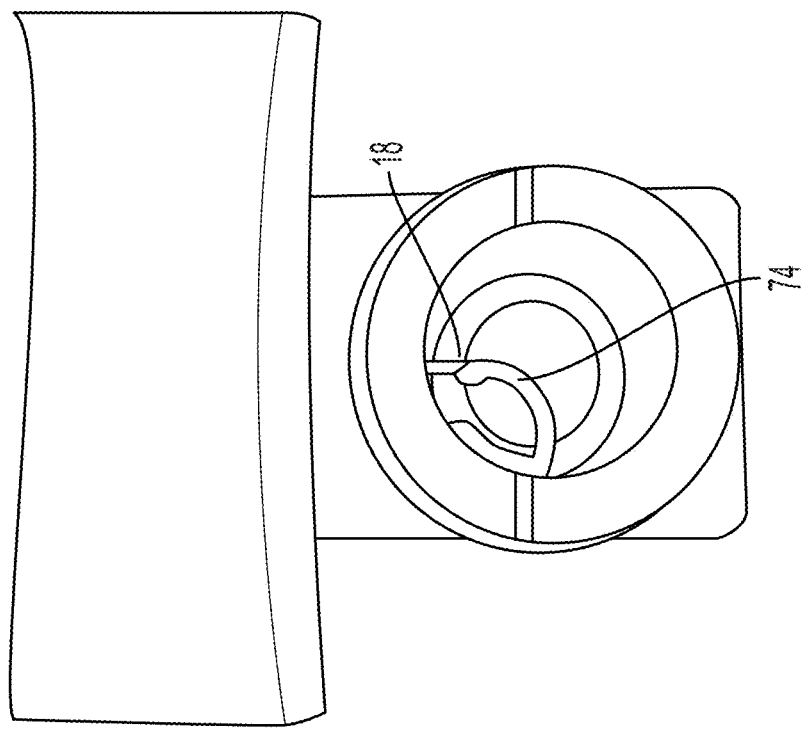
FIG. 12 is a photograph showing a cored tissue portion ejected from a needle tip.

As shown in FIGS. 1A-1F, pressure generating source (e.g., a vacuum pump) 17 may be connected to aspiration tube 15 to provide the suction force. In some embodiments, trap 16 may be installed between aspiration tube 15 and pressure generating source (e.g., a vacuum pump) 17 to collect the cored tissue portions for disposal, subsequent use (e.g., tissue graft or growth), or biochemical analysis and to prevent the cored tissue portion from entering pressure generating source (e.g., a vacuum pump) 17. FIG. 12 further shows cored tissue portion 74 at needle tip 18.

Differential Pressure

A cored tissue portion inside the lumen of a hollow needle may be collected at the proximal or distal end of the needle by applying a differential pressure across the needle. In one embodiment, after the needle containing the cored tissue portion inside its lumen is withdrawn from the skin, the needle may move to a dock station or a separate unit, which may contain a pressure generating source (e.g., a vacuum pump) that provides suction and/or vacuum at the proximal end of the needle. Suction and/or vacuum may be applied at the proximal end of the hollow needle to pull the cored tissue portion out of the needle from its proximal end. A trap may be installed at the proximal end of the needle and between the needle and the pressure generating source (e.g., a vacuum pump) to collect the cored tissue portions for disposal, subsequent use (e.g., tissue graft or growth), or biochemical analysis and to prevent the cored tissue portions from entering the pressure generating source (e.g., a vacuum pump). In some embodiments, a differential pressure may be applied to a hollow needle (e.g., a swaged hollow needle having a variable inner lumen diameter over its length and a bevel angle α of at least 20 degrees (e.g., swaged hollow needle 54)). Tissue removal may be facilitated by increasing the inner lumen diameter in the direction of the tissue removal. An increased inner lumen diameter in part of a hollow needle (e.g., a swaged hollow needle having a variable inner lumen diameter over its length and a bevel angle α of at least 20 degrees (e.g., swaged hollow needle 54)) may reduce the friction between the cored tissue portion and the wall of the needle lumen. For example, suction and/or vacuum may be applied at the proximal end of a hollow needle (e.g., a swaged hollow needle having a variable inner lumen diameter over its length and a bevel angle α of at least 20 degrees (e.g., swaged hollow needle 54)) to pull the cored tissue portion out from the proximal end.

Figure 13:
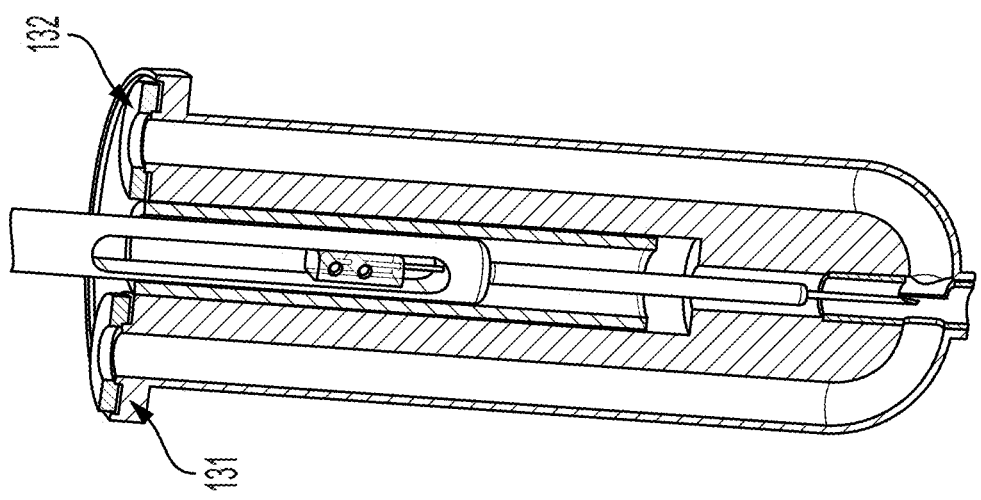
FIG. 13 is a schematic illustration showing a high pressure port used to aspirate a cored tissue portion from the proximal end of a hollow needle by applying a high pressure burst. The high pressure port is coupled to a tissue recovery port used to capture the aspirated cored tissue portion.

In another arrangement, a burst of high pressure may be applied at the proximal end of a hollow needle to pull the cored tissue portion out of the needle from its proximal end. As illustrated in FIG. 13, high pressure port 131 may be coupled to tissue recovery port 132, which collects the cored tissue portions.

In another embodiment, after the needle containing the cored tissue portion inside its lumen is withdrawn from the skin, a pressure generating source (e.g., a vacuum pump) providing suction and/or vacuum may be placed proximal to the distal end of the needle. Suction and/or vacuum may be applied at the distal end of the hollow needle to pull the cored tissue portion out of the needle from its distal end.

In another embodiment, after the needle containing the cored tissue portion inside its lumen is withdrawn from the skin, a tissue removal tool (e.g., tissue removal tool (e.g., a piston) 13) may be used to push the cored tissue portion out of or towards the distal end of the needle. Once the cored tissue portion is at the distal end of the needle (e.g., FIG. 12 showing cored tissue portion 74 at needle tip 18), suction and/or vacuum may be applied at the distal end of the hollow needle to remove the cored tissue.

Non-limiting possible pressures for a pressure generating source (e.g., a vacuum pump) to provide suction and/or vacuum at the proximal or distal end of a hollow needle to remove a cored tissue portion from the needle lumen include from about −8 mmHg to about −16 mmHg (e.g., −8, −9, −10, −11, −12, −13, −14, −15, and −16 mmHg). For example, the minimal air flow rate in the aspiration line of a pressure generating source (e.g., a vacuum pump) is from about 1 cubic feet per minute (CFM) to about 6 CFM (e.g., 1, 2, 3, 4, 5, and 6 CFM (e.g., 3 CFM)).

Tissue Pressure

A cored tissue portion inside the lumen of a hollow needle may be pushed out of the proximal end of the needle by the insertion of one or more new tissue portions during the subsequent actuation cycles. The inner wall of the hollow needle may be lubricated by, e.g., a sterile saline solution, to prevent clogging of the needle as multiple tissue portions are inserted into the needle. Also, a trap may be attached at the proximal end of the needle to collect the cored tissue portions as they are being pushed out of the needle for disposal, subsequent use (e.g., tissue graft or growth), or biochemical analysis.

Compressed Air or Pressurized Liquid

A cored tissue portion inside the lumen of the needle may be removed from the needle by applying compressed air or a pressurized fluid (e.g., a sterile saline solution) through the needle. Compressed air or pressurized fluid may be applied through the proximal end to push the cored tissue portion out from the distal end of the needle.

Other Mechanisms for Removal of Cored Tissue Portion

A cored tissue portion inside the lumen of the needle may also be removed from the needle using a heating element coupled to the needle. For example, a heating element coupled to the needle may be actuated which causes the needle to heat up to facilitate separation of the cored tissue portion from the surrounding skin. The cored tissue portion may be dried or desiccated prior to being removed from the lumen of the hollow needle. A vacuum source may then be applied to remove the heated cored tissue portion.

Pressure Generating Source

The apparatus may further include or be otherwise coupled to a pressure generating source. A pressure generating source may be applied to remove and/or collect cored tissue portions from the lumen of a hollow needle to prevent needle clogging during operation. In one embodiment, suction and/or vacuum may be applied via a hollow needle of the apparatus. A hollow needle and a pressure generating source (e.g., a vacuum pump) may be configured to remove and/or collect cored tissue portions from the lumen of the hollow needle by providing suction and/or vacuum after penetration of the hollow needle into the skin but before removal of the hollow needle from the skin. Following penetration into the tissue by a hollow needle, vacuum may be applied to draw the tissue portion in the lumen of the hollow needle from a treated skin area through the proximal end of the hollow needle and through tubing coupling the hollow needle to the pressure generating source (e.g., a vacuum pump). A trap may be installed between the proximal end of the hollow needle and the pressure generating source (e.g., a vacuum pump) to prevent the tissue portion from entering the pressure generating source (e.g., a vacuum pump). The pressure generating source (e.g., a vacuum pump) may also be activated after the hollow needle containing the tissue portion in the lumen is removed from the skin.

Alternatively, the pressure generating source (e.g., a vacuum pump) may be integrated with a separate aspiration tube. For example, as described previously and shown in FIGS. 1A-1F, tissue removal tool (e.g., a piston) 15 coupled to hollow needle 14 may slide freely from the proximal end to the distal end of the hollow needle to push the cored tissue portion towards or out of needle tip 18. Aspiration tube 15 integrated with pressure generating source (e.g., a vacuum pump) 17 may be placed proximal to needle tip 18 to provide suction and/or vacuum after the cored tissue portion is pushed to needle tip 18. Trap 16 may be installed between aspiration tube 15 and pressure generating source (e.g., a vacuum pump) 17 to prevent the cored tissue portion from entering pressure generating source (e.g., vacuum pump) 17.

The pressure generating source may be a low pressure generating source. For example, the pressure generating source may be capable of providing vacuum and/or suction. Vacuum sources may include one or more rotary pumps, momentum transfer pumps, diffusion pumps, scroll pumps, and/or diaphragm pumps. In some embodiments, a low pressure generating source may include a house or central vacuum system. In other embodiments, a suction source may include a wall or portable suction device. In some embodiments, a vacuum source provides an absolute pressure less than about 6.3 kPa (e.g., from about 0.1 kPa to about 6 kPa, such as from 0.1 kPa to 6 kPa, 0.1 kPa to 5 kPa, 0.1 kPa to 4 kPa, 0.1 kPa to 3 kPa, 0.1 kPa to 2 kPa, 0.1 kPa to 1 kPa, 0.5 kPa to 6 kPa, 0.5 kPa to 5 kPa, 0.5 kPa to 4 kPa, 0.5 kPa to 3 kPa, 0.5 kPa to 2 kPa, 0.5 kPa to 1 kPa, 1 kPa to 6 kPa, 1 kPa to 5 kPa, 1 kPa to 4 kPa, 1 kPa to 3 kPa, 1 kPa to 2 kPa, 1.5 kPa to 6 kPa, 1.5 kPa to 5 kPa, 1.5 kPa to 4 kPa, 1.5 kPa to 3 kPa, and 1.5 kPa to 2 kPa).

Spacer

Figure 14B:
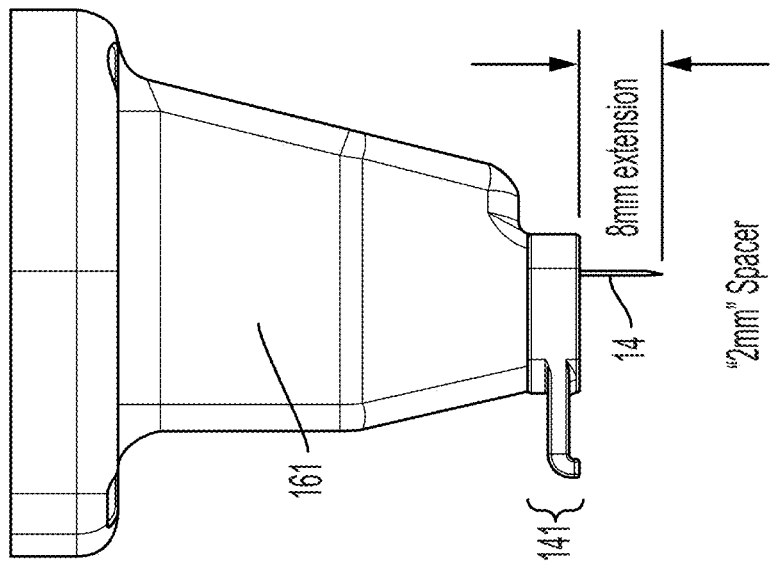
FIGS. 14A and 14B are schematic illustrations showing two different spacers each coupled to the end of the cover of the apparatus.
Figure 14A:
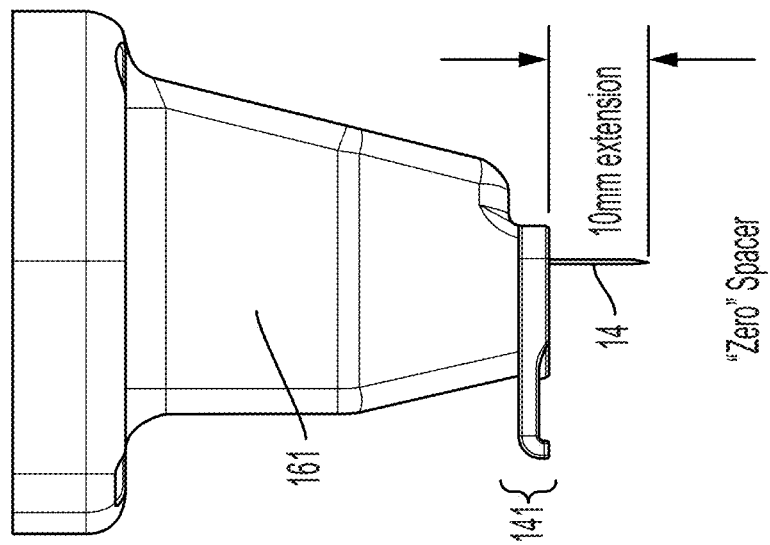

An apparatus of the invention may include one or more spacers that function to control the depth of penetration of a hollow needle. Skin thickness varies significantly between body sites and in some cases, between subjects. Tissue penetration depth is important to ensure coring tissue portions of the appropriate size and to avoid injury to tissue layers beyond the subcutaneous fat layer (e.g., muscle layer). One or more spacers may be attached to the apparatus, e.g., between the cover of the apparatus and the skin (see FIGS. 14A, 14B, and 16A-16C). A spacer is configured to control the depth of insertion of a hollow needle and allows adjustments of the extension and penetration of the hollow needle into the skin. FIGS. 14A and 14B show two spacers 141 and 142 that allow different insertion depths of hollow needle 14. For example, "zero" spacer 141 (FIG. 14A) attached to the distal end of cover 161 of the apparatus allows a 10 mm insertion depth of hollow needle 14. This type of spacer may be added to the distal end of the cover of the apparatus of the invention for coring thick skin tissues, which requires a deep penetration of the hollow needle. "2 mm" spacer 142 (FIG. 14B) attached to the distal end of cover 161 of the apparatus allows an 8 mm insertion depth of hollow needle 14. Thick spacers (e.g., spacer 142 of FIG. 14B) may be configured to decrease the depth of penetration of the hollow needle and may be used for coring thin skin tissues, e.g., skin tissues of the face. Thin spacers (e.g., spacer 141 of FIG. 14A) may be configured to increase the depth of penetration of the hollow needle and may be used for coring thick skin tissues.

Depending on the area of the skin tissue and/or the subject, spacers of different thicknesses may be placed at the distal end of the apparatus (e.g., on the end of a cover attached to the apparatus) to allow different depths of tissue penetration. In some embodiments, a spacer may have a thickness of from about 0.01 mm to about 10 mm (e.g., from 0.1 mm to 10 mm, 0.1 mm to 9.5 mm, 0.1 mm to 9 mm, 0.1 mm to 8.5 mm, 0.1 mm to 8 mm, 0.1 mm to 7.5 mm, 0.1 mm to 7 mm, 0.1 mm to 6.5 mm, 0.1 mm to 6 mm, 0.1 mm to 5.5 mm, 0.1 mm to 5 mm, 0.1 mm to 4.5 mm, 0.1 mm to 4 mm, 0.1 mm to 3.5 mm, 0.1 mm to 3 mm, 0.1 mm to 2.5 mm, 0.1 mm to 2 mm, 0.1 mm to 1.5 mm, 0.1 mm to 1 mm, 0.1 mm to 0.5 mm, 0.1 mm to 10 mm, 0.5 mm to 10 mm, 1 mm to 10 mm, 1.5 mm to 10 mm, 2 mm to 10 mm, 2.5 mm to 10 mm, 3 mm to 10 mm, 3.5 mm to 10 mm, 4 mm to 10 mm, 4.5 mm to 10 mm, 5 mm to 10 mm, 5.5 mm to 10 mm, 6 mm to 10 mm, 6.5 mm to 10 mm, 7 mm to 10 mm, 7.5 mm to 10 mm, 8 mm to 10 mm, 8.5 mm to 10 mm, 9 mm to 10 mm, and 9.5 mm to 10 mm)

Actuation, Translation, and Position Detection Mechanisms

The apparatus may further include actuation mechanisms to drive a hollow needle into or across the skin. In some embodiments, an actuation unit of the apparatus of the invention may include x-, y-, and z-actuators. Alternatively, an actuation unit of the apparatus of the invention (e.g., actuation unit 151 shown in FIGS. 15A and 15B) may include only x- and y-actuators, and a z-actuator (e.g., a voice coil) may be part of the needle assembly of the apparatus (e.g., z-actuator 12 of needle assembly 10 shown in FIGS. 1A-1F). In some embodiments, the "x," "y," and/or "z" actuators may drive a hollow needle into and/or across a large area of skin surface in a relatively short amount of time compared to manual deployment of a hollow needle. In other embodiments, the "x," "y," and/or "z" actuators may drive a hollow needle into and/or across a small area of skin surface (e.g., a small area on the face (e.g., the area between the nose and the upperlip)). In other embodiments, the "x," "y," and/or "z" actuators may drive a hollow needle into and/or across multiple large and/or small areas of skin surface.

A "z" actuator may drive penetration into the skin by a hollow needle and/or retraction of the hollow needle after insertion. In some embodiments, a z-actuator (e.g., a voice coil) is part of the needle assembly of the apparatus (e.g., z-actuator 12 of needle assembly 10 shown in FIGS. 1A-1F) and may be detachably attached to the needle assembly. The apparatus may include a feature or setting that has the ability to control or change the depth of penetration of the hollow needle into the skin. For example, a scroll wheel on a user interface of the base unit may adjust the allowed depth of penetration by the hollow needle by physically retracting the hollow needle and/or providing an electrical signal to a z-actuator. Alternatively, digital controls on the user interface of the base unit may control the depth and/or timing of penetration into and retraction out of the skin by the hollow needle. For example, an operator may program a computer component of the base unit to require a certain displacement of the hollow needle into the skin based upon the area being treated. The z-actuator may be programmed or otherwise set to displace the hollow needle up to about, e.g., 10 mm into thick skin (e.g., on a patient's back or into scar tissue), or about, e.g., 1 mm into thin skin (e.g., on a patient's cheeks), for instance. The z-actuator may be programmed or otherwise set to displace the hollow needle to extend (i) into the dermal layer, (ii) through the entire dermal layer to the junction of the dermal layer and the subcutaneous fat layer, or (iii) into the subcutaneous fat layer.

The z-actuator may also be capable of operating at a high speed to minimize treatment time and deflection of the skin during the penetration of the hollow needle. In some embodiments, one actuation cycle in the z-direction takes from about 5 milliseconds to about 50 milliseconds (e.g., 5, 10, 15, 20, 25, 30, 35, 40, 45, and 50 milliseconds). In some embodiments, the z-actuator takes about 20 to about 35 milliseconds (e.g., 20, 21, 22, 23, 24, 25, 26, 27, 28, 29, 30, 31, 32, 33, 34, and 35 milliseconds) to travel about 20 mm to about 30 mm (e.g., 20, 21, 22, 23, 24, 25, 26, 27, 28, 29, and 30 mm) downward into the skin tissue. In some embodiments, the z-actuator takes about 25 milliseconds to about 30 milliseconds (e.g., 25, 26, 27, 28, 29, and 30 milliseconds) to travel about 23 mm downward into the skin tissue. In some embodiments, the z-actuator takes about 25 to about 35 milliseconds (e.g., 25, 26, 27, 28, 29, 30, 31, 32, 33, 34, and 35 milliseconds (e.g., 30 milliseconds)) to travel about 20 mm to about 30 mm (e.g., 20, 21, 22, 23, 24, 25, 26, 27, 28, 29, and 30 mm (e.g., 23 mm)) upward from a penetration depth of about 20 mm to about 30 mm (e.g., 20, 21, 22, 23, 24, 25, 26, 27, 28, 29, and 30 mm (e.g., 23 mm)) into the skin tissue. In some embodiments, the z-actuator takes about 30 milliseconds to travel about 23 mm upward from the penetrated skin tissue.

The z-actuator may further be capable of operating with relatively high insertion force. In some embodiments, a force of about 0.5 N to about 20 N (e.g., 0.5 N to 0.75 N, 0.5 N to 1 N, 0.5 N to 1.25 N, 0.5 N to 1.5 N, 0.5 N to 2 N, 0.5 N to 5 N, 0.5 N to 10 N, 0.5 N to 12 N, 0.5 N to 15 N, 0.5 N to 20 N, 0.75 N to 1 N, 0.75 N to 1.25 N, 0.75 N to 1.5 N, 0.75 N to 2 N, 0.75 N to 5 N, 0.75 N to 10 N, 0.75 N to 12 N, 0.75 N to 15 N, 0.75 N to 20 N, 1 N to 1.25 N, 1 N to 1.5 N, 1 N to 2 N, 1 N to 5 N, 1 N to 10 N, 1 N to 12 N, 1 N to 15 N, 1 N to 20 N, 1.25 N to 1.5 N, 1.25 N to 2 N, 1.25 N to 5 N, 1.25 N to 10 N, 1.25 N to 12 N, 1.25 N to 15 N, 1.25 N to 20 N, 1.5 N to 2 N, 1.5 N to 5 N, 1.5 N to 10 N, 1.5 N to 12 N, 1.5 N to 15 N, 1.5 N to 20 N, 2 N to 5 N, 2 N to 10 N, 2 N to 12 N, 2 N to 15 N, 2 N to 20 N, 5 N to 10 N, 5 N to 12 N, 5 N to 15 N, 5 N to 20 N, 10 N to 12 N, 10 N to 15 N, 10 N to 20 N, 12 N to 15 N, 12 N to 20 N, and 15 N to 20 N) per hollow needle can be applied to ensure insertion of the hollow needle into the skin. In some embodiments, a force of about 10 N to 20 N (e.g., 15 N) per hollow needle can be applied to ensure insertion of the hollow needle into the skin. The insertion force may be inversely correlated with needle gauge. For example, a 24 gauge needle may be operated with an insertion force of 12 N, while a 20 gauge needle may be operated with a higher insertion force. The z-actuator may also be capable of maintaining the apparatus at a low temperature (e.g., less than about 43° C., such as less than about 43, 42, 41, 40, 39, 38, 37, 36, or 35° C.) to avoid patient and user discomfort and/or to avoid damage to the skin tissue (e.g., collagen in the skin tissue is sensitive to high temperatures). Actuator types having these characteristics include voice coil (VC) actuators, pneumatic actuators, electromagnetic actuators, motors with cams, motors with lead screws (e.g., stepper motors), and piezoelectric actuators. In some embodiments, the z-actuator is a VC actuator.

The apparatus may include an "x" and/or "y" actuator for translating a hollow needle across the skin. The x/y-actuator may be used to establish the skin treatment coverage. In some embodiments, the x/y-actuator may be characterized by a small displacement range (e.g., less than about 10 mm (e.g., 10, 9, 8, 7, 6, 5, 4, 3, 2, and 1 mm)). In some embodiments, the x/y-actuator may be characterized by a relatively large displacement range (e.g., up to about 30 mm). The x/y-actuator may operate with high positional accuracy. For example, x/y-actuator may position the hollow needle to penetrate the skin within a 30 µm radius (e.g., within 30, 25, 20, 15, 10, or 5 µm) of a selected position. The x/y-actuator may operate with high position accuracy that allows continuous treatment across a treatment area. A treatment area may be a skin area that contains multiple treatment sites, e.g., a 3 cm by 3 cm treatment area containing nine 1 cm² treatment sites. The x/y-actuator may facilitate movement of the hollow needle(s) of the apparatus from one treatment site to the adjacent treatment site within the treatment area. The x/y-actuator may also facilitate movement of the hollow needle(s) of the apparatus within each treatment site. The x/y-actuator may operate with high position accuracy that avoid gaps between adjacent treatment sites in the treatment area and/or avoid overlaps between adjacent treatment sites in the treatment area.

The x/y-actuator may also operate at a relatively high speed to minimize treatment time. In some embodiments, one actuation cycle in the x- and/or y-direction takes from about 50 milliseconds to about 250 milliseconds (e.g., 50, 75, 100, 125, 150, 175, 200, 225, and 250 milliseconds). In some embodiments, one actuation cycle in the x- and/or y-direction takes about 120 milliseconds to about 160 milliseconds (e.g., 120, 125, 130, 135, 140, 145, 150, 155, and 160 milliseconds (e.g., about 140 milliseconds)). In some embodiments, one actuation cycle in the x- and/or y-direction takes about 120 milliseconds to about 160 milliseconds (e.g., 120, 125, 130, 135, 140, 145, 150, 155, and 160 milliseconds (e.g., about 140 milliseconds)) to travel about 0.6 mm to about 1 mm (e.g., 0.6, 0.65, 0.7, 0.75, 0.8, 0.85, 0.9, 0.95, and 1 mm). In some embodiments, one actuation cycle in the x- and/or y-direction takes about 140 milliseconds to travel about 0.833 mm.

In some embodiments, the x/y-actuator may be capable of operating with a force of about 0.5 N to about 20 N (e.g., 0.5 N to 0.75 N, 0.5 N to 1 N, 0.5 N to 1.25 N, 0.5 N to 1.5 N, 0.5 N to 2 N, 0.5 N to 5 N, 0.5 N to 10 N, 0.5 N to 12 N, 0.5 N to 15 N, 0.5 N to 20 N, 0.75 N to 1 N, 0.75 N to 1.25 N, 0.75 N to 1.5 N, 0.75 N to 2 N, 0.75 N to 5 N, 0.75 N to 10 N, 0.75 N to 12 N, 0.75 N to 15 N, 0.75 N to 20 N, 1 N to 1.25 N, 1 N to 1.5 N, 1 N to 2 N, 1 N to 5 N, 1 N to 10 N, 1 N to 12 N, 1 N to 15 N, 1 N to 20 N, 1.25 N to 1.5 N, 1.25 N to 2 N, 1.25 N to 5 N, 1.25 N to 10 N, 1.25 N to 12 N, 1.25 N to 15 N, 1.25 N to 20 N, 1.5 N to 2 N, 1.5 N to 5 N, 1.5 N to 10 N, 1.5 N to 12 N, 1.5 N to 15 N, 1.5 N to 20 N, 2 N to 5 N, 2 N to 10 N, 2 N to 12 N, 2 N to 15 N, 2 N to 20 N, 5 N to 10 N, 5 N to 12 N, 5 N to 15 N, 5 N to 20 N, 10 N to 12 N, 10 N to 15 N, 10 N to 20 N, 12 N to 15 N, 12 N to 20 N, and 15 N to 20 N) per hollow needle can be applied to translate the needle across the skin. In some embodiments, a force of about 5 N to 15 N (e.g., 10 N) per hollow needle can be applied to translate the needle across the skin. The x/y-actuator may also be capable of operating at a low temperature (e.g., less than about 43° C., such as less than about 43, 42, 41, 40, 39, 38, 37, 36, or 35° C.) in order to avoid raising the apparatus temperature to a level that could cause patient discomfort. Actuator types having these characteristics include voice coil (VC) actuators, pneumatic actuators, electromagnetic actuators, motors with cams, piezoelectric actuators, and motors with lead screws (e.g., stepper motors). In some embodiments, the x/y-actuator is a stepper motor with a lead screw.

In any of the apparatuses, one or more components of the apparatus may be selected or designed to secure the one or more hollow needles and/or prevent or minimize angular movement (e.g., wobbling) of the hollow needle(s). In some embodiments, the x-, y-, and/or z-actuator may be capable of operating without causing any significant angular movement (e.g., wobbling) of the hollow needle(s). In particular embodiments, the z-actuator may be capable of inserting and withdrawing the hollow needle(s) in a linear fashion without any significant angular movement (e.g., wobbling) of the hollow needle(s). The hollow needle(s) may be secured to the needle assembly so as to minimize or reduce angular movement of the needle(s) during insertion to less than 5 degrees, e.g., less than 4, 3, or 2 degrees. An angular movement of the needle(s) during insertion of ~1-1.5 degrees is within nominal tolerances, whereas an angular movement of the needle(s) during insertion of ~4-5 degrees or more is to be avoided, if possible. For example, components that join hollow needle(s) to other components of the needle assembly may be designed with low mechanical tolerances to firmly secure the hollow needle(s). This may reduce the prevalence of or lower the risk of destabilization and/or reduction in the structural integrity of hollow needle(s) that may result from repeated use. For example, firmly securing the needle(s) may prevent and/or minimize dulling, bending, and curling of needle tip(s) that could reduce the effectiveness of the needle(s). Firmly securing the needle(s) may also reduce the risk of over-striking (e.g., striking a hole produced by a needle more than once).

Figure 15B:
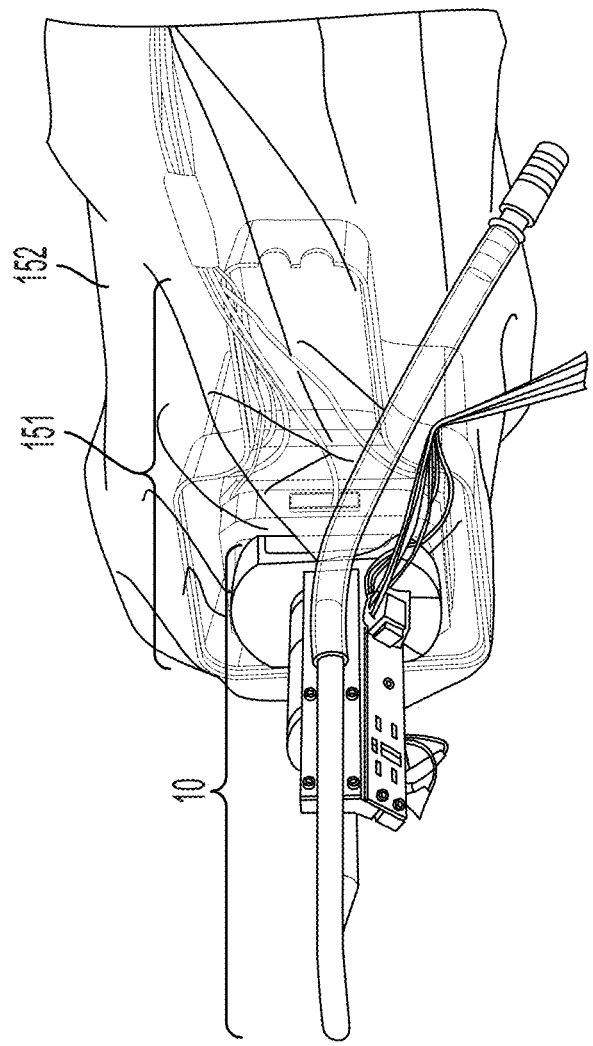
FIG. 15B is a photograph showing a needle assembly of the invention connected to an actuation unit.
Figure 15A:
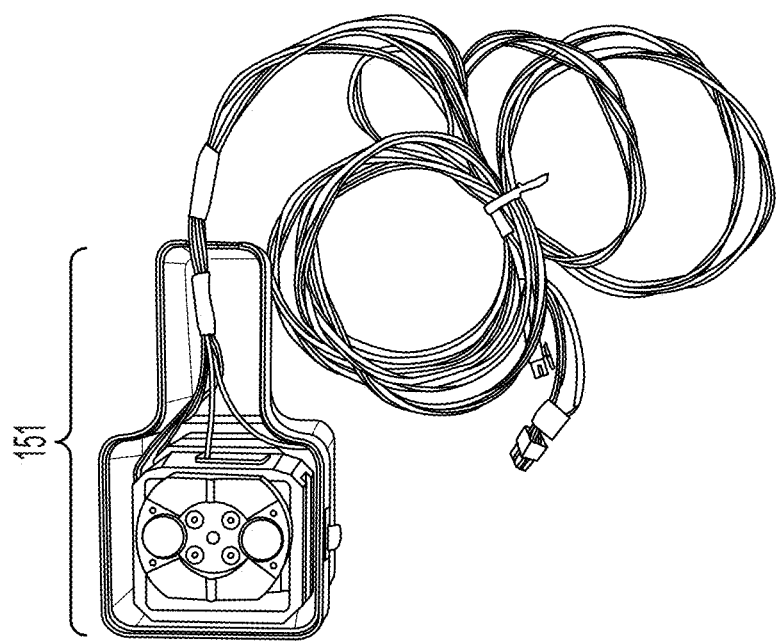
FIG. 15A is a photograph showing an actuation unit including x- and y-actuators.

An actuation unit having an x-, y-, and/or z-actuator may be integrated into the apparatus or may be detachably connected to the needle assembly of the apparatus (e.g., needle assembly 10 show in FIGS. 1A-1F, 15B, and 16G-16U). FIG. 15A shows actuation unit 151 including x- and y-actuators that may be detachably attached to needle assembly 10 of the apparatus. FIG. 15B shows needle assembly 10 of the invention connected to actuation unit 151, which is covered in drape 152 to maintain sterility and/or cleanness during the treatment process and to protect actuation unit 151, as well as the treatment area, from contamination. In some embodiments, the actuation unit (if external to the apparatus; actuation unit 151) may be connected to the support base of the needle assembly (e.g., support base 11 of needle assembly 10 shown in FIGS. 1A-1F). In some embodiments, the actuation unit (e.g., actuation unit 151) and the support base (e.g., support base 11) may be connected by establishing a vacuum connection. In other embodiments, the actuation unit (e.g., actuation unit 151) and the support base (e.g., support base 11) may be connected by establishing a magnetic connection. In other embodiments, the actuation unit (e.g., actuation unit 151) and the support base (e.g., support base 11) may be connected by establishing a mechanical connection using, e.g., quick-connect clasps. The actuation unit-support base connecting mechanism may be detachably engaged for easy and quick connection and disconnection. The actuation unit-support base connecting mechanism may include one or more of adhesive, magnetic, electrical, and/or mechanical components (e.g., one or more gaskets, o-rings, septa, springs, clasps, and other engagement members). Various locking and connecting mechanisms that may be used to couple an actuation unit (e.g., actuation unit 151) to a needle assembly of the apparatus (e.g., to a support base of a needle assembly (e.g., support base 11 of needle assembly 10 shown in FIGS. 1A-1F)) are shown in FIGS. 17A-17I, 18A-18C, 19A-19C, 20A-20E, 21A-21D, and 22A-22D and described in detail further herein.

Figure 16B:
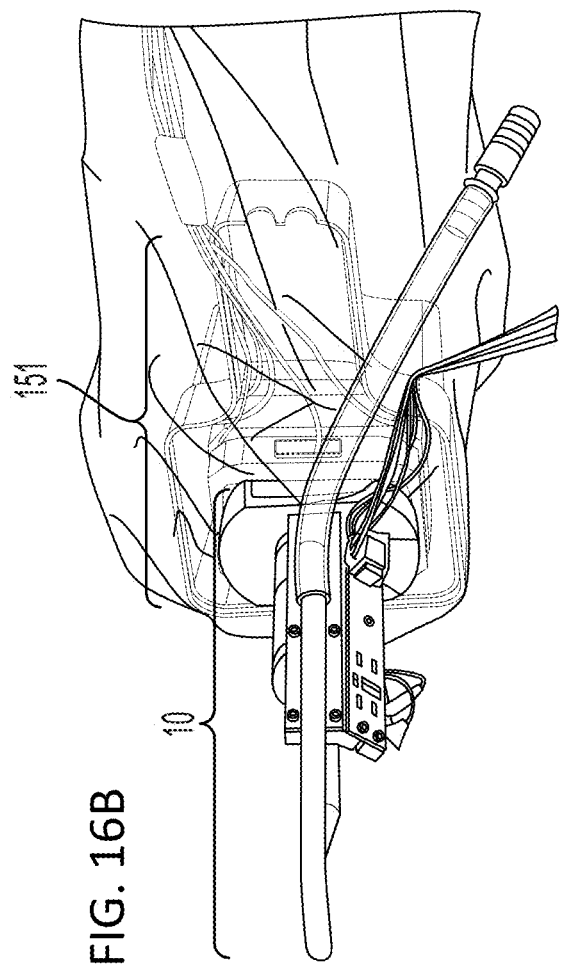
FIGS. 16B and 16C are photographs showing a needle assembly of the invention connected to an actuation unit before (FIG. 16B) and after (FIG. 16C) the needle assembly and the actuation unit are enclosed by the cover shown in FIG. 16A.
Figure 16C:
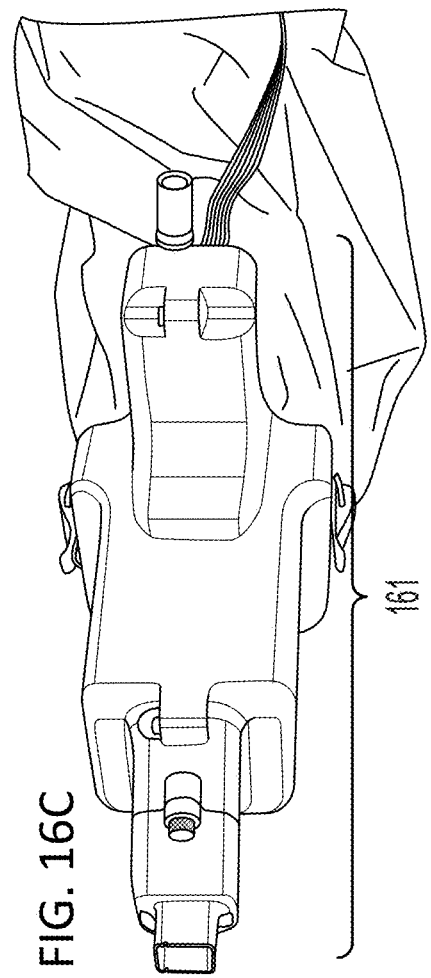
Figure 16A:
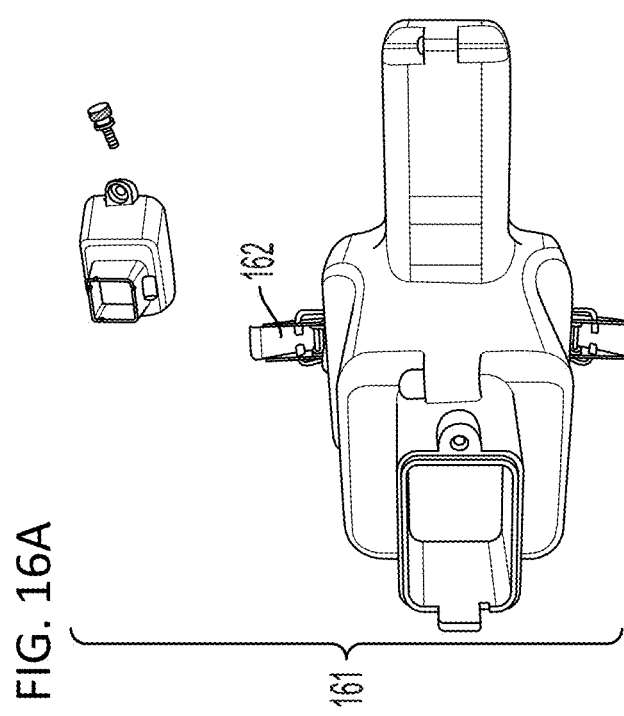
FIG. 16A is a photograph showing a cover used to enclose a needle assembly of the invention and an actuation unit.
Figure 16D:
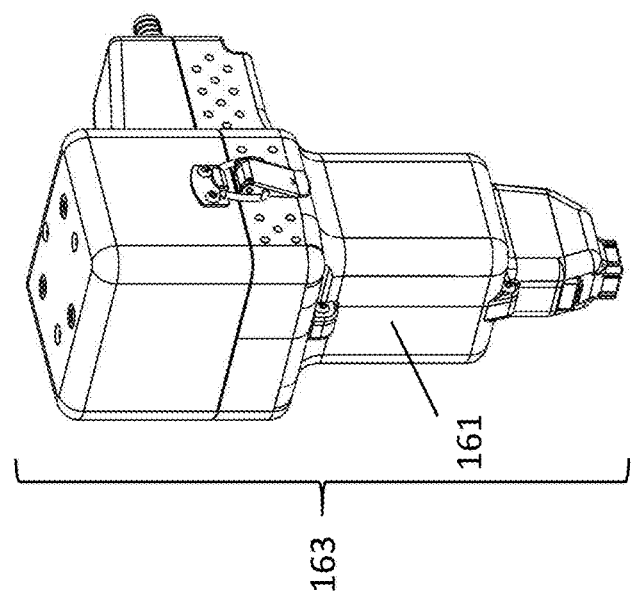
FIGS. 16D, 16E, and 16F are schematic illustrations showing three perspective views of an apparatus of the invention including a cover that encloses a needle assembly and an actuation unit.
Figure 16E:
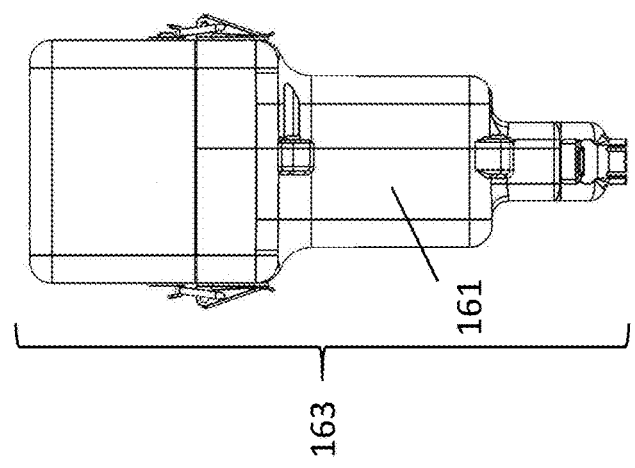
Figure 16F:
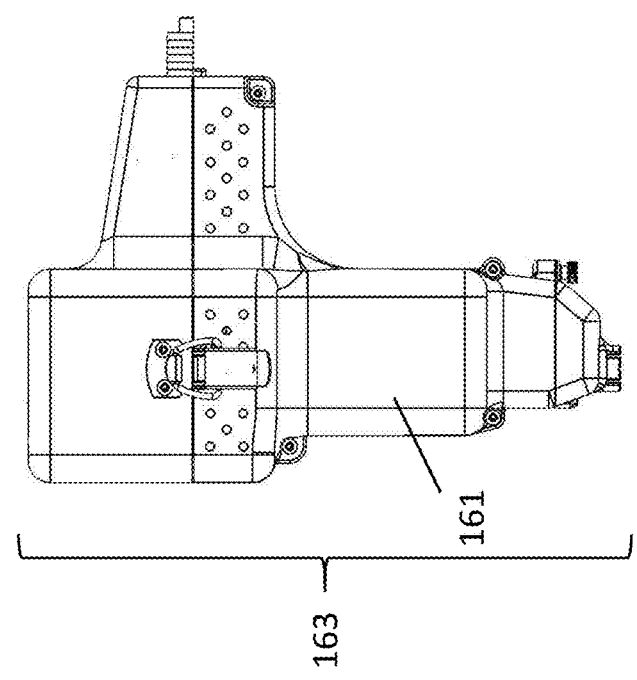
Figure 16I:
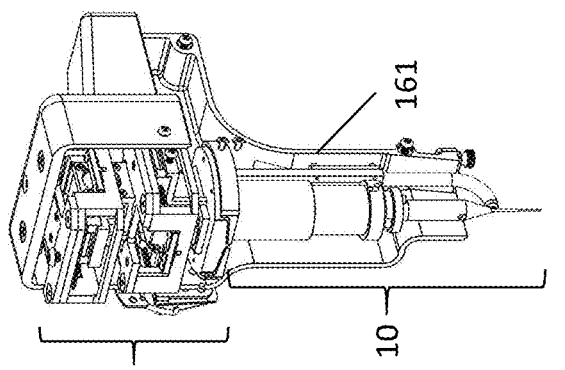
FIGS. 16G, 16H, and 16I are schematic illustrations showing three cross-sectional views of an apparatus of the invention including a cover that encloses a needle assembly and an actuation unit.
Figure 16H:
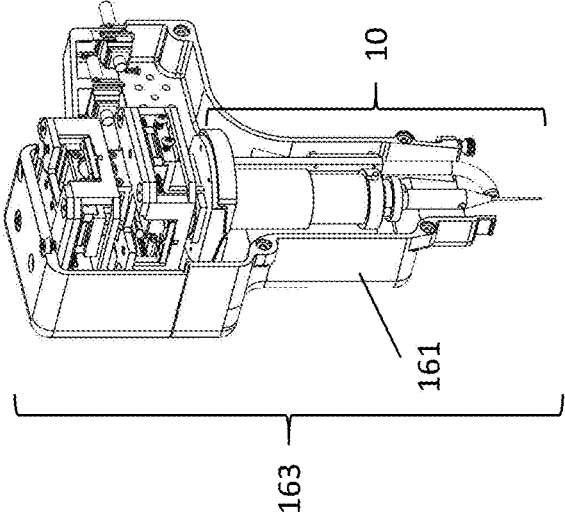
Figure 16G:
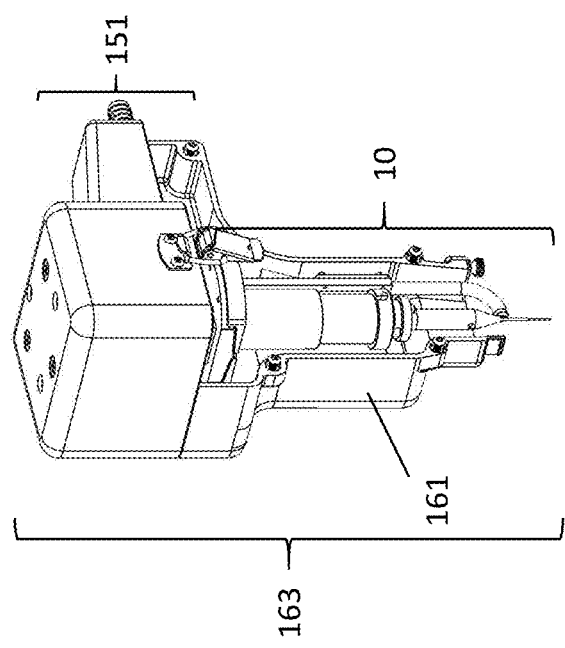
Figure 16Q:
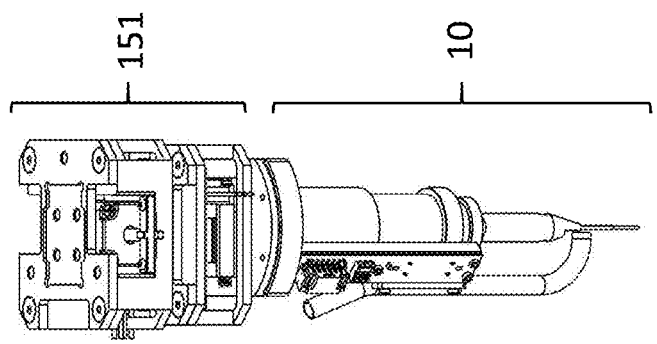
Figure 16P:
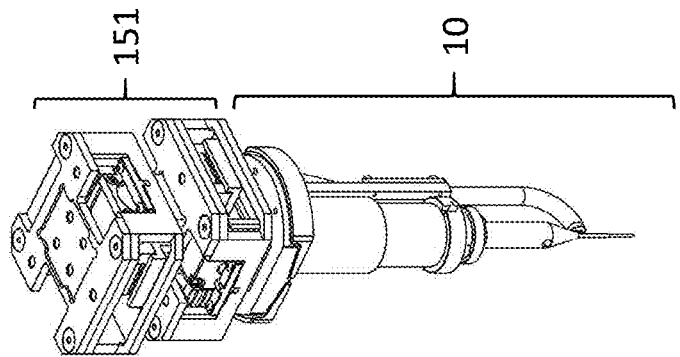
Figure 16O:
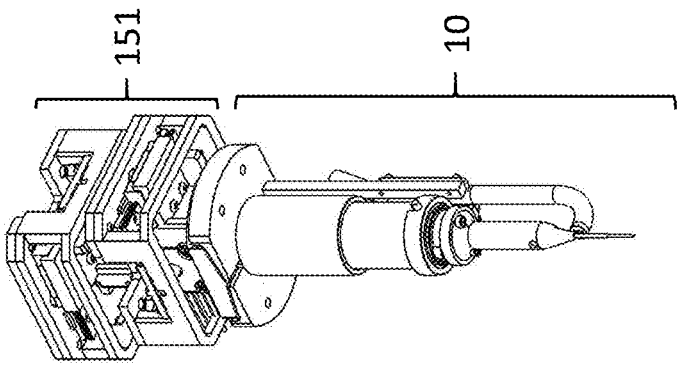
Figure 16R:
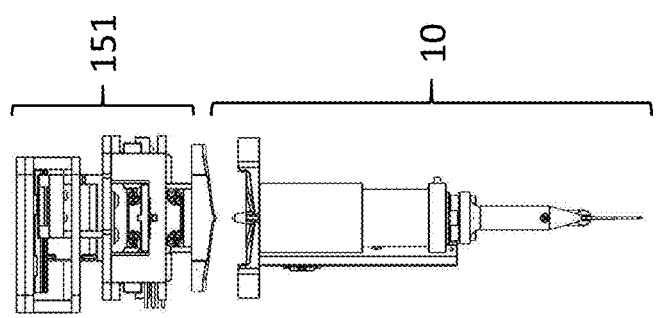
FIGS. 16R, 16S, 16T, and 16U are exploded views showing four views of the inside of an apparatus of the invention including a needle assembly and an actuation unit, which are detached.
Figure 16S:
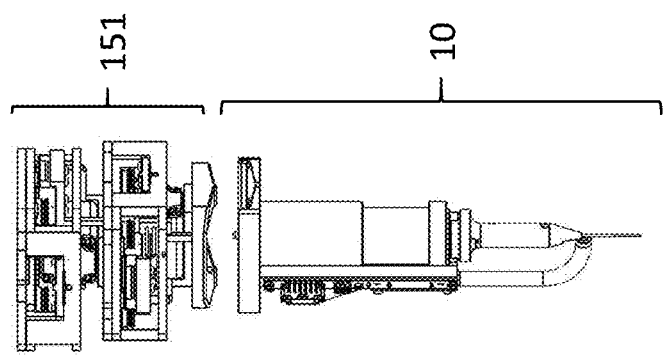
Figure 16T:
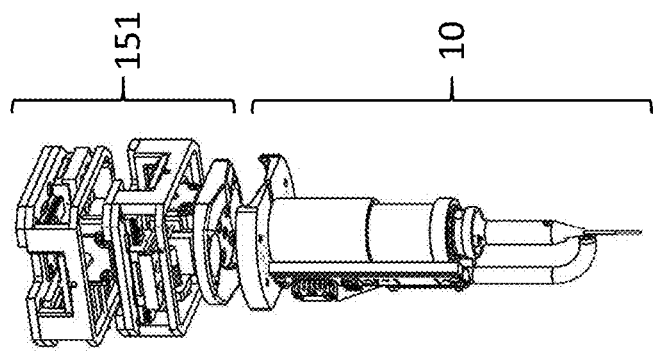
Figure 16U:
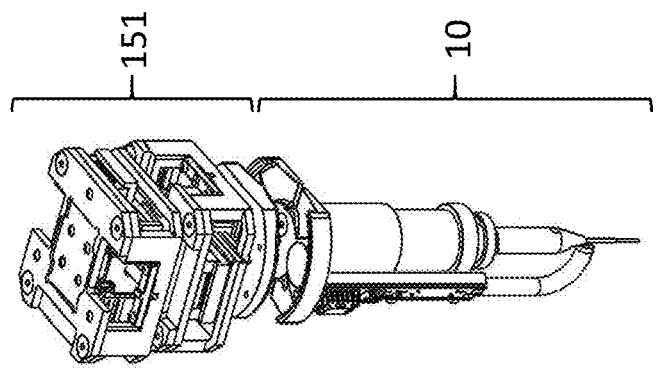

In some embodiments, an actuation unit (e.g., actuation unit 151) and a needle assembly of the invention (needle assembly 10 shown in FIGS. 1A-1F, 16B, 16C, and 16G-16U) may be optionally enclosed in a cover, which may be used to keep the actuation unit and the needle assembly sterile. FIG. 16A shows an example of a cover, e.g., cover 161. Cover 161 includes quick-connect clasps 162 that may be used to establish a mechanical connection to the actuation unit (e.g., actuation unit 151) and the needle assembly of the invention (needle assembly 10 shown in FIGS. 1A-1F, 16B, 16C, and 16G-16U). FIGS. 16B and 16C show needle assembly 10 connected to actuation unit 151 before (FIG. 16A) and after (FIG. 16B) the needle assembly and the actuation unit are enclosed in by cover 161. Additionally, FIGS. 16D-16F show three views of apparatus 163 including a cover (e.g., cover 161), which encloses a needle assembly (e.g., needle assembly 10) and an actuation unit (e.g., actuation unit 151). FIGS. 16G-16I show cross-sectional views of the inside of apparatus 163. FIGS. 16J-16Q show needle assembly 10 connected to actuation unit 151. FIGS. 16R-16U show disassembled needle assembly 10 and actuation unit 151. Other connecting/sealing/enclosing options (e.g., a magnetic connection) are also available to engage a cover of the apparatus (e.g., cover 161).

The z-, x-, and y-actuators may be activated independently or together by one or more buttons, keys, toggles, switches, screws, dials, cursors, spin-wheels, or other components. In some embodiments, each of the z-, x-, and y-actuators can be separately controlled (e.g., using separate activation components, such as a button, or by using separate controls in a user interface).

The apparatus may further include a translation mechanism to drive the entire apparatus across the skin (e.g., x- and y-translation). A translation mechanism may include, e.g., driving wheels or rods. A translation mechanism may permit automatic or manual translation of the apparatus across the skin. Translating components (e.g., wheels) may be disposed on the apparatus or be disposed external to the apparatus. The translating mechanism may be activated by an activator, such as a button, key, toggle, switch, screw, cursor, dial, spin-wheel, or other component, and/or may be digitally controlled by a user interface.

The apparatus may also include a position detection mechanism, such as an optical tracking mechanism. A position detection mechanism (e.g., a camera, infrared sensor, photodiode, and LED and detector) may assist in tracking movement of the apparatus in relation to a patient or a treatment area. The optical tracking mechanism may also facilitate placement of the hollow needle on the skin surface in the instance of manual translation of the apparatus across the skin. Control electronics for a position detection mechanism may be disposed within the apparatus or external to the apparatus, e.g., in a base unit or separate computer. For example, the position detection mechanism may monitor the distance between the previous needle insertion and the current apparatus position and send a signal to the control electronics to actuate the skin penetration mechanism when the apparatus has reached the desired position (e.g., a position a defined distance from the position where the needles were last inserted). Desired distances and/or positions may be controlled at user interface.

The apparatus may also include a guide or template to facilitate the positioning of the hollow needle of the apparatus. A guide or template may contain one or more holes or openings that provide a pre-set array pattern (described further herein) for the hollow needle of an apparatus of the invention to follow. The guide or template may be used alone or in combination with the position detection mechanism. The hollow needle may be translated by the x- and/or y-actuators to move across the guide or template and follow the array pattern set by the guide or the template to remove skin tissue portions at the holes or openings in the guide or template.

Locking or Connecting Mechanisms

A locking or connecting mechanism may be used to couple components and units described herein, e.g., coupling of an actuation unit (e.g., actuation unit 151) to a support base of the needle assembly (e.g., support base 11) and coupling of an actuation unit (e.g., actuation unit 151) to a cover of the apparatus (e.g., cover 161). A locking or connecting mechanism may be established by a vacuum connection, a magnetic connection, and/or a mechanical connection (e.g., using quick-connect clasps). A locking or connecting mechanism used to couple adjacent components or units described herein may be detachably engaged for easy and quick connection and disconnection. A locking or connecting mechanism may include one or more of adhesive, magnetic, electrical, and/or mechanical components (e.g., one or more gaskets, o-rings, septa, springs, clasps, and other engagement members).

Figure 18C:
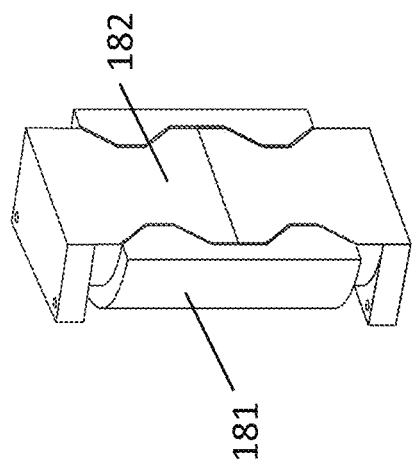
FIGS. 18A, 18B, and 18C are schematic illustrations showing three views of a compression clamp having parts 181 and 182.
Figure 18B:
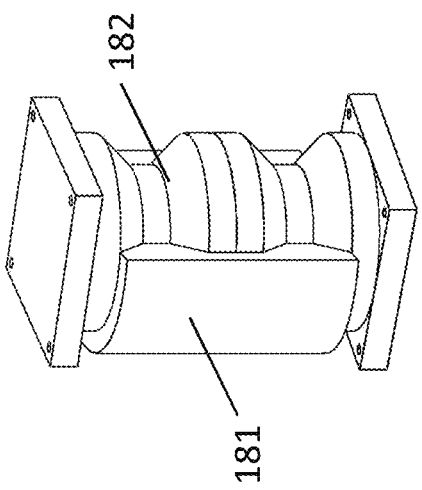
Figure 18A:
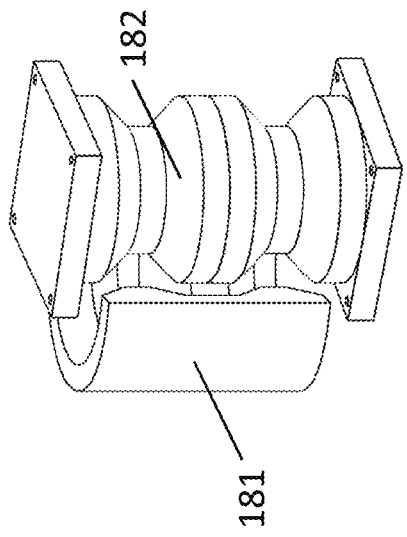
Figure 19A:
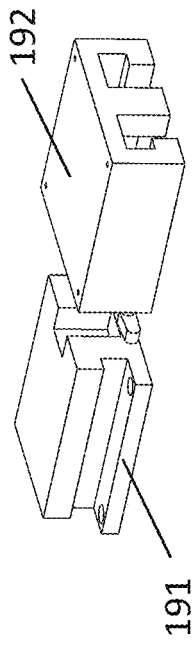
FIGS. 19A, 19B, and 19C are schematic illustrations showing three views of a sliding clamp having parts 191 and 192.
Figure 19B:
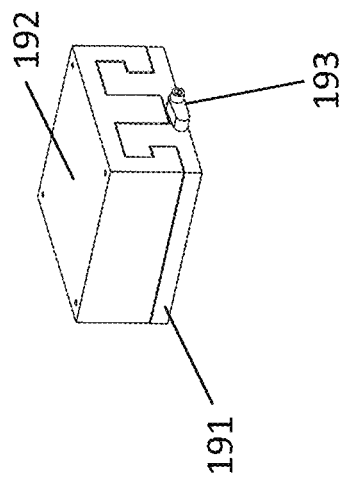
Figure 19C:
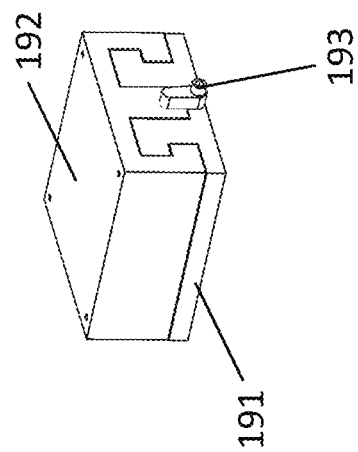
Figure 20C:
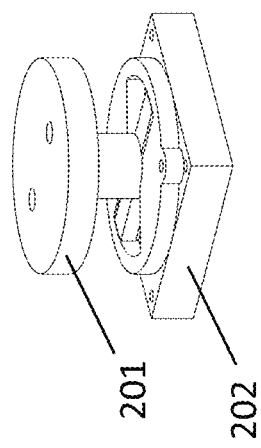
FIGS. 20A, 20B, and 20C are schematic illustrations showing three views of a rotating lock having parts 201 and 202.
Figure 20B:
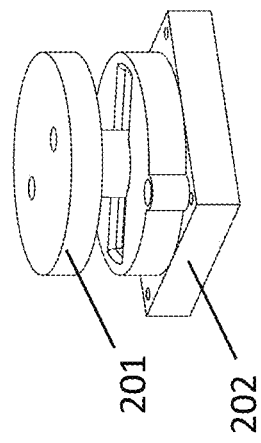
Figure 20A:
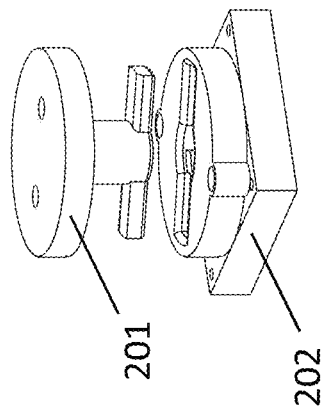
Figure 20E:
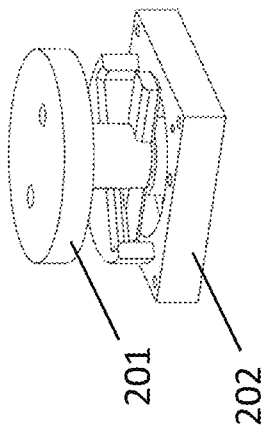
FIGS. 20D and 20E are schematic illustrations showing two cross-sectional views of a rotating lock having parts 201 and 202.
Figure 20D:
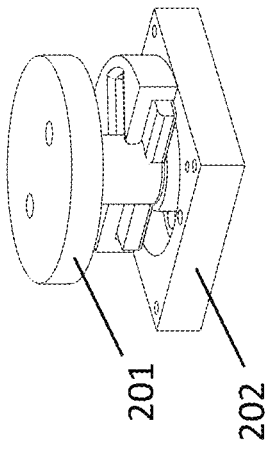
Figure 22A:
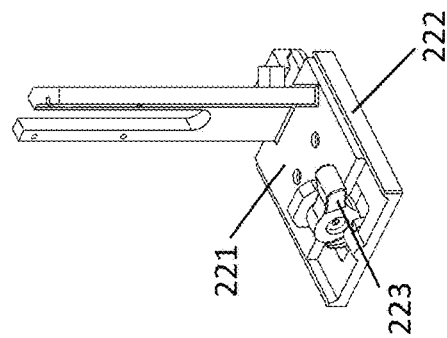
FIGS. 22A, 22B, 22C, and 22D are schematic illustrations showing four views of a sliding-rotating lock having parts 221 and 222.
Figure 22B:
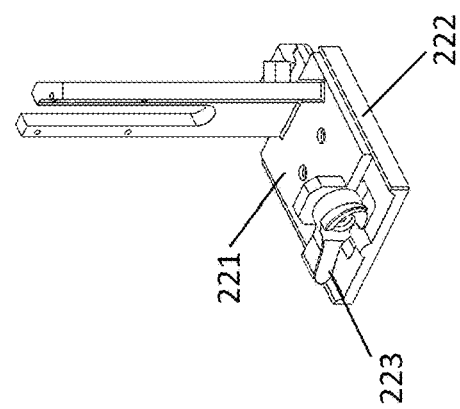
Figure 22C:
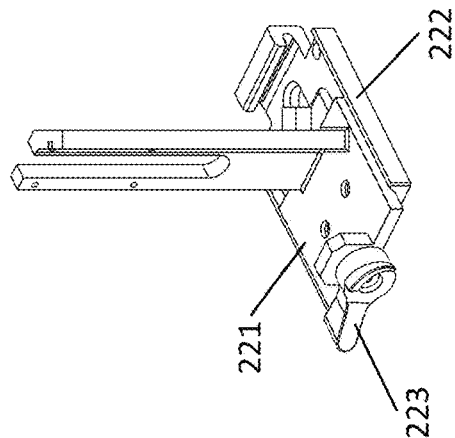
Figure 22D:
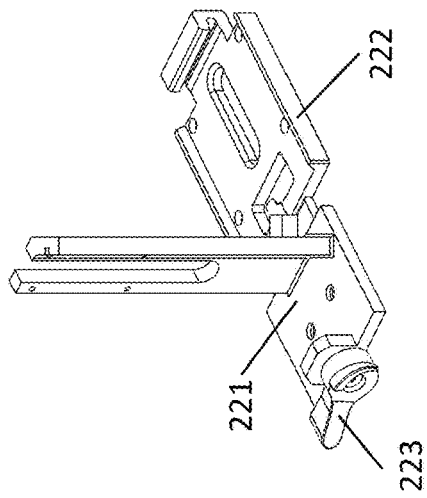

Various locking or connecting mechanisms are shown in FIGS. 17A-17I, 18A-18C, 19A-19C, 20A-20E, 21A-21D, and 22A-22D and described in detail further herein. FIGS. 17A-17D show four views of a magnetic latch having parts 171 and 172. FIGS. 17A and 17B show disassembled parts 171 and 172 of the magnetic latch; FIGS. 17C and 17D show assembled parts 171 and 172 of the magnetic latch; FIGS. 17E and 17F show two cross-sectional views of the assembled magnetic latch; FIG. 17G shows the section of part 171 that is to be connected to part 172; and FIGS. 17H and 17I show two views of part 172 of the magnetic latch. FIGS. 18A-18C show three views of a compression clamp having parts 181 and 182. FIG. 18A shows disassembled parts 181 and 182 of the compression clamp; FIG. 18B shows parts 181 and 182 assembled to form the compression clamp; and FIG. 18C shows a cross-sectional view of the assembled compression clamp. FIGS. 19A-19C show three views of a sliding clamp having parts 191 and 192. FIG. 19A shows disassembled parts 191 and 192 of the sliding clamp; FIG. 19B shows parts 191 and 192 assembled to form the sliding clamp having clamp-lock switch 193 in the unlocked position; and FIG. 19C shows parts 191 and 192 assembled to form the sliding clamp having clamp-lock switch 193 in the locked position. FIGS. 20A-20E show five views of a rotating lock having parts 201 and 202. FIG. 20A shows disassembled parts 201 and 202 of the rotating lock; FIG. 20B shows parts 201 and 202 assembled to form the rotating lock in the unlocked position; FIG. 20C shows parts 201 and 202 assembled to form the rotating lock in the locked position; and FIGS. 20D and 20E show two cross-sectional views of the rotating lock in the locked position. FIGS. 21A-21D shows four views of a clasp latch having parts 211 and 212. FIG. 21A shows parts 211 and 212 assembled to form the clasp latch having lock clip 213 in the unlocked position; FIGS. 21B and 21C show two views of parts 211 and 212 assembled to form the clasp latch having lock clip 213 in the locked position; and FIG. 21D shows a cross-sectional view of the assembled clasp latch having lock clip 213 in the locked position. FIGS. 22A-22D show four views of a sliding-rotating lock having parts 221 and 222. FIG. 22A shows disassembled parts 221 and 222 of the sliding-rotating lock; FIGS. 22B and 22C show parts 221 and 222 partly and fully assembled to form the sliding-rotating lock having slide-lock switch 223 in the unlocked position; and FIG. 22D shows parts 221 and 222 assembled to form the sliding-rotating lock having slide-lock switch 223 in the locked position.

To use a locking or connecting mechanism shown in any one of FIGS. 17A-17I, 18A-18C, 19A-19C, 20A-20E, 21A-21D, and 22A-22D to couple two adjacent components or units, the first part of the locking or connecting mechanism may be attached to one component or unit and the second part of the locking or connecting mechanism may be attached to the adjacent component or unit. Alternatively, a component or unit of the apparatus may be functionalized as a part of the locking or connecting mechanism. For example, an actuation unit (e.g., actuation unit 151) may be attached to part 171 shown in any one of FIGS. 17A-17F and a support base of a needle assembly (e.g., support base 11 of needle assembly 10 shown in FIGS. 1A-1F) may be functionalized as part 172 shown in any one of FIGS. 17A-17F. Accordingly, a magnetic latch may be formed to lock the actuation unit (e.g., actuation unit 151) with the support base of a needle assembly (e.g., support base 11).

Array Patterns

The one or more hollow needles of the apparatus may be configured to form an array pattern in the skin upon removal of the portions of the skin tissue. The array pattern may include holes in one or more rows or in a semi-random spatial distribution. The size and geometry of an array pattern may be generated based on the area of skin and condition being treated. For example, a small array pattern may be generated for treatment of the peri-oral area, while a large array pattern may be suitable for treatment of the abdomen. In some embodiments, an array pattern may be generated using different numbers and/or arrangements of a plurality of hollow needles. In some embodiments, an array pattern may be generated using one hollow needle, which can undergo multiple actuation cycles and be translated across the surface of the skin region by the x-actuator and/or y-actuator to generate the array pattern. In some embodiments, an array pattern may be generated using a plurality of hollow needles (e.g., an array of hollow needles), which can undergo one or more actuation cycles to generate the array pattern. The number of actuation cycles needed to generate an array pattern of holes in the skin tissue is determined by the size of the array pattern, the gauge or inner diameter of the hollow needle, the number of hollow needles, and the amount of skin tissue to be removed, e.g., the areal fraction of skin tissue removed. An "areal fraction" of tissue removed refers to the fraction of the skin tissue surface covered by the holes generated by the hollow needle(s) of the apparatus. In other words, an areal fraction of tissue removed refers to the ratio of the area covered by the total amount of cored tissue portions to the total skin treatment area. In one embodiment, one or more hollow needles may be configured to remove an areal fraction of about 0.01 to about 0.65 (e.g., 0.01, 0.02, 0.03, 0.04, 0.05, 0.10, 0.15, 0.20, 0.25, 0.30, 0.35, 0.40, 0.45, 0.50, 0.55, 0.60, and 0.65) of tissue within a treatment area. In another embodiment, one or more hollow needles may be configured to remove an areal fraction of less than about 0.1, such as about 0.01 to about 0.05 (e.g., 0.01, 0.015, 0.02, 0.025, 0.03, 0.035, 0.04, 0.045, and 0.05) of tissue within a treatment area. In another embodiment, one or more hollow needles may be configured to remove an areal fraction of about 0.02 to about 0.03 (e.g., 0.02, 0.021, 0.022, 0.023, 0.024, 0.025, 0.026, 0.027, 0.028, 0.029, and 0.03, e.g., 0.025) of tissue within a treatment area. In some embodiments, an areal fraction of about 0.01 to about 0.65 (e.g., 0.01, 0.02, 0.03, 0.04, 0.05, 0.10, 0.15, 0.20, 0.25, 0.30, 0.35, 0.40, 0.45, 0.50, 0.55, 0.60, and 0.65) of tissue may be removed within a treatment area for wrinkle reduction. In some embodiments, an areal fraction of about 0.02 to about 0.03 (e.g., 0.02, 0.021, 0.022, 0.023, 0.024, 0.025, 0.026, 0.027, 0.028, 0.029, and 0.03, e.g., 0.025) of tissue may be removed within a treatment area for wrinkle reduction. Table 3 below shows the number of actuation cycles required for the treatment of different body areas using a 24 gauge hollow needle.

TABLE 3

| Treatment Site | Total Treatment Area (cm$^2$) | Areal Fraction of Tissue Removed | Number of Actuation Cycles |
|---|---|---|---|
| Cheek | 120 | 0.1 | 15,782 |
| Upper lip | 10 | 0.1 | 1,315 |
| Knee | 120 | 0.1 | 15,782 |
| Hand | 100 | 0.1 | 13,151 |

The apparatus may be configured for detachable attachment to one or more hollow needles having the same or different configurations. The apparatus may have as few as 1 or as many as hundreds of hollow needles. In some embodiments, 1-100 hollow needles may be present (e.g., 1-10, 1-20, 1-30, 1-40, 1-50, 1-60, 1-70, 1-80, 1-90, 1-100, 3-10, 3-20, 3-30, 3-40, 3-50, 3-60, 3-70, 3-80, 3-90, 3-100, 5-10, 5-20, 5-30, 5-40, 5-50, 5-60, 5-70, 5-80, 5-90, 5-100, 10-20, 10-40, 10-60, 10-80, 10-100, 20-40, 20-60, 20-80, 20-100, 40-60, 40-80, 40-100, 60-80, 60-100, or 80-100 hollow needles). The use of an array of a plurality of hollow needles to generate an array pattern may facilitate skin treatment over larger areas and in less time.

The minimum distance between two hollow needles in an array of hollow needles may be between about 0.1 mm to about 50 mm (e.g., from 0.1 mm to 0.2 mm, 0.1 mm to 0.5 mm, 0.1 mm to 1 mm, 0.1 mm to 2 mm, 0.1 mm to 5 mm, 0.1 mm to 10 mm, 0.1 mm to 15 mm, 0.1 mm to 20 mm, 0.1 mm to 30 mm, 0.1 mm to 40 mm, 0.1 mm to 50 mm, 0.2 mm to 0.5 mm, 0.2 mm to 1 mm, 0.2 mm to 2 mm, 0.2 mm to 5 mm, 0.2 mm to 10 mm, 0.2 mm to 15 mm, 0.2 mm to 20 mm, 0.2 mm to 30 mm, 0.2 mm to 40 mm, 0.2 mm to 50 mm, 0.5 mm to 1 mm, 0.5 mm to 2 mm, 0.5 mm to 5 mm, 0.5 mm to 10 mm, 0.5 mm to 15 mm, 0.5 mm to 20 mm, 0.5 mm to 30 mm, 0.5 mm to 40 mm, 0.5 mm to 50 mm, 1 mm to 2 mm, 1 mm to 5 mm, 1 mm to 10 mm, 1 mm to 15 mm, 1 mm to 20 mm, 1 mm to 30 mm, 1 mm to 40 mm, 1 mm to 50 mm, 2 mm to 5 mm, 2 mm to 10 mm, 2 mm to 15 mm, 2 mm to 20 mm, 2 mm to 30 mm, 2 mm to 40 mm, 2 mm to 50 mm, 5 mm to 10 mm, 5 mm to 15 mm, 5 mm to 20 mm, 5 mm to 30 mm, 5 mm to 40 mm, 5 mm to 50 mm, 10 mm to 15 mm, 10 mm to 20 mm, 10 mm to 30 mm, 10 mm to 40 mm, 10 mm to 50 mm, 15 mm to 20 mm, 15 mm to 30 mm, 15 mm to 40 mm, 15 mm to 50 mm, 20 mm to 30 mm, 20 mm to 40 mm, 20 mm to 50 mm, 30 mm to 40 mm, 30 mm to 50 mm, and 40 mm to 50 mm). In some embodiments, the distance between two hollow needles in an array of hollow needles is less than about 15 mm. The minimum distance may correspond to the minimal size of an array pattern, while the maximum distance may correspond to the maximum size of an array pattern.

Array patterns of different sizes and geometries may be generated based on the area of treatment and the skin condition being treated. Array patterns may also be generated for compatibility with actuation mechanisms and control electronics of a given apparatus. Alternatively, actuation mechanisms and control electronics of an apparatus may be selected for compatibility with a desired array pattern size and/or geometry. For example, a long, linear array pattern may be generated using a translating mechanism with driving wheels, while a large, rectangular array may be generated using an x- and/or y-actuator to drive the hollow needle(s) across the skin.

In any of the apparatuses, one or more hollow needles may be configured to provide from about 10 to about 10000 cored tissue portions or more per cm$^2$ area (e.g., 10 to 50, 10 to 100, 10 to 200, 10 to 300, 10 to 400, 10 to 500, 10 to 600, 10 to 700, 10 to 800, 10 to 900, 10 to 1000, 10 to 2000, 10 to 4000, 10 to 6000, 10 to 8000, 10 to 10000, 50 to 100, 50 to 200, 50 to 300, 50 to 400, 50 to 500, 50 to 600, 50 to 700, 50 to 800, 50 to 900, 50 to 1000, 50 to 2000, 50 to 4000, 510 to 6000, 50 to 8000, 50 to 10000, 100 to 200, 100 to 300, 100 to 400, 100 to 500, 100 to 600, 100 to 700, 100 to 800, 100 to 900, 100 to 1000, 100 to 2000, 100 to 4000, 100 to 6000, 100 to 8000, 100 to 10000, 200 to 300, 200 to 400, 200 to 500, 200 to 600, 200 to 700, 200 to 800, 200 to 900, 200 to 1000, 200 to 2000, 200 to 4000, 200 to 6000, 200 to 8000, 200 to 10000, 300 to 400, 300 to 500, 300 to 600, 300 to 700, 300 to 800, 300 to 900, 300 to 1000, 300 to 2000, 300 to 4000, 300 to 6000, 300 to 8000, 300 to 10000, 400 to 500, 400 to 600, 400 to 700, 400 to 800, 400 to 900, 400 to 1000, 400 to 2000, 400 to 4000, 400 to 6000, 400 to 8000, 400 to 10000, 500 to 600, 500 to 700, 500 to 800, 500 to 900, 500 to 1000, 500 to 2000, 500 to 4000, 500 to 6000, 500 to 8000, 500 to 10000, 600 to 700, 600 to 800, 600 to 900, 600 to 1000, 600 to 2000, 600 to 4000, 600 to 6000, 600 to 8000, 600 to 10000, 700 to 800, 700 to 900, 700 to 1000, 700 to 2000, 700 to 4000, 700 to 6000, 700 to 8000, 700 to 10000, 800 to 900, 800 to 1000, 800 to 2000, 800 to 4000, 800 to 6000, 800 to 8000, 800 to 10000, 900 to 1000, 900 to 2000, 900 to 4000, 900 to 6000, 900 to 8000, 900 to 10000, 1000 to 2000, 1000 to 4000, 1000 to 6000, 1000 to 8000, 1000 to 10000, 2000 to 4000, 2000 to 6000, 2000 to 8000, 2000 to 10000, 4000 to 6000, 4000 to 8000, 4000 to 10000, 6000 to 8000, 6000 to 10000, and 8000 to 10000 tissue portions per cm$^2$ area) of the skin region to which the apparatus is applied (e.g., the treatment area).

Base Unit and User Interface

An apparatus of the invention may be in communication with a base unit, which may include, e.g., a user interface, a power supply, control electronics, mechanisms to drive operation of the apparatus, and other components. The base unit may feature a computer, which may be programmed to operate and/or control any or all aspects of an apparatus of the invention.

A user interface in the base unit may include buttons, keys, switches, toggles, spin-wheels, screens, touch screens, keyboards, cursors, dials, indicators, displays, and/or other components. The user interface may be configured to indicate proper couplings and attachments of the support base (e.g., support base 11), the z-actuator (e.g., a voice coil; z-actuator 12), the tissue removal tool (e.g., a piston) (e.g., tissue removal tool 13), the hollow needle(s) (e.g., hollow needle 14), the aspiration tube (e.g., aspiration tube 15), the trap (e.g., trap 16), the pressure generating source (e.g., a vacuum pump (e.g., pressure generating source 17), and/or scaffold 18 to form the needle assembly (e.g., needle assembly 10), charged and/or powered status of the apparatus, the mode and/or position of hollow needle(s), the application of low or high pressure, actuation of apparatus components, and/or other useful indicia. The user interface may be configured to provide information about the number and kind of hollow needle(s) of the apparatus, the treatment area, the treatment coverage (e.g., areal fraction of skin surface area removed), the arrangement of the hollow needle(s), the potential depth of penetration by the hollow needle(s), the mechanism or mode of operation, use count of the hollow needle(s), and other useful information. The user interface may allow adjustment of parameters and/or operation mode, application of high or low pressure, and/or activation of penetration into the skin by the hollow needle(s). The user interface may also be configured to transmit and/or receive information from another unit. For example, user actions at a user interface on the apparatus may be reflected by a user interface of the base unit, or vice versa.

The base unit may include buttons, keys, switches, toggles, spin-wheels, and/or other activation mechanisms to allow adjustment of parameters and/or operation mode, application of high or low pressure, penetration into the skin by the hollow needle(s), and/or powering on or off of the base unit and/or pressure generating source. These components may be integrated into the user interface of the base unit.

The base unit may further include electronics to control operation of the apparatus, pressure generating source, and/or other components couple to the apparatus. For example, the base unit may include one or more microcontrollers, programmable logic, discrete elements, and/or other components. The base unit may further have one or more power supplies. Power supplies may include batteries, alternators, generators, and/or other components. The base unit may be configured to allow conversion of main power to DC for system operation, for example. In some embodiments, the base unit has a battery charging station for use with a battery-powered apparatus.

The base unit may include a user interface that indicates, e.g., that the hollow needle is properly installed in the needle assembly, that the needle assembly is properly coupled to the actuation unit, that the apparatus is charged or otherwise powered (e.g., the amount of battery life remaining), that the hollow needle is in an extended or retracted position, that a pressure generating source is coupled to the apparatus, the fill level of a trap for collecting cored tissue portions, and/or other useful information. User interface may include information about the apparatus, such as the number of hollow needle(s) of the apparatus, the arrangement of the hollow needle(s), the potential depth of tissue penetration by the hollow needle(s), the mechanism or mode of operation, and/or other useful information. User interface may include buttons, keys, switches, toggles, spin-wheels, LED displays, and/or touch screens that allow the user to observe and change various parameters or configurations during operation of the apparatus, to activate the pressure generating source, and/or to initiate penetration into the skin by the hollow needle(s). User interface may also be configured to transmit and/or receive information from another unit, such as a computer.

Additional Components

Additional components, such as a camera and/or viewing station, may be coupled to an apparatus of the invention. A camera may be used to image a treatment area before, during, or after treatment. In some embodiments, a camera may be disposed in or on the apparatus. The camera may transmit signal to a viewing station, such as a computer, that may be disposed in the line of sight of the device operator. The image or images transmitted by the camera to the viewing station (e.g., a computer) may be processed by a visualization software. The visualization software may be capable of calculating a hole density within a treatment area (e.g., the number of holes generated per unit area). The image or images transmitted by the camera to the viewing station (e.g., a computer) may assist the operator in treating the skin. A fluid system may be coupled to an apparatus of the invention to facilitate cleaning of the skin, e.g., with saline or a sterilizing solution.

The hollow needles, needle assemblies, actuation units, apparatuses, kits, and methods of the invention may be used in combination with a medical record system, e.g., a Computerized Patient Record System (CPRS), and/or a graphic user interface (GUI). The graphic user interface may provide information regarding various parameters of the treatment site of the patient, such as the size of the array pattern and the number of holes to be selected for in each treatment site.

Materials

The hollow needles, needle assemblies, actuation units, apparatuses, kits, and methods of the invention can include any useful materials. For example, the needle assembly may include and/or be formed from any useful polymer or plastic. Such materials may include alginate, benzyl hyaluronate, carboxymethylcellulose, cellulose acetate, chitosan, collagen, dextran, epoxy, gelatin, hyaluronic acid, hydrocolloids, nylon (e.g., nylon 6 or PA6), pectin, poly (3-hydroxyl butyrate-co-poly (3-hydroxyl valerate), polyalkanes, polyalkene, polyalkynes, polyacrylate (PA), polyacrylonitrile (PAN), polybenzimidazole (PBI), polycarbonate (PC), polycaprolactone (PCL), polyester (PE), polyethylene glycol (PEG), polyethylene oxide (PEO), PEO/polycarbonate/polyurethane (PEO/PC/PU), poly(ethylene-co-vinyl acetate) (PEVA), PEVA/polylactic acid (PEVA/PLA), polyethylene, polypropylene, poly (ethylene terephthalate) (PET), PET/poly (ethylene naphthalate) (PET/PEN) polyglactin, polyglycolic acid (PGA), polyglycolic acid/polylactic acid (PGA/PLA), polyimide (PI), polylactic acid (PLA), poly-L-lactide (PLLA), PLLA/PC/polyvinylcarbazole (PLLA/PC/PVCB), poly (β-malic acid)-copolymers (PMLA), polymethacrylate (PMA), poly (methyl methacrylate) (PMMA), polystyrene (PS), polyurethane (PU), poly (vinyl alcohol) (PVA), polyvinylcarbazole (PVCB), polyvinyl chloride (PVC), polyvinylidenedifluoride (PVDF), polyvinylpyrrolidone (PVP), silicone, rayon, polytetrafluoroethylene (PTFE), polyether ether ketone (PEEK), or combinations thereof. Polymers and/or plastics of the invention may be composite materials in which additives to the polymers and/or plastics, such as ceramics or particles, alter the mechanical properties.

Elements of the invention (e.g., all or a portion of the apparatus, such as all or a portion of the needle assembly, the actuation unit, or other components) may also include and/or be formed from any useful metal or metal alloy. For example, in some embodiments, a hollow needle may be a metallic needle. Metals and alloys featured in the invention include stainless steel; titanium; a nickel-titanium (NiTi) alloy; a nickel-titanium-niobium (NiTiNb) alloy; a nickel-iron-gallium (NiFeGa) alloy; a nickel-manganese-gallium (NiMnGa) alloy; a copper-aluminum-nickel (CuAlNi) alloy; a copper-zinc (CuZn) alloy; a copper-tin (CuSn) alloy; a copper-zinc-aluminum (CuZnAl) alloy; a copper-zinc-silicon (CuZnSi) alloy; a copper-zinc-tin (CuZnSn) alloy; a copper-manganese alloy; a gold-cadmium (AuCd) alloy; a silver-cadmium (AgCd) alloy; an iron-platinum (FePt) alloy; an iron-manganese-silicon (FeMnSi) alloy; a cobalt-nickel-aluminum (CoNiAl) alloy; a cobalt-nickel-gallium (CoNiGa) alloy; or a titanium-palladium (TiPd) alloy. Elements of the invention may also include and/or be formed from glass. For example, an apparatus of the invention may include one or more glass hollow needles.

The hollow needles, needle assemblies, actuation units, apparatuses, kits, and methods of the invention may contain one or more adhesives. An adhesive may be located on a surface, between elements, or otherwise adhered to an element of the invention. Useful adhesives include a biocompatible matrix (e.g., those including at least one of collagen (e.g., a collagen sponge), low melting agarose (LMA), polylactic acid (PLA), and/or hyaluronic acid (e.g., hyaluronan); a photosensitizer (e.g., Rose Bengal, riboflavin-5-phosphate (R-5-P), methylene blue (MB), N-hydroxypyridine-2-(1H)-thione (N-HTP), a porphyrin, or a chlorin, as well as precursors thereof); a photochemical agent (e.g., 1,8 naphthalimide); a synthetic glue (e.g., a cyanoacrylate adhesive, a polyethylene glycol adhesive, or a gelatin-resorcinol-formaldehyde adhesive); a biologic sealant (e.g., a mixture of riboflavin-5-phosphate and fibrinogen, a fibrin-based sealant, an albumin-based sealant, or a starch-based sealant); or a hook or loop and eye system (e.g., as used for Velcro®). In some embodiments, the adhesive is biodegradable.

The adhesive may be a pressure-sensitive adhesive (PSA). The properties of pressure sensitive adhesives are governed by three parameters: tack (initial adhesion), peel strength (adhesion), and shear strength (cohesion). Pressure-sensitive adhesives can be synthesized in several ways, including solvent-borne, water-borne, and hot-melt methods. Tack is the initial adhesion under slight pressure and short dwell time and depends on the adhesive's ability to wet the contact surface. Peel strength is the force required to remove the PSA from the contact surface. The peel adhesion depends on many factors, including the tack, bonding history (e.g. force, dwell time), and adhesive composition. Shear strength is a measure of the adhesive's resistance to continuous stress. The shear strength is influenced by several parameters, including internal adhesion, cross-linking, and viscoelastic properties of the adhesive. Permanent adhesives are generally resistant to debonding and possess very high peel and shear strength. Pressure-sensitive adhesives may include natural rubber, synthetic rubber (e.g., styrene-butadiene and styrene-ethylene copolymers), polyvinyl ether, polyurethane, acrylic, silicones, and ethylene-vinyl acetate copolymers. A copolymer's adhesive properties can be altered by varying the composition (via monomer components) changing the glass transition temperature (Tg) or degree of cross-linking. In general, a copolymer with a lower Tg is less rigid and a copolymer with a higher Tg is more rigid. The tack of PSAs can be altered by the addition of components to alter the viscosity or mechanical properties. Pressure sensitive adhesives are further described in Czech et al., "Pressure-Sensitive Adhesives for Medical Applications," in Wide Spectra of Quality Control, Dr. Isin Akyar (Ed., published by InTech), Chapter 17 (2011), which is hereby incorporated by reference in its entirety.

An apparatus, method, or kit may contain or be configured to deliver one or more useful therapeutic agents. For example, the hollow needles of the apparatus of the invention may be configured to administer one or more therapeutic agents to the skin. The hollow needles of the apparatus of the invention may be capable of creating direct channels or holes to the local blood supply and local perfusion by removing cored tissue portions. The direct channels or holes may be used to deliver useful therapeutic agents. Depending on the size (e.g., diameter and/or active length) of the hollow needles, holes having different diameters and/or penetration depths may be created. For example, hollow needles having a large diameter (e.g., 18 gauge) and/or a long active length may be used to create large and deep holes that may be used as delivery channels to deliver a large volume dose of therapeutic agents. In some embodiments, the holes may be plugged. In some embodiments, the holes may be covered with a dressing (e.g., a compressive or occlusive dressing) and/or a closure (e.g., bandage, hemostats, sutures, or adhesives) to prevent the delivered therapeutic agents from leaking out of the skin and/or to maintain moisture of the treated skin area. Delivery of useful therapeutic agents through the holes created by the hollow needles of the apparatus may provide precise control of dosing of the therapeutic agents.

Examples of useful therapeutic agents include one or more growth factors (e.g., vascular endothelial growth factor (VEGF), platelet-derived growth factor (PDGF), transforming growth factor beta (TGF-β), fibroblast growth factor (FGF), epidermal growth factor (EGF), and keratinocyte growth factor); one or more stem cells (e.g., adipose tissue-derived stem cells and/or bone marrow-derived mesenchymal stem cells); one or more skin whitening agents (e.g., hydroquinone); one or more vitamin A derivatives (e.g., tretinoin), one or more analgesics (e.g., paracetamol/acetaminophen, aspirin, a non-steroidal antiinflammatory drug, as described herein, a cyclooxygenase-2-specific inhibitor, as described herein, dextropropoxyphene, co-codamol, an opioid (e.g., morphine, codeine, oxycodone, hydrocodone, dihydromorphine, pethidine, buprenorphine, tramadol, or methadone), fentanyl, procaine, lidocaine, tetracaine, dibucaine, benzocaine, p-butylaminobenzoic acid 2-(diethylamino) ethyl ester HCl, mepivacaine, piperocaine, dyclonine, or venlafaxine); one or more antibiotics (e.g., cephalosporin, bactitracin, polymyxin B sulfate, neomycin, bismuth tribromophenate, or polysporin); one or more antifungals (e.g., nystatin); one or more antiinflammatory agents (e.g., a non-steroidal antiinflammatory drug (NSAID, e.g., ibuprofen, ketoprofen, flurbiprofen, piroxicam, indomethacin, diclofenac, sulindac, naproxen, aspirin, ketorolac, or tacrolimus), a cyclooxygenase-2-specific inhibitor (COX-2 inhibitor, e.g., rofecoxib (Vioxx®), etoricoxib, and celecoxib (Celebrex®)), a glucocorticoid agent, a specific cytokine directed at T lymphocyte function), a steroid (e.g., a corticosteroid, such as a glucocorticoid (e.g., aldosterone, beclometasone, betamethasone, cortisone, deoxycorticosterone acetate, dexamethasone, fludrocortisone acetate, hydrocortisone, methylprednisolone, prednisone, prednisolone, or triamcinolone) or a mineralocorticoid agent (e.g., aldosterone, corticosterone, or deoxycorticosterone)), or an immune selective antiinflammatory derivative (e.g., phenylalanine-glutamine-glycine (FEG) and its D-isomeric form (feG))); one or more antimicrobials (e.g., chlorhexidine gluconate, iodine (e.g., tincture of iodine, povidone-iodine, or Lugol's iodine), or silver, such as silver nitrate (e.g., as a 0.5% solution), silver sulfadiazine (e.g., as a cream), or Ag$^+$ in one or more useful carriers (e.g., an alginate, such as Acticoat® including nanocrystalline silver coating in high density polyethylene, available from Smith & Nephew, London, U.K., or Silvercel® including a mixture of alginate, carboxymethylcellulose, and silver coated nylon fibers, available from Systagenix, Gatwick, U.K.; a foam (e.g., Contreet® Foam including a soft hydrophilic polyurethane foam and silver, available from Coloplast A/S, Humlebæk, Denmark); a hydrocolloid (e.g., Aquacel® Ag including ionic silver and a hydrocolloid, available from Conva Tec Inc., Skillman, N.J.); or a hydrogel (e.g., Silvasorb® including ionic silver, available from Medline Industries Inc., Mansfield, Mass.)); one or more antiseptics (e.g., an alcohol, such as ethanol (e.g., 60-90%), 1-propanol (e.g., 60-70%), as well as mixtures of 2-propanol/isopropanol; boric acid; calcium hypochlorite; hydrogen peroxide; manuka honey and/or methylglyoxal; a phenol (carbolic acid) compound, e.g., sodium 3,5-dibromo-4-hydroxybenzene sulfonate, trichlorophenylmethyl iodosalicyl, or triclosan; a polyhexanide compound, e.g., polyhexamethylene biguanide (PHMB); a quaternary ammonium compound, such as benzalkonium chloride (BAC), benzethonium chloride (BZT), cetyl trimethylammonium bromide (CTMB), cetylpyridinium chloride (CPC), chlorhexidine (e.g., chlorhexidine gluconate), or octenidine (e.g., octenidine dihydrochloride); sodium bicarbonate; sodium chloride; sodium hypochlorite (e.g., optionally in combination with boric acid in Dakin's solution); or a triarylmethane dye (e.g., Brilliant Green)); one or more antiproliferative agents (e.g., sirolimus, tacrolimus, zotarolimus, biolimus, or paclitaxel); one or more emollients; one or more hemostatic agents (e.g., collagen, such as microfibrillar collagen, chitosan, calcium-loaded zeolite, cellulose, anhydrous aluminum sulfate, silver nitrate, potassium alum, titanium oxide, fibrinogen, epinephrine, calcium alginate, poly-N-acetyl glucosamine, thrombin, coagulation factor(s) (e.g., II, V, VII, VIII, IX, X, XI, XIII, or Von Willebrand factor, as well as activated forms thereof), a procoagulant (e.g., propyl gallate), an anti-fibrinolytic agent (e.g., epsilon aminocaproic acid or tranexamic acid), and the like); one or more procoagulative agents (e.g., any hemostatic agent described herein, desmopressin, coagulation factor(s) (e.g., II, V, VII, VIII, IX, X, XI, XIII, or Von Willebrand factor, as well as activated forms thereof), procoagulants (e.g., propyl gallate), antifibrinolytics (e.g., epsilon aminocaproic acid), and the like); one or more anticoagulative agents (e.g., heparin or derivatives thereof, such as low molecular weight heparin, fondaparinux, or idraparinux; an anti-platelet agent, such as aspirin, dipyridamole, ticlopidine, clopidogrel, or prasugrel; a factor Xa inhibitor, such as a direct factor Xa inhibitor, e.g., apixaban or rivaroxaban; a thrombin inhibitor, such as a direct thrombin inhibitor, e.g., argatroban, bivalirudin, dabigatran, hirudin, lepirudin, or ximelagatran; or a coumarin derivative or vitamin K antagonist, such as warfarin (coumadin), acenocoumarol, atromentin, phenindione, or phenprocoumon); one or more immune modulators, including corticosteroids and non-steroidal immune modulators (e.g., NSAIDS, such as any described herein); one or more proteins; and/or one or more vitamins (e.g., vitamin A, C, and/or E). One or more of botulinum toxin, fat (e.g. autologous), hyaluronic acid, a collagen-based filler, or other filler may also be administered to the skin. Platelet rich plasma may also be administered to the skin. One or more therapeutic agents described herein may be formulated as a depot preparation. In general, depot preparations are typically longer acting than non-depot preparations. In some embodiments, depot preparations are prepared using suitable polymeric or hydrophobic materials (for example an emulsion in an acceptable oil) or ion exchange resins, or as sparingly soluble derivatives, for example, as a sparingly soluble salt.

A therapeutic agent may include anticoagulative and/or procoagulative agents. For instance, by controlling the extent of bleeding and/or clotting in treated skin regions, a skin tightening effect may be more effectively controlled. Thus, in some embodiments, the methods and devices herein include or can be used to administer one or more anticoagulative agents, one or more procoagulative agents, one or more hemostatic agents, one or more fillers, or combinations thereof. In particular embodiments, the therapeutic agent controls the extent of bleeding and/or clotting in the treated skin region, including the use one or more anticoagulative agents (e.g., to inhibit clot formation prior to skin healing or slit/hole closure) and/or one or more hemostatic or procoagulative agents.

Configurations

An apparatus of the invention may include a variety of components in different configurations. For example, an apparatus may include one or more hollow needles, a pressure generating source, a tissue removal tool (e.g., a piston), an aspiration tube, a trap for collecting waste materials (e.g., cored tissue portions), a support base, and an actuation unit (e.g., an actuation unit including an x-, y-, and/or z-actuator). One or more hollow needles, a pressure generating source, a tissue removal tool (e.g., a piston), an aspiration tube, a trap for collecting waste materials (e.g., cored tissue portions), a support base, and/or a z-actuator may be detachably connected to form a needle assembly (e.g., needle assembly 10 shown in FIGS. 1A-1F). Accordingly, an apparatus may include a needle assembly and an actuation unit. The trap may be disposed in the aspiration tube, in the hollow needle, or in a separate module disposed between the hollow needle and the z-actuator or external to the apparatus. Similarly, a pressure generating source (e.g., a vacuum pump) may be disposed external to other components or may be integrated into, e.g., the aspiration tube. Mechanisms for actuation, translation, and/or position detection; control electronics; and/or user interface may be included in the apparatus or external to the apparatus. These configurations facilitate the sterilization of the apparatus as needed for patient treatment.

FIGS. 1A-1F are schematic illustrations showing a possible configuration of needle assembly 10 including support base 11, z-actuator (e.g., a voice coil) 12, tissue removal tool (e.g., a piston) 13, hollow needle 14, aspiration tube 15, trap 16, pressure generating source (e.g., a vacuum pump) 17, and scaffold 18. In this configuration, trap 16 is installed between pressure generating source (e.g., a vacuum pump) 17 and aspiration tube 15. Trap 16, such as a stainless steel sterilizing grade filter membrane (Mott Corporation), can be used to prevent cored tissue portions from entering pressure generating source (e.g., a vacuum pump) 17. Trap 16 may be detached and removed for cleaning and/or to be replaced. Hollow needle 14 is in communication with support base 11, z-actuator (e.g., a voice coil) 12, and tissue removal tool (e.g., a piston) 13. Z-actuator (e.g., a voice coil) 12 causes translation of hollow needle 14 along its longitudinal axis and insertion into and withdrawal of hollow needle 14 from the skin. The needle assembly of the apparatus may also be digitally controlled (e.g., at a user interface). As such, operation of the apparatus may be entirely or almost entirely controllable by features of the apparatus.

Treatment of a region of skin of a patient may proceed by supplying power to the apparatus, preparing the skin region for treatment (e.g., sterilizing and/or positioning the skin), placing a hollow needle (e.g., hollow needle 14) of the apparatus upon the skin in the treatment region, and activating the mechanism (e.g., z-actuator) that drives penetration of hollow needle into the skin. As the hollow needle is withdrawn from the skin, it is in communication and contact with the tissue removal tool (e.g., a piston; tissue removal tool 13), which slides into the lumen and pushes the cored tissue portion in the lumen of the hollow needle (e.g., hollow needle 14) towards the needle tip (e.g., needle tip 18) as the hollow needle continues to move upward. The operator may activate the pressure generating source (e.g., a vacuum pump; pressure generating source 17) to remove cored tissue portion from the needle tip. The activation of the pressure generating source may be automatically trigged by the hollow needle (e.g., hollow needle 14) when the hollow needle is in its uppermost position. The cored tissue portion is aspirated into the aspiration tube (e.g., aspiration tube 15) as vacuum is applied and collects at the trap (e.g., trap 16) between the aspiration tube and the pressure generating source (e.g., a vacuum pump). Application of vacuum may be ceased prior to translation of the hollow needle to an adjacent skin region for further treatment. The process may be repeated until the entire skin region of interest has been treated, at which point the hollow needle (e.g., hollow needle 14) and/or the entire needle assembly (e.g., needle assembly 10) can be detached from the apparatus via a quick-release mechanism, the hollow needle (e.g., hollow needle 14) and/or the entire needle assembly (e.g., needle assembly 10) disposed of or replaced, and the other components of the apparatus sterilized as needed. Such treatment may provide a plurality of cored tissue portions with dimensions, geometries, and other characteristics corresponding to the dimensions, geometries, and other characteristics of the hollow needle. For example, a hollow needle inserted about 2 mm into the skin may provide a tissue portion having a depth or length of about 2 mm.

In an alternative configuration, an apparatus of the invention may integrate a miniature pressure generating source (e.g., a vacuum pump) into the needle assembly of the apparatus. In this instance, the miniature pressure generating source (e.g., a vacuum pump) is in direct communication with the hollow needle (e.g., the proximal end of the hollow needle). A cored tissue portion inside the lumen of the hollow needle may be aspirated upward through the hollow needle by applying vacuum. A trap may be installed between the hollow needle and the miniature pressure generating source (e.g., a vacuum pump) to collect the cored tissue portion and prevent the cored tissue portion from entering the miniature pressure generating source (e.g., a vacuum pump). In this instance, the cored tissue portion in the lumen is directly aspirated upward through the hollow needle.

The pressure generating source (e.g., a vacuum pump) may be part of the needle assembly of the apparatus (e.g., attached to the aspiration tube (if present)) or external to the apparatus; for example, the vacuum source may be a medical or house vacuum source. Alternatively, the vacuum source may be a pump, such as a scroll, momentum transfer, rotary, diffusion, or diaphragm pump. The apparatus may further include a power supply, control electronics, and/or actuation, translation, and/or position detection mechanisms.

The apparatus may be charged by either removing the batteries from their holder, e.g., to be charged in a battery charging unit, or by placing the apparatus in an external battery charging station. The apparatus and/or base unit may also include components that allow for wireless communication therebetween.

Kits

The invention also features kits for cosmetic resurfacing of the skin tissue. In some embodiments, kits may include one or more hollow needles. The kits may also include, either alone or with the one or more hollow needles, other components of a needle assembly of the apparatus (e.g., a support base (e.g., support base 11), a z-actuator (e.g., a voice coil; z-actuator 12), a tissue removal tool (e.g., tissue removal tool (e.g., a piston) 13), an aspiration tube (e.g., aspiration tube 15), a trap (e.g., trap 16), a pressure generating source (e.g., pressure generating source (e.g., a vacuum pump) 17), and/or a scaffold (e.g., scaffold 18)), an actuation unit including an x- and y-actuators (e.g., actuation unit 151), and/or a cover (e.g., cover 161). The one or more hollow needles, the entire needle assembly, and/or components of the needle assembly in a kit may be configured to be detachably attached to the apparatus. The hollow needle(s) may be configured to be in communication with a pressure generating source (e.g., a vacuum pump). In some embodiments, kits may be packaged with the hollow needle(s) in sterile form and with instructions for applying the hollow needle(s) to the needle assembly of an apparatus of the invention and/or with instructions for applying the needle assembly to the actuation unit of the apparatus of the invention. In some embodiments, kits may be packaged with the entire needle assembly in sterile form and with instructions for applying the needle assembly to the actuation unit of an apparatus of the invention. Kits may also include one or more replacement hollow needles and/or one or more replacement components of the needle assembly. Kits may also include entire needle assemblies as replacement parts.

Kits of the invention may include additional components, such as a trap for collecting waste materials (e.g., cored tissue portions); a pressure generating source (e.g., a vacuum pump); mechanisms for actuation, translation, and position detection (e.g., one or more voice coil (VC), pneumatic, electromagnetic, and/or piezoelectric actuators; driving wheels; and/or a camera); and a base unit having a user interface. In addition, kits of the invention may include any other useful components, such as instructions on how to use the hollow needle(s), the needle assembly, the actuation unit, and/or the apparatus, one or more therapeutic agents (e.g., any described herein, such as an anticoagulative and/or procoagulative agent, and optionally in combination with a useful dispenser for applying the therapeutic agent, such as a brush, spray, film, ointment, cream, lotion, or gel), one or more wound cleansers (e.g., including any antibiotic, antimicrobial, or antiseptic, such as those described herein, in any useful form, such as a brush, spray, film, ointment, cream, lotion, or gel), one or more dressings (e.g., compressive or occlusive dressings), one or more closures (e.g., bandage, hemostats, sutures, or adhesives), one or more debriding agents, one or more adhesives (e.g., any described herein), one or more cosmetics (e.g., as described herein), and/or other suitable or useful materials.

Kits of the invention may include any of the components provided herein (e.g., hollow needle(s), a trap, a pressure generating source, a tissue removal tool (e.g., a piston), an aspiration tube, and/or a z-actuator) in any number. Kits may also have or be designed to have any of the configurations described herein.

Method for Cosmetic Skin Resurfacing

Any of the hollow needles, needle assemblies, actuation units, apparatuses, kits, and methods of the invention may be used for cosmetic skin resurfacing of the skin tissue by removing skin tissue portions. The hollow needles, needle assemblies, actuation units, apparatuses, kits, and methods of the invention can be applied to treat one or more skin regions. In particular embodiments, these regions are treated with one or more procedures to improve skin appearance and to rejuvenate skin. In preferred embodiments, the hollow needles, needle assemblies, actuation units, apparatuses, kits, and methods described herein can be useful for skin tightening, e.g., reducing skin laxity (e.g., loose or sagging skin or other skin irregularities). In other embodiments, the hollow needles, needle assemblies, actuation units, apparatuses, kits, and methods herein can be useful for removal of, e.g., pigment, hair follicles, and/or vessels in the skin, and/or for treating acne, allodynia, blemishes, ectopic dermatitis, hyperpigmentation, hyperplasia (e.g., lentigo or keratosis), loss of translucency, loss of elasticity, melasma (e.g., epidermal, dermal, or mixed subtypes), photodamage, rashes (e.g., erythematous, macular, papular, and/or bullous conditions), psoriasis, rhytides (or wrinkles, e.g., lateral canthal lines ("crow's feet"), age-related rhytides, sun-related rhytides, or heredity-related rhytides), sallow color, scar contracture (e.g., relaxation of scar tissue), scarring (e.g., due to acne, surgery, or other trauma), skin aging, skin contraction (e.g., excessive tension in the skin), skin irritation/sensitivity, striae (or stretch marks), tattoo removal, vascular lesions (e.g., angioma, erythema, hemangioma, papule, port wine stain, rosacea, reticular vein, or telangiectasia), or any other unwanted skin irregularities. The hollow needles, needle assemblies, actuation units, apparatuses, kits, and methods described herein may also be used to penetrate skin and trigger biological responses that may contribute to new skin tissue formation and tissue resurfacing and remodeling.

Such skin treatments may be applied to any part or parts of the body, including the face (e.g., eyelid, cheeks, chin, forehead, lips, or nose), neck, chest (e.g., as in a breast lift), arms, hands, legs, abdomen, and/or back. Accordingly, the hollow needles, needle assemblies, actuation units, apparatuses, kits, and methods of the invention can be configured to be useful for treatment of regions of the body with different sizes and geometries. For example, arrays of hollow needles of different sizes, geometries, and arrangements may be included in a kit of the invention to allow for treatment of both facial (e.g., with tips having small arrays of regular or irregular geometries) and abdominal regions (e.g., with tips having large arrays of regular geometries). In some embodiments, such arrangements and configurations can be in one or more rows or in a semi-random spatial distribution. In other embodiments, arrangements of hollow needles can include any useful shape (e.g., linear, curved, or stellate), size, geometry, depth, and/or other characteristics. Alternatively, an apparatus of the invention can include a single hollow needle and the apparatus can be used to repeatedly remove skin tissue in an array pattern forming one or more rows, random or semi-random patterns, or other patterns.

Treatment methods may involve forming a plurality of holes in the skin by contacting one or more hollow needles to the skin of a subject and removing the cored tissue portions from the skin. Penetration into the skin by the hollow needle(s) create holes and so effectively reduce tissue volume and/or improve tissue quality upon healing. For example, forming a series of cored tissue portions (e.g., removal of about 20% of the total skin area) and corresponding holes in a high laxity skin region and optionally subsequent compression of the skin region to close the holes may promote the growth of new skin (e.g., improved tissue). Healing of the tissue under a dressing (e.g., a compressive or occlusive dressing) allows for the existing tissue to span the gap introduced by the removal of cored tissue portions, thereby reducing the skin volume and area (e.g., by tightening the skin). A dressing (e.g., a compressive or occlusive dressing) may also help to maintain moisture of the treated skin area and/or to prevent delivered therapeutic agents from leaking out of the skin.

Any beneficial area or volumetric fraction of the skin region can be removed. For example, between about 1% to about 65% (e.g., an areal fraction between about 0.01 to about 0.65, such as 0.01 to 0.65, 0.01 to 0.6, 0.01 to 0.55, 0.01 to 0.5, 0.01 to 0.45, 0.01 to 0.4, 0.01 to 0.35, 0.01 to 0.3, 0.01 to 0.25, 0.01 to 0.2, 0.01 to 0.15, 0.01 to 0.1, 0.01 to 0.05, 0.03 to 0.65, 0.05 to 0.65, 0.07 to 0.65, 0.09 to 0.65, 0.1 to 0.65, 0.15 to 0.65, 0.2 to 0.65, 0.25 to 0.65, 0.3 to 0.65, 0.35 to 0.65, 0.4 to 0.65, 0.45 to 0.65, 0.5 to 0.65, 0.55 to 0.65, and 0.6 to 0.65) of tissue in the treatment area may be removed. In some embodiments, between about 1% to about 5% (e.g., an areal fraction between about 0.01 to about 0.05, such as 0.01 to 0.05, 0.01 to 0.045, 0.01 to 0.04, 0.01 to 0.035, 0.01 to 0.03, 0.01 to 0.025, 0.01 to 0.02, 0.01 to 0.015, 0.015 to 0.05, 0.02 to 0.05, 0.025 to 0.05, 0.03 to 0.05, 0.035 to 0.05, 0.04 to 0.05, and 0.045 to 0.05) of tissue in the treatment area may be removed. In some embodiments, between about 2% to about 3% (e.g., an areal fraction between about 0.02 to about 0.03, such as 0.02 to 0.03, 0.02 to 0.028, 0.02 to 0.026, 0.02 to 0.024, 0.02 to 0.022, 0.022 to 0.03, 0.024 to 0.03, 0.026 to 0.03, 0.028 to 0.03; e.g., 0.025) of tissue in the treatment area may be removed.

Tissue can be removed from the treatment region with various hole density (e.g., the number of holes per unit area) corresponding to the number and geometry of hollow needle(s) of the apparatus used and the number of applications of the hollow needle(s) to the treatment region. Different hole densities may be desirable for different regions of skin and for different conditions and may be achieved using different hollow needle(s). For example, 15 holes corresponding to the size of a 19 gauge needle and their corresponding cored tissue portions may be created in a given treatment area by actuation of a single 19 gauge needle 15 times, or by actuating an array having five 19 gauge needles three times. Spacing the same number of holes further apart will result in a lower hole density per unit area. For example, 15 holes may be created within a 0.5 mm by 0.3 mm region or within a 5 mm by 3 mm region. In particular embodiments, hollow needles, needle assemblies, actuation units, apparatuses, kits, and methods of the invention (e.g., any described herein) are configured to provide from about 10 to about 10000 cored tissue portions per $cm^2$ area of the skin region (e.g., as described herein). The array of holes created by removal of the skin tissue portions may be created in any beneficial pattern within the skin region. For example, a higher density and/or smaller spacing of tissue portions and corresponding holes can be ablated in the skin in the center of a pattern or in thicker portions of the skin. A pattern may be semi-random or include one or more of staggered rows and/or blocks, parallel rows and/or blocks, a circular pattern, a spiral pattern, a square or rectangular pattern, a triangular pattern, a hexagonal pattern, a radial distribution, or a combination of one or more such patterns. The pattern may arise from the use of one or more hollow needles with one or more configurations and numbers of hollow needles applied in any ordered or disordered manner. Modifications to the average length, diameter, shapes, and/or other characteristics of one or more hollow needles used to treat a skin region may also result in a specific pattern of holes in the skin. Such patterns may be optimized to promote unidirectional, non-directional, or multidirectional contraction or expansion of skin (e.g., in the x-direction, y-direction, x-direction, x-y plane, y-z plane, x-z plane, and/or xyz-plane), such as by modifying the average length, depth, diameter, density, orientation, and/or spacing between hollow needles.

Any portion of the skin can be removed. Tissue portions created by penetration into the skin with the hollow needle(s) may include epidermal tissue, dermal tissue, subcutaneous fat, and/or cells or tissue proximal to the dermal/fatty layer boundary (e.g., stem cells). In some embodiments, a tissue portion may have a length that corresponds to the depth of penetration of the skin layer. In some embodiments, the depth of penetration may be (i) into the dermal layer, (ii) through the entire dermal layer to the junction of the dermal layer and the subcutaneous fat layer, or (iii) into the subcutaneous fat layer. The total depth of the epidermal, dermal, and subcutaneous fat layers may vary based on the region and age of the body being treated. In some instances, the depth of the epidermal layer is between about 0.01 mm to 0.2 mm, and/or the depth of the dermal layer is between about 0.3 mm to 6.0 mm. In some embodiments, the total depth of the epidermal and dermal layers may be between about 0.3 mm and 6.2 mm, corresponding to a possible tissue portion having a length between about 0.3 mm and 6.2 mm (e.g., between about 0.3 mm and 0.6 mm, 0.3 mm and 0.9 mm, 0.3 mm and 1.5 mm, 0.3 mm and 2.0 mm, 0.3 mm and 2.5 mm, 0.3 mm and 3.0 mm, 0.3 mm and 3.5 mm, 0.3 mm and 4.0 mm, 0.3 mm and 4.5 mm, 0.3 mm and 5.0 mm, 0.3 mm and 5.5 mm, 0.3 mm and 6.0 mm, 0.3 mm and 6.2 mm, 0.6 mm and 0.9 mm, 0.6 mm and 1.5 mm, 0.6 mm and 2.0 mm, 0.6 mm and 2.5 mm, 0.6 mm and 3.0 mm, 0.6 mm and 3.5 mm, 0.6 mm and 4.0 mm, 0.6 mm and 4.5 mm, 0.6 mm and 5.0 mm, 0.6 mm and 5.5 mm, 0.6 mm and 6.0 mm, 0.6 mm and 6.2 mm, 0.9 mm and 1.5 mm, 0.9 mm and 2.0 mm, 0.9 mm and 2.5 mm, 0.9 mm and 3.0 mm, 0.9 mm and 3.5 mm, 0.9 mm and 4.0 mm, 0.9 mm and 4.5 mm, 0.9 mm and 5.0 mm, 0.9 mm and 5.5 mm, 0.9 mm and 6.0 mm, 0.9 mm and 6.2 mm, 1.5 mm and 2.0 mm, 1.5 mm and 2.5 mm, 1.5 mm and 3.0 mm, 1.5 mm and 3.5 mm, 1.5 mm and 4.0 mm, 1.5 mm and 4.5 mm, 1.5 mm and 5.0 mm, 1.5 mm and 5.5 mm, 1.5 mm and 6.0 mm, 1.5 mm and 6.2 mm, 2.0 mm and 2.5 mm, 2.0 mm and 3.0 mm, 2.0 mm and 3.5 mm, 2.0 mm and 4.0 mm, 2.0 mm and 4.5 mm, 2.0 mm and 5.0 mm, 2.0 mm and 5.5 mm, 2.0 and 6.0 mm, 2.0 mm and 6.2 mm, 2.5 mm and 3.0 mm, 2.5 mm and 3.5 mm, 2.5 mm and 4.0 mm, 2.5 mm and 4.5 mm, 2.5 mm and 5.0 mm, 2.5 mm and 5.5 mm, 2.5 mm and 6.0 mm, 2.5 mm and 6.2 mm, 3.0 mm and 3.5 mm, 3.0 mm and 4.0 mm, 3.0 mm and 4.5 mm, 3.0 mm and 5.0 mm, 3.0 mm and 5.5 mm, 3.0 and 6.0 mm, 3.0 mm and 6.2 mm, 3.5 mm and 4.0 mm, 3.5 mm and 4.5 mm, 3.5 mm and 5.0 mm, 3.5 mm and 5.5 mm, 3.5 and 6.0 mm, 3.5 mm and 6.2 mm, 4.0 mm and 4.5 mm, 4.0 mm and 5.0 mm, 4.0 mm and 5.5 mm, 4.0 and 6.0 mm, 4.0 mm and 6.2 mm, 4.5 mm and 5.0 mm, 4.5 mm and 5.5 mm, 4.5 and 6.0 mm, 4.5 mm and 6.2 mm, 5.0 mm and 5.5 mm, 5.0 mm and 6.0 mm, 5.0 mm and 6.2 mm, 5.5 mm and 6.0 mm, 5.5 mm and 6.2 mm, or 6.0 mm and 6.2 mm).

In some instances, it may be desirable to configure hollow needles, needle assemblies, actuation units, apparatuses, kits, and methods of the invention to provide one or more tissue portions that do not include significant amounts of subcutaneous tissue, or, in other instances, to provide tissue portions that do include significant amounts of subcutaneous tissue. Electronic and/or physical mechanisms may be used to control the depth of penetration into the skin by the hollow needle(s) and the corresponding size of a cored tissue portion and hole. For example, an apparatus may include one or more one or more spacers as described herein; one or more scroll wheels, buttons, dials, toggles, or other components to physically retract the hollow needle(s); a z-actuation mechanism (e.g., a pneumatic, electromagnetic, or piezoelectric actuator or a motor with a cam); and/or one or more sensors (e.g., force sensors, optical sensors, laser fibers, photodetectors, and/or position sensors) in communication with one or more hollow needles, actuators, valves, pressure generating sources, and/or user interfaces to detect the position of hollow needle(s) and/or the position of the apparatus relative to the treated skin portion.

EXAMPLES

Example 1—Treatment of Skin Laxity in the Face Using a Hollow Needle with Two Prongs An apparatus of the invention may be used to administer treatment to the skin of a subject. Treatment may be performed outside of an operating room environment, thereby minimizing the cost of treatment.

The apparatus used for treatment of the subject may be any of those described herein. For example, the apparatus may be that shown in any one of FIGS. 16D-16I (e.g., apparatus 163 including actuation unit 151, needle assembly 10, and cover 161). For treatment of skin laxity in the face, a metallic, hollow needle with two prongs each having a bevel angle $\alpha$ of 30 degrees may be selected for application to a treatment area of about 4 mm by about 9 mm. The selected hollow needle may be a 24 gauge needle and may be affixed to the needle assembly of the apparatus at its proximal end (e.g., away from the needle tip). The tip of each prong of the hollow needle may be a sharp point (e.g., sharp point 51 as illustrated in FIG. 5A). The hollow needle may be configured to penetrate about 0.5 mm to about 2 mm (e.g., about 1 mm) into the skin and to remove an areal fraction of about 0.03 of skin tissue.

The skin area may first be sterilized, treated with chemicals, and/or otherwise prepared for treatment. The positioning mechanism disposed in the apparatus may be applied to position the hollow needle to the area of treatment. Treatment may proceed with the driving of the needle into and out of the skin by activation of the z-actuator, driving the needle containing the cored tissue portion inside its lumen to be in contact with the tissue removal tool (e.g., a piston), removal of cored tissue portion by activation of the vacuum pump coupled to the aspiration tube and the trap, and translation of the hollow needle or the entire apparatus to an adjacent region for treatment. When sufficient tissue area has been treated, the apparatus components may be powered off, the skin surface and/or holes are cleaned and/or flushed with fluid, and optionally a compressive wound dressing applied to the skin to cause the holes to close. The trap may be disposed of, and other components of the system may be detached and sterilized.

The treatment may be rapid (e.g., less than 30 minutes), minimizing patient downtime and allowing treatment to be carried out as an outpatient procedure. Within days, a reduction in skin laxity and/or rhytides in the treatment area may be observed.

Example 2—Treatment of Skin Laxity in the Face Using a Hollow Needle Having an Edge The hollow needle used in Example 1 may be replaced with a hollow needle having an edge. For example, the hollow needle used to treat skin laxity in the face may be a metallic, hollow needle with two prongs each having a bevel angle $\alpha$ of 30 degrees. The hollow needle may be a 24 gauge needle and may be affixed to the needle assembly of the apparatus at its proximal end (e.g., away from the needle tip). The tip of each prong of the hollow needle may be an edge (e.g., edge 52 as illustrated in FIG. 5B). The hollow needle may be configured to penetrate about 0.5 mm to about 2 mm (e.g., about 1 mm) into the skin and to remove an areal fraction of about 0.03 of skin tissue.

Example 3—Treatment of Skin Laxity in the Face Using a Hollow Needle Having a Flat Tip The hollow needle used in Example 1 may be replaced with a hollow needle having a flat tip (e.g., a two dimensional flat tip). For example, the hollow needle used to treat skin laxity in the face may be a metallic, hollow needle with two prongs each having a bevel angle $\alpha$ of 30 degrees. The hollow needle may be a 24 gauge needle and may be affixed to the needle assembly of the apparatus at its proximal end (e.g., away from the needle tip). The tip of each prong of the hollow needle may be a flat tip (e.g., flat tip 53 as illustrated in FIG. 5C). The hollow needle may be configured to penetrate about 0.5 mm to about 2 mm (e.g., about 1 mm) into the skin and to remove an areal fraction of about 0.03 of skin tissue.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent, or patent application was specifically and individually indicated to be incorporated by reference in its entirety.

Other embodiments are within the following claims.

The invention claimed is:

1. A needle assembly comprising:
a hollow needle having a lumen,
a z-actuator to displace the hollow needle from an uppermost position along a longitudinal axis of the hollow needle to extend (i) into the dermal layer, (ii) through the entire dermal layer to the junction of the dermal layer and the subcutaneous fat layer, or (iii) into the subcutaneous fat layer,
a tissue removal tool within the lumen to facilitate removal of portions of the skin tissue from the hollow needle, wherein the hollow needle comprises at least a first prong provided at a distal end of the hollow needle, and
an aspiration tube coupled to a low pressure source, wherein the aspiration tube has an opening that is disposed adjacent to the distal end of the hollow needle when the hollow needle is in the uppermost position, thereby aspirating the portions of the skin tissue into the aspiration tube when vacuum from the low pressure source is applied to the distal end of the hollow needle,
wherein the portions of the skin tissue are aspirated into the aspiration tube distally through only the distal end of the hollow needle.

2. The needle assembly of claim 1, wherein the hollow needle further comprises a second prong.

3. The needle assembly of claim 1, wherein an angle (a) between a lateral side of the first prong and the longitudinal axis of the hollow needle is at least about 20 degrees.

4. The needle assembly of claim 1, wherein an angle (a) between a lateral side of the first prong and the longitudinal axis of the hollow needle is less than about 20 degrees.

5. The needle assembly of claim 2, wherein an angle (a) between a lateral side of the second prong and the longitudinal axis of the hollow needle is at least about 20 degrees.

6. The needle assembly of claim 2, wherein an angle (a) between a lateral side of the second prong and the longitudinal axis of the hollow needle is less than about 20 degrees.

7. The needle assembly of claim 1, wherein the needle assembly is detachably attached to an x- and/or y-actuator.

8. The needle assembly of claim 1, wherein the tissue removal tool is controllably translatable along the longitudinal axis of the hollow needle.

9. The needle assembly of claim 1, wherein the tissue removal tool is a piston.

10. The needle assembly of claim 9, wherein the piston comprises a round tip at a distal end of the piston.

11. The needle assembly of claim 1, wherein the portions of the skin tissue removed by the tissue removal tool from the lumen of the hollow needle are substantially intact tissue portions.

12. The needle assembly of claim 1, wherein the aspiration tube is coupled to a trap, wherein the low pressure source provides suction or vacuum at the distal end of the hollow needle of between about −8 mmHg and about −16 mmHg.

13. The needle assembly of claim 12, wherein the low pressure source is a vacuum pump.

14. The needle assembly of claim 1, comprising a low-pressure conduit coupled to the hollow needle, wherein the low-pressure conduit is connected to the low pressure source to generate suction in the hollow needle.

15. The needle assembly of claim 14, wherein the low pressure source is a vacuum pump.

16. The needle assembly of claim 1, comprising a spacer.

17. The needle assembly of claim 16, wherein the spacer is attached to a cover, wherein the spacer is positioned between the cover and the skin tissue, and wherein the spacer is configured to control the depth of insertion of the hollow needle.

18. The needle assembly of claim 1, wherein an angle ($\alpha$) between a lateral side of at least one of the first prong and the second prong, and the longitudinal axis of the hollow needle is 10 degrees.

19. A needle assembly comprising:
a hollow needle having a lumen,
a z-actuator to displace the hollow needle from an uppermost position along a longitudinal axis of the hollow needle to extend (i) into the dermal layer, (ii) through the entire dermal layer to the junction of the dermal layer and the subcutaneous fat layer, or (iii) into the subcutaneous fat layer,
a tissue removal tool within the lumen to facilitate removal of cored portions of the skin tissue from the hollow needle, wherein the hollow needle comprises at least a first prong provided at a distal end of the hollow needle, and
an aspiration tube coupled to a low pressure source and a trap, wherein the aspiration tube has an opening that is disposed in proximity to the distal end of the hollow needle when the hollow needle is in the uppermost position such that when the low pressure source provides suction or vacuum at the distal end of the hollow needle of between about −8 mmHg and about −16 mmHg, cored tissue is removed from the distal end of the hollow needle,
wherein the opening is disposed closer to the distal end of the hollow needle than the proximal end of the hollow needle.

20. A needle assembly comprising:
a hollow needle having a lumen,
a z-actuator to displace the hollow needle from an uppermost position along a longitudinal axis of the hollow needle to extend (i) into the dermal layer, (ii) through the entire dermal layer to the junction of the dermal layer and the subcutaneous fat layer, or (iii) into the subcutaneous fat layer,
a tissue removal tool within the lumen to facilitate removal of portions of the skin tissue from the hollow needle, wherein the hollow needle comprises at least a first prong provided at a distal end of the hollow needle, and
an aspiration tube coupled to a low pressure source, wherein the aspiration tube has an opening that is disposed adjacent to the distal end of the hollow needle when the hollow needle is in the uppermost position, thereby aspirating the portions of the skin tissue into the aspiration tube when vacuum from the low pressure source is applied to the distal end of the hollow needle, wherein the aspiration tube runs alongside the hollow needle, and wherein the opening is disposed immediately adjacent the distal end of the hollow needle.

* * * * *